United States Patent
Cragg et al.

(10) Patent No.: US 9,333,318 B2
(45) Date of Patent: May 10, 2016

(54) SLEEP APNEA DEVICE

(71) Applicant: FRESCA MEDICAL, INC., San Clemente, CA (US)

(72) Inventors: Andrew H. Cragg, Edina, MN (US); John Logan, Plymouth, MN (US); John Trusheim, Chaska, MN (US); John Nolting, Poway, CA (US); Eugene Chen, Carlsbad, CA (US); Mark Adler, Carlsbad, CA (US)

(73) Assignee: FRESCA Medical, Inc., San Clemente, CA (US)

( * ) Notice: Subject to any disclaimer, the term of this patent is extended or adjusted under 35 U.S.C. 154(b) by 306 days.

(21) Appl. No.: 13/860,926

(22) Filed: Apr. 11, 2013

(65) Prior Publication Data

US 2013/0312757 A1 Nov. 28, 2013

Related U.S. Application Data

(60) Provisional application No. 61/623,855, filed on Apr. 13, 2012, provisional application No. 61/775,430, filed on Mar. 8, 2013.

(51) Int. Cl.
*A61M 16/06* (2006.01)
*A61M 16/20* (2006.01)
(Continued)

(52) U.S. Cl.
CPC .............. *A61M 16/208* (2013.01); *A61M 16/00* (2013.01); *A61M 16/0057* (2013.01);
(Continued)

(58) Field of Classification Search
CPC ........... A47L 7/00; A47L 7/0085; A47L 9/00; A47L 9/0081; A61B 5/00; A61B 5/0836;
(Continued)

(56) References Cited

U.S. PATENT DOCUMENTS 4,655,213 A * 4/1987 Rapoport et al. ........ 128/205.25
4,823,828 A 4/1989 McGinnis
(Continued)

FOREIGN PATENT DOCUMENTS

EP 1893267 A1 11/2011
EP 2287471 B1 6/2012
(Continued)

OTHER PUBLICATIONS

CPAP Systems and Accessories: Comfort Accuracy and High Flows. Vital Signs, Inc. General Electric Healthcare Company. 2009, 2 pages.
Deegan, P., et al. Effects of positive airway pressure on upper airway dilator muscle activity and ventilatory timing. Journal of Applied Physiol. Jul. 1996; 81(1): 470-9.
Duncan, A., et al. PEEP and CPAP. Anaesth Intensive Care. Aug. 1986; 14(3): 236-50.
Garrard, C., et al. The effects of expiratory positive airway pressure on functional residual capacity in normal subjects. Crit Care Med. Sep.-Oct. 1978; 6(5): 320-2.
(Continued)

*Primary Examiner* — Annette Dixon
(74) *Attorney, Agent, or Firm* — Manuel de la Cerra

(57) ABSTRACT

A system for treating a patient suffering from obstructive sleep apnea may include a mask, a portable air flow generator configured to generate air flow at a relatively low flow rate, and a tube connecting the air flow generator and the mask such that air flow from the generator passes through an air flow generator valve on the mask. The mask may include a contact surface for forming a seal between the mask and the patient's face such that the mask surrounds the patient's nostrils, an expiration valve that opens during expiration, and an air flow generator valve that opens during inspiration. In some embodiments, the mask may further include an inspiration valve that opens during inspiration to allow air from outside the system to enter the mask.

23 Claims, 46 Drawing Sheets

(51) Int. Cl.
*A61M 16/00* (2006.01)
*A61M 16/08* (2006.01)

(52) U.S. Cl.
CPC .......... *A61M 16/06* (2013.01); *A61M 16/0683* (2013.01); *A61M 16/0833* (2014.02); *A61M 16/0866* (2014.02); *A61M 16/20* (2013.01); *A61M 16/0069* (2014.02); *A61M 16/0688* (2014.02); *A61M 16/0875* (2013.01); *A61M 16/202* (2014.02); *A61M 16/209* (2014.02); *A61M 2016/0039* (2013.01); *A61M 2016/0661* (2013.01); *A61M 2205/42* (2013.01); *A61M 2205/8206* (2013.01); *A61M 2209/088* (2013.01); *A61M 2230/205* (2013.01)

(58) Field of Classification Search
CPC ..... A61B 5/11; A61B 5/4809; A61B 5/4818; A61B 5/4836; A61F 5/56; A61G 10/023; A61G 10/04; A61H 33/02; A61H 33/028; A61M 11/00; A61M 16/00; A61M 16/0003; A61M 16/0045; A61M 16/0051; A61M 16/0057; A61M 16/0069; A61M 16/0084; A61M 16/06; A61M 16/0633; A61M 16/0666; A61M 16/0683; A61M 16/0694; A61M 16/08; A61M 16/0833; A61M 16/0866; A61M 16/0875; A61M 16/12; A61M 16/20; A61M 16/201; A61M 16/202; A61M 16/205; A61M 16/206; A61M 16/208; A61M 16/209; A62B 17/04; A62B 7/00; A62B 7/14; A62B 9/00; A62B 9/02; F04D 29/66; F04D 29/663; H02K 5/24; H02K 9/00; H02K 9/26
USPC ............. 128/200.14, 200.24, 201.23, 204.18, 128/204.19, 204.21, 204.23, 204.25, 128/204.26, 204.28, 205.11, 205.13, 128/205.14, 205.17, 205.18, 2, 205.24, 128/205.25, 205.26, 205.28, 206.21, 128/207.12, 848, 857, 911, 914
See application file for complete search history.

(56) References Cited

U.S. PATENT DOCUMENTS

| | | | |
|---|---|---|---|
| 5,065,756 A * | 11/1991 | Rapoport | 128/204.18 |
| 5,301,689 A * | 4/1994 | Wennerholm | 128/848 |
| 5,567,127 A | 10/1996 | Wentz | |
| 5,649,533 A | 7/1997 | Oren | |
| 5,881,718 A | 3/1999 | Mortensen et al. | |
| 6,123,071 A | 9/2000 | Berthon-Jones et al. | |
| 6,182,657 B1 | 2/2001 | Brydon et al. | |
| 6,526,974 B1 | 3/2003 | Brydon et al. | |
| 6,561,190 B1 | 5/2003 | Kwok | |
| 6,561,191 B1 | 5/2003 | Kwok | |
| 6,581,594 B1 | 6/2003 | Drew et al. | |
| 6,581,601 B2 | 6/2003 | Ziaee | |
| 6,595,212 B1 | 7/2003 | Arnott | |
| 6,662,803 B2 | 12/2003 | Gradon et al. | |
| 6,691,707 B1 | 2/2004 | Gunaratnam et al. | |
| 6,752,150 B1 | 6/2004 | Remmers et al. | |
| 6,823,865 B2 | 11/2004 | Drew et al. | |
| 6,923,181 B2 | 8/2005 | Tuck | |
| 7,011,090 B2 | 3/2006 | Drew et al. | |
| 7,063,086 B2 | 6/2006 | Shahbazpour et al. | |
| 7,066,174 B1 | 6/2006 | Smith et al. | |
| 7,066,178 B2 | 6/2006 | Gunaratnam et al. | |
| 7,159,587 B2 | 1/2007 | Drew et al. | |
| 7,207,335 B2 | 4/2007 | Kwok et al. | |
| 7,341,060 B2 | 3/2008 | Ging et al. | |
| 7,520,277 B1 * | 4/2009 | Grady | 128/201.23 |
| 7,523,753 B2 | 4/2009 | Gunaratnam et al. | |
| 7,527,055 B2 | 5/2009 | McAuliffe et al. | |
| 7,597,100 B2 | 10/2009 | Ging et al. | |
| 7,735,491 B2 | 6/2010 | Doshi et al. | |
| 7,735,492 B2 | 6/2010 | Doshi et al. | |
| 7,798,148 B2 | 9/2010 | Doshi et al. | |
| 7,806,120 B2 | 10/2010 | Loomas et al. | |
| 7,845,354 B2 | 12/2010 | Kwok et al. | |
| 7,856,979 B2 | 12/2010 | Doshi et al. | |
| 7,874,293 B2 | 1/2011 | Gunaratnam et al. | |
| 7,878,199 B2 | 2/2011 | Ging et al. | |
| 7,926,487 B2 | 4/2011 | Drew et al. | |
| 7,934,501 B2 | 5/2011 | Fu et al. | |
| 7,942,150 B2 | 5/2011 | Guney et al. | |
| 7,967,013 B2 | 6/2011 | Ging et al. | |
| 7,992,564 B2 | 8/2011 | Doshi et al. | |
| 8,011,369 B2 | 9/2011 | Gunaratnam et al. | |
| 8,025,055 B1 * | 9/2011 | Grady | 128/205.26 |
| 8,061,357 B2 | 11/2011 | Pierce et al. | |
| 8,074,646 B2 * | 12/2011 | Daly | 128/204.18 |
| 8,122,884 B2 | 2/2012 | Daly et al. | |
| 8,122,886 B2 | 2/2012 | Kwok et al. | |
| 8,136,524 B2 | 3/2012 | Ging et al. | |
| 8,210,182 B2 | 7/2012 | Duquette et al. | |
| 8,215,308 B2 | 7/2012 | Doshi et al. | |
| 8,235,046 B2 | 8/2012 | Doshi et al. | |
| 8,240,309 B2 | 8/2012 | Doshi et al. | |
| 8,286,636 B2 | 10/2012 | Gunaratnam et al. | |
| 8,291,909 B2 | 10/2012 | Doshi et al. | |
| 8,297,285 B2 | 10/2012 | Henry et al. | |
| 8,302,606 B2 | 11/2012 | Doshi et al. | |
| 8,337,145 B2 | 12/2012 | Frater et al. | |
| 8,365,736 B2 | 2/2013 | Doshi et al. | |
| 8,371,300 B2 | 2/2013 | Rapoport | |
| 8,371,304 B2 | 2/2013 | Duquette et al. | |
| 8,397,727 B2 | 3/2013 | Ng et al. | |
| 8,402,972 B2 | 3/2013 | Lang et al. | |
| 8,439,039 B2 | 5/2013 | Gunaratnam et al. | |
| 8,573,201 B2 | 11/2013 | Rummery et al. | |
| 8,839,791 B2 | 9/2014 | Allum et al. | |
| 8,844,529 B2 | 9/2014 | Selvarajan et al. | |
| 8,844,531 B2 | 9/2014 | Witt et al. | |
| 8,844,533 B2 | 9/2014 | Allum et al. | |
| 9,027,553 B2 | 5/2015 | Witt et al. | |
| 9,072,855 B2 | 7/2015 | McAuley et al. | |
| 9,132,250 B2 | 9/2015 | Allum et al. | |
| 9,138,555 B2 | 9/2015 | McAuley et al. | |
| 9,144,658 B2 | 9/2015 | Li et al. | |
| 2003/0127096 A1 | 7/2003 | McAuliffe | |
| 2006/0150978 A1 | 7/2006 | Doshi et al. | |
| 2009/0065729 A1 | 3/2009 | Worboys et al. | |
| 2009/0133700 A1 | 5/2009 | Martin et al. | |
| 2009/0194109 A1 | 8/2009 | Doshi | |
| 2010/0252041 A1 | 10/2010 | Kapust et al. | |
| 2011/0011400 A1 | 1/2011 | Gentner et al. | |
| 2011/0155133 A1 | 6/2011 | Barnes et al. | |
| 2011/0253147 A1 | 10/2011 | Gusky et al. | |
| 2011/0259331 A1 * | 10/2011 | Witt | A61M 16/0666 128/204.18 |
| 2011/0259340 A1 | 10/2011 | Witt et al. | |
| 2012/0111331 A1 | 5/2012 | Witt et al. | |
| 2012/0227742 A1 | 9/2012 | Witt et al. | |
| 2012/0234323 A1 | 9/2012 | Connor | |
| 2012/0325205 A1 | 12/2012 | Allum | |
| 2012/0325211 A1 | 12/2012 | Allum | |
| 2012/0325218 A1 | 12/2012 | Brambilla | |
| 2012/0330183 A1 | 12/2012 | Allum | |
| 2013/0133656 A1 | 5/2013 | Nightingale et al. | |
| 2013/0184602 A1 | 7/2013 | Brambilla | |
| 2013/0186394 A1 | 7/2013 | Hallett | |
| 2013/0255684 A2 | 10/2013 | Allum et al. | |
| 2014/0053846 A1 | 2/2014 | Wood | |
| 2015/0034079 A1 | 2/2015 | Allum et al. | |
| 2015/0040907 A1 | 2/2015 | Hakim | |
| 2015/0128948 A1 | 5/2015 | Rapoport | |

FOREIGN PATENT DOCUMENTS

| | | |
|---|---|---|
| EP | 2530327 A2 | 12/2012 |
| GB | 2021421 A | 12/1979 |
| WO | 9741812 A1 | 11/1997 |
| WO | 0132251 A1 | 5/2001 |

(56) References Cited

FOREIGN PATENT DOCUMENTS

| WO | 0215969 A2 | 2/2002 |
|---|---|---|
| WO | 2009089807 A1 | 7/2009 |
| WO | 2012048364 A1 | 4/2012 |

OTHER PUBLICATIONS

Gillick, JS. Spontaneous positive end-expiratory pressure (sPEEP). Anesthesia & Analgesia. Sep.-Oct. 1977; 56(5): 627-32. PubMed PMID: 333990.

Heinzer R, et al. Effect of expiratory positive airway pressure on sleep disordered breathing. Sleep. Mar. 2008; 31(3): 429-32.

Juhasz, J. et al. Proportional positive airway pressure: a new concept to treat obstructive sleep apnoea. European Respiratory Journal. 2001; 17: 467-473.

Layon, J., et al. Continuous positive airway pressure and expiratory positive airway pressure increase functional residual capacity equivalently. Chest. Apr. 1986;89(4):517-21.

Resta, O., et al. The role of the expiratory phase in obstructive sleep apnoea. Respir Med. Mar. 1999;93(3):190-5.

Sanders, M., et al. Obstructive sleep apnea treated by independently adjusted inspiratory and expiratory positive airway pressures via nasal mask. Physiologic and clinical implications. Chest. Aug. 1990; 98(2): 317-24.

Schlobohm, R., et al. Lung volumes, mechanics, and oxygenation during spontaneous positive-pressure ventilation: the advantage of CPAP over EPAP. Anesthesiology. Oct. 1981;55(4):416-22.

Schmidt, G., et al. EPAP without intubation. Crit Care Med. Jul.-Aug. 1977; 5(4): 207-9.

Series, F., et al. Changes in upper airway resistance with lung inflation and positive airway pressure. American Physiological Society. Mar. 1990; 68(3): 1075-1079.

Sturgeon, C. Jr, et al. PEEP and CPAP: cardiopulmonary effects during spontaneous ventilation. Anesth Analg. Sep.-Oct. 1977; 56(5):633-41. PubMed PMID: 20822.

Tummons, J. A positive end-expiratory pressure-nasal-assist device (PEEP-NAD) for treatment of respiratory distress syndrome. Anesthesiology. Jun. 1973; 38(6):592-5.

U.S. Appl. No. 29/448,107, filed Mar. 8, 2013, Gordon et al.
U.S. Appl. No. 29/461,138, filed Jul. 18, 2013, Chen et al.
U.S. Appl. No. 29/461,144, filed Jul. 18, 2013, Chen et al.
U.S. Appl. No. 29/461,143, filed Jul. 18, 2013, Chen et al.
U.S. Appl. No. 29/464,533, filed Aug. 16, 2013, Chen et al.
U.S. Appl. No. 29/465,007, filed Aug. 22, 2013, Chen et al.

Search Report and Written Opinion issued in PCT/US13/36246 mailed Sep. 6, 2013.

International Search Report issued Nov. 18, 2014 in PCT/US2014/038215 (6 pages).

\* cited by examiner

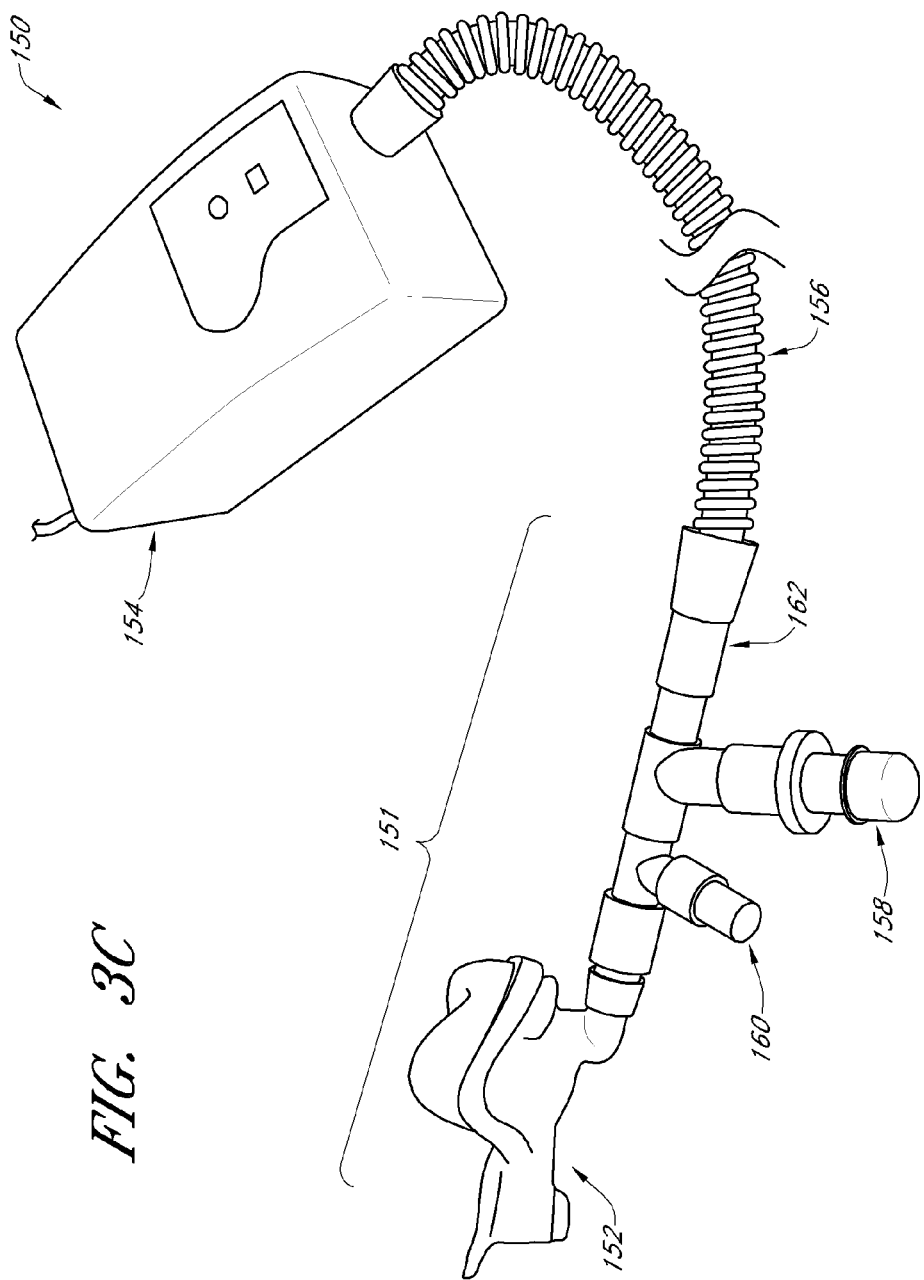

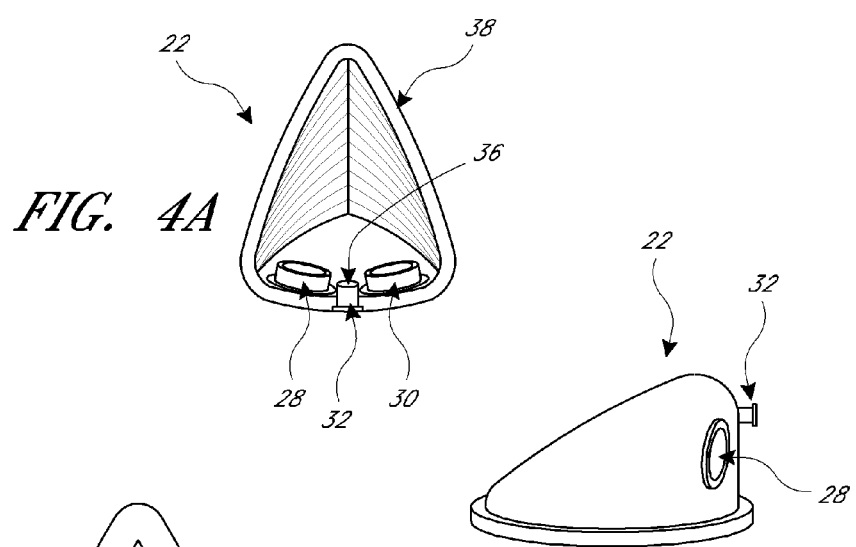
FIG. 4A
FIG. 4E
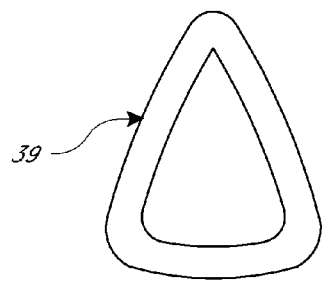
FIG. 4C
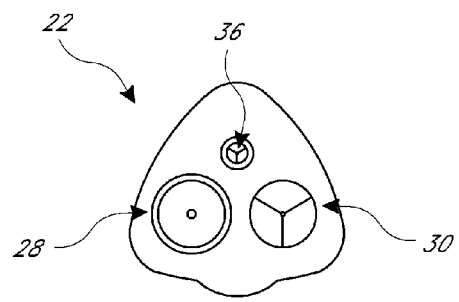
FIG. 4D
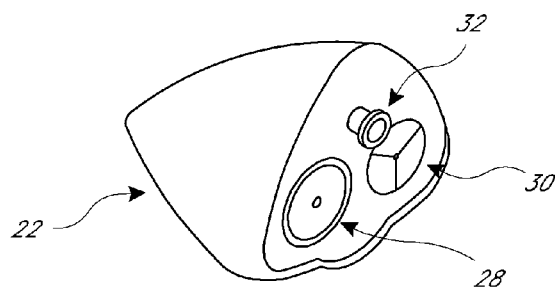
FIG. 4B

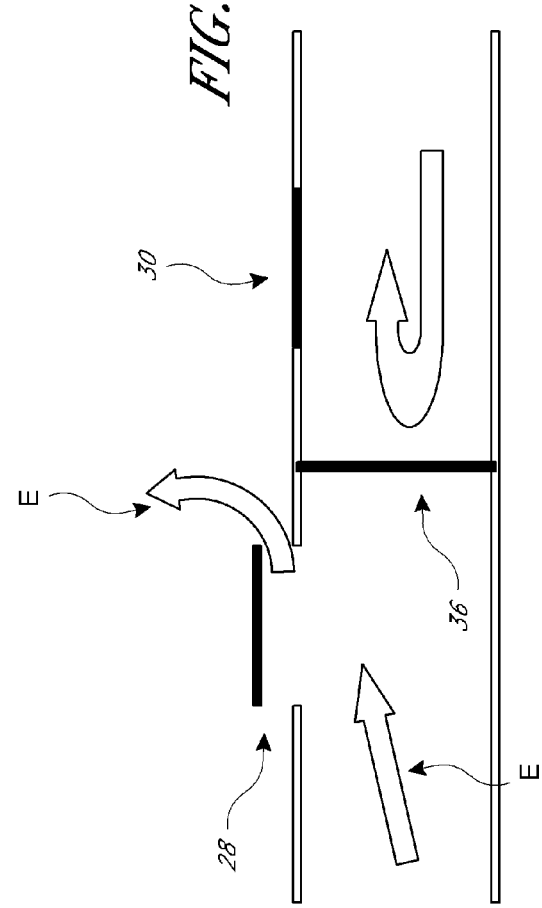
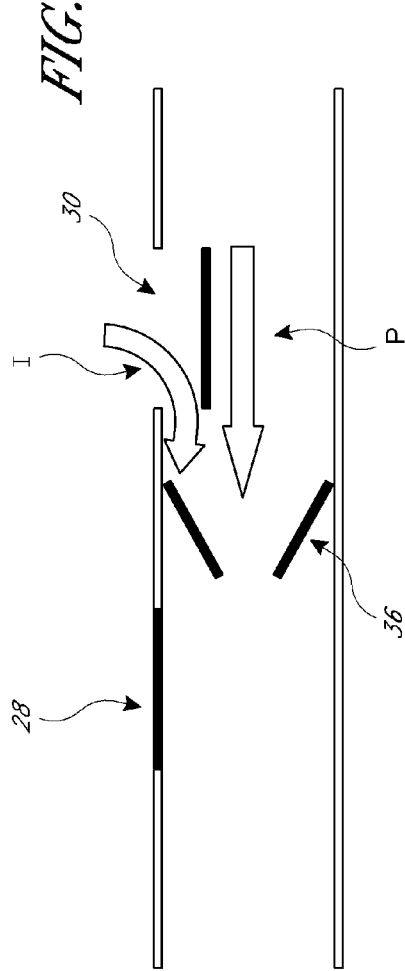
FIG. 5A
FIG. 5B

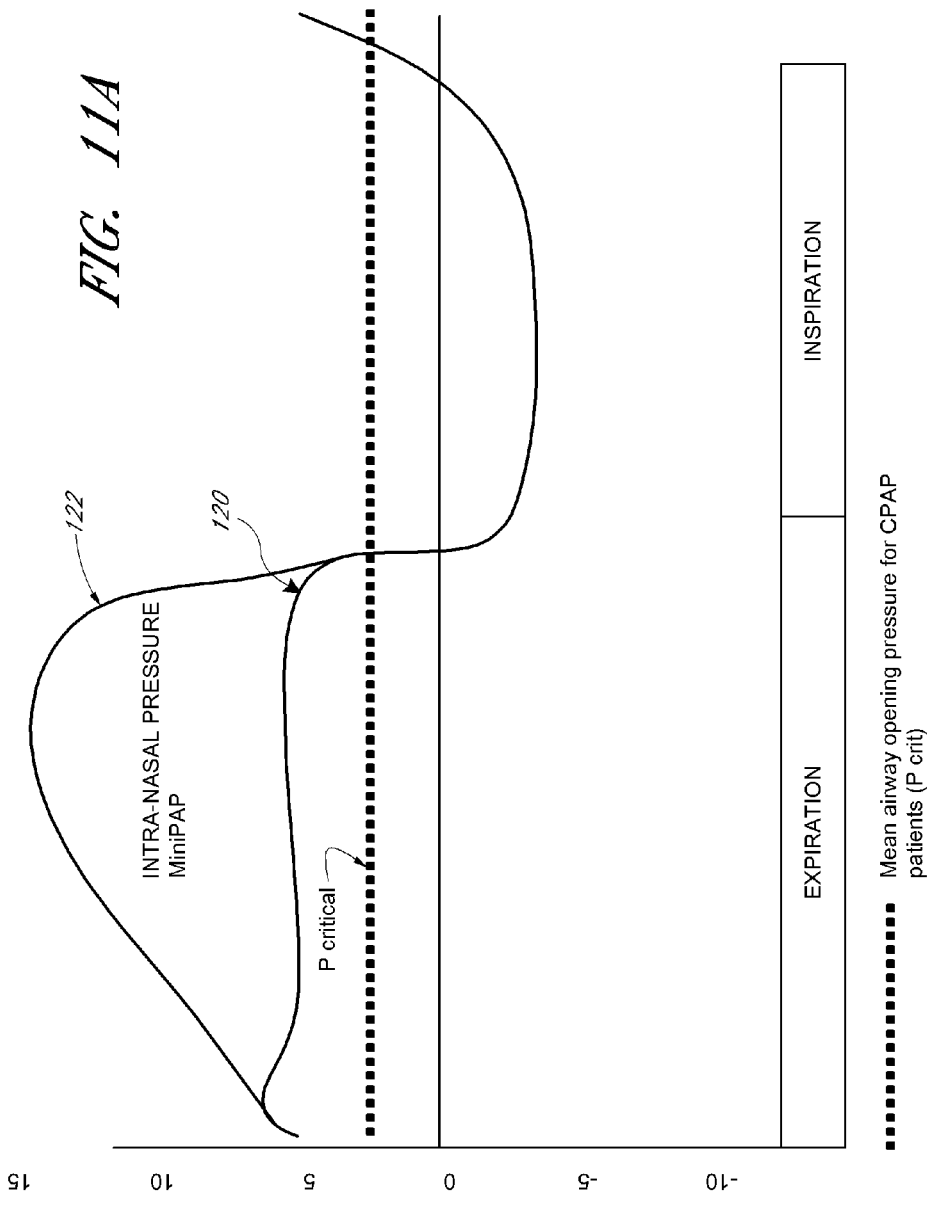

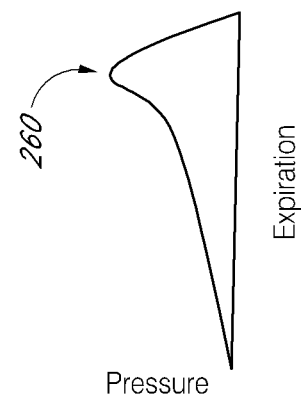
FIG. 12A    FIG. 12B    FIG. 12C

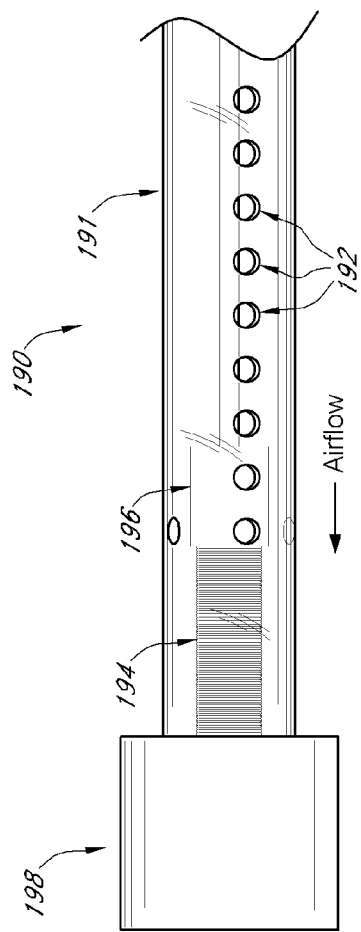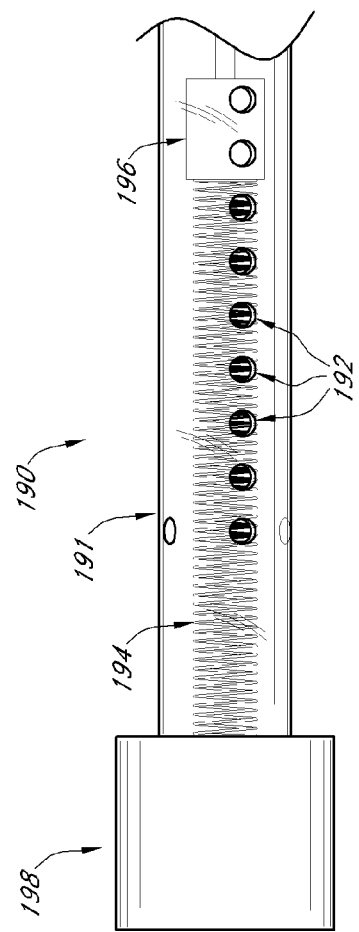

SLEEP APNEA DEVICE

PRIORITY CLAIM

The present application claims priority benefit under 35 U.S.C. §119(e) of U.S. Provisional Application Ser. No. 61/623,855, filed Apr. 13, 2012, entitled "Sleep Apnea Device" and U.S. Provisional Application Ser. No. 61/775,430, filed Mar. 8, 2013, entitled "Sleep Apnea Device," the disclosures of which are incorporated herein by reference.

BACKGROUND

1. Field

The present invention is related to medical systems, devices and methods. More specifically, the invention is related to systems, devices and methods for treating obstructive sleep apnea or snoring.

2. Description of the Related Art

Obstructive sleep apnea (OSA) is a common medical disorder that can be quite serious. Approximately 1 in 22 Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep, because the airway has become narrowed, blocked, or floppy. (See FIG. 1A illustrating an airway A during normal breathing and FIG. 1B illustrating the airway A during OSA.) A pause in breathing is called an apnea episode, while a decrease in airflow during breathing is called a hypopnea episode. Almost everyone has brief apnea or hypopnea episodes while they sleep. In OSA, however, apnea episodes occur more frequently and/or last longer than in the general population. OSA has become an increasingly costly medical condition in recent years, as the disorder is more prevalent in obese people and obesity has become significantly more prevalent. Unfortunately, the currently available options for treating OSA are not ideal.

A person with OSA usually begins snoring heavily soon after falling asleep. Often the snoring gets louder. The snoring is then interrupted by a long silent period during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy, impatient, or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). As shown in FIG. 2, a CPAP system typically 10 consists of a mask 12a-12c fitting in or over the nose or nose and mouth, an air pressurizing console 14 and a tube 16 connecting the two. CPAP works by pressurizing the upper airway throughout the breathing cycle, essentially inflating the airway to keep it open and thus creating what is sometimes referred to as a "pneumatic splint." Because the masks 12a-12c typically leak air, CPAP systems have to provide an airflow rate of up to 200 liters per minute (approximate figure based on unpublished data). This high flow rate makes breathing feel quite uncomfortable for many patients and requires a relatively large, noisy pressurizing console 14. Additionally, the high required flow rates of CPAP often cause discomfort during exhalation due to increased resistance, as well as nasal dryness, dry mouth, ear pain, rhinitis, abdominal bloating and/or headaches.

The overwhelming shortcoming of CPAP is poor patient compliance. Over half of all patients who try CPAP stop using it. Patients dislike the side effects mentioned above, as well as having to wear an uncomfortable, claustrophobic mask, being tethered to a pressurizing console, the noise of the console, traveling with a bulky device, and a loss of personal space in bed.

Many CPAP devices and alternatives to CPAP have been developed, but all have significant shortcomings. Less invasive attempts at OSA treatment, such as behavior modification, sleep positioning and removable splints to be worn in the mouth, rarely work. A number of different surgical approaches for treating OSA have also been tried, some of which are still in use. For example, Uvulopalatopharyngoplasty (UPPP) and Laser Assisted Uvula Palatoplasty (LAUP) are currently used. Surgical approaches, however, are often quite invasive and not always effective at treating OSA.

One alternative approach to OSA treatment is to provide a pneumatic splint during the expiratory portion of the respiratory cycle by producing a partial blockage in the nose or mouth, thus slowing the release of air during expiration and increasing positive pressure in the airway. The simplest way to form an expiratory pneumatic splint, pursing the lips, has been shown to open the upper airway and improve breathing in emphysema patients. This type of maneuver is generically labeled Expiratory Positive Airway Pressure (EPAP).

Ventus Medical, Inc. (http://www.proventtherapy.com/ventus medical) has developed a removable nasal EPAP device to produce such a pneumatic splint during exhalation (the Provent® Sleep Apnea Therapy). (See, for example, Doshi et al., U.S. Patent Application Pub. No. 2006/0150978.) This device restricts exhalation by forcing expired air through several small orifices attached to the nose. This is labeled a Fixed Orifice Resistor (FOR). One shortcoming of this therapy is that 1) the fixed hole exhalation valve does not have a capped maximum pressure, 2) the pressure increases immediately upon exhalation and therefore makes it difficult to exhale, and 3) with no assistance of additional pressure from an external source, if the patient has an apneic event there is no 'rescue pressure'. A further disadvantage is that the Provent® device or any FOR restricts expiratory airflow using a fixed hole for resistance. This leads to an uncomfortable spike in nasal pressure at the beginning of expiration when airflow is highest and a less efficacious decrease in nasal pressure at the end of expiration when airflow is lowest. Another shortcoming of the Provent® device is that it produces the pneumatic splint only during exhalation—i.e., there is no increased pressure during inhalation.

In addition, the device is not effective in mouth breathers or patients who become mouth breathers when resistance is added to the nasal passages. Thus, the Provent® device is useful only in moderate cases of OSA that do not convert to mouth breathing.

Although snoring is not as severe a condition as OSA, it does affect lives adversely. Snoring can adversely affect sleep quality and can make sleeping with a spouse or other partner difficult. Although many snoring therapies have been tried, including Breathe Right® Nasal Strips and more invasive approaches in more severe cases, no ideal solution has been found.

Therefore, it would be advantageous to have improved systems, devices and methods for treating OSA and/or snoring. Ideally, such systems, devices and methods would be less cumbersome than currently available CPAP systems, to improve patient compliance. Also ideally, such systems, devices and methods would provide some of the advantages of an expiratory pneumatic splint. At least some of these objectives will be met by the embodiments described in this application.

BRIEF SUMMARY

The various embodiments described below are directed to the treatment of obstructive sleep apnea, snoring and/or possibly other conditions with a device and system that are smaller, lighter and less cumbersome than a traditional CPAP system, with fewer side effects and less discomfort. As mentioned above, currently available CPAP systems generally include three components—an airflow generator, a mask, and a tube connecting the two. Various embodiments described in this application provide improvements in one, two or all three of these components or provide a solution with fewer components, thus facilitating the treatment of sleep apnea and/or snoring.

One improvement provided by the embodiments described herein is variable resistance to expiratory air flow using a resistive mechanism other than infused external air that increases over the course of expiration, thus providing an easier, more comfortable start to expiration while maintaining airway pressure toward the end of expiration. Another improvement in various embodiments is that lower air flow rates are used, thus requiring less power and smaller device components than traditional CPAP and reducing side effects. Still another improvement is a less cumbersome, more form fitting mask that reduces air leaks and is more comfortable to wear than current CPAP masks and eliminates the need for high flow rates (to compensate for air leaks). These and other improvements, described in further detail below, may help improve patient compliance and overall treatment of sleep apnea. In some embodiments, the devices and methods described may also be used to treat snoring.

In one aspect of the present invention, a system for treating a patient suffering from obstructive sleep apnea or snoring may include: a mask having a contact surface for forming a seal between the mask and the patient's face such that the mask surrounds at least the patient's nostrils; a portable air flow generator configured to generate air flow at a relatively low flow rate; a tube connecting the air flow generator and the mask such that air flow from the generator passes through the air flow generator valve; a one-way, variable resistance expiration valve coupled with the mask or the tube to allow exhaled air to exit the mask during exhalation; and an air flow generator valve coupled with the mask or the tube to allow air from the air flow generator to enter the mask during inspiration. The expiration valve may provide less resistance to expired air during an early portion of expiration than during a later portion of expiration.

In some embodiments, the mask may surround the patient's nostrils and mouth. Optionally, the system may further include an inspiration valve in the mask or the tube that opens during inspiration to allow outside air to enter the mask. In various embodiments, the expiration valve may have an opening pressure of between about 0 cm H2O and about 15 cm H2O, and more preferably between about 2 cm H2O and about 5 cm H2O. In some embodiments, the expiration valve may open at an opening pressure of about 0-5 cm H2O and close at a pressure of at least about 5 cm H2O.

In some embodiments, the expiration valve may generate an intra-airway pressure of about 0-5 cm H2O during the early portion of expiration and an intra-airway pressure of about 5-15 cm H2O during the later portion of expiration. More generally, the expiration valve generates greater intra-airway pressure during the later portion of expiration than during the early portion. To accomplish this, the expiration valve may open to a largest open surface area at an opening pressure and close continuously during expiration. Alternatively, the expiration valve may open to a largest open surface area at an opening pressure and close incrementally during expiration. Furthermore, in some embodiments, an opening of the expiration valve may have a larger surface area during the early portion of expiration and a smaller surface area during the later portion of expiration. For example, an opening of the expiration valve may have a larger diameter during the early portion of expiration and a smaller diameter during the later portion of expiration.

In some embodiments, the system may further include a controller for opening and closing the expiration valve. Optionally, a wireless device may be included for sending signals to the controller to open and close the valve. In alternative embodiments, the expiration valve may open and close in response to expiratory pressure generated by exhalation of the patient. In some embodiments, the expiration valve may open at an opening pressure and close completely at an end of expiration.

Any of a wide variety of one-way, variable resistance expiration valves may be used. In one embodiment, for example, the expiration valve may be a Nitinol disk valve including a Nitinol plate that flexes to allow expired air to pass through the valve. In an alternative embodiment, the expiration valve may be an elastic membrane with multiple small apertures, where the elastic membrane expands in response to increasing expiratory pressure to enlarge the diameter of the apertures, thus allowing expired air to pass through the membrane, and shrinks in response to decreasing expiratory pressure to shrink the diameter of the apertures, thus helping to maintain pressure in the patient's pharynx. In another alternative embodiment, the expiration valve may be an aperture that opens to an initial opening diameter and closes during expiration. In yet another alternative embodiment, the expiration valve may include a tube having multiple holes and a spring loaded hole blocker disposed within the tube and configured to block fewer holes at a start of expiration and an increasing number of holes during expiration, such that resistance increases during expiration. In another alternative embodiment, the expiration valve may be an air resistance wheel coupled with a spring that increases resistance of the wheel during expiration. In another alternative embodiment, the expiration valve may be an elastomeric tube with an internal diameter of 2-5 mm that is compressed on by a fulcrum. The fulcrum is further acted on by the pressure of expired air such that increasing expiratory airflow causes the fulcrum to release pressure on the expiratory tube allowing more air to pass through the tube.

In some embodiments, the mask may further include a port for connecting with the tube to direct air into the air flow generator valve. The contact surface of the mask, in some embodiments, may include an adhesive. In many embodiments, the mask does not require a strap to remain in contact with the patient's face. In some embodiments, the mask forms an open space between the mask and the patient's face of no more than 10 milliliters, and the mask has a surface contact area with the patient's face of at least 5 square centimeters.

In various embodiments, the air flow generator may include, but is not limited to, a turbine pump, double bellows, a dual counter turbine or an air compressor and return. In various embodiments, the relatively low flow rate provided by the air flow generator may be between about 1 liter per minute and about 15 liters per minute. The airflow generator would have a back pressure or 2-15 cm H2O at flow rates of 1-15 liters per minute. In some embodiments, the air flow generator may be battery powered. Optionally, such embodiments may further include a breath-powered energy generation mechanism coupled with the mask and configured to charge the battery using energy generated from exhaled breath of the patient. In other embodiments, the air flow generator may be self-powered.

In some embodiments, the air flow generator may include a housing, a motor disposed in the housing, a turbine disposed in the housing and coupled with the motor, and a power source disposed in the housing and coupled with the motor. The housing may include an outflow port for connecting with the tube, a relief valve, and an air intake aperture. The power source, for example, may include a battery. In some embodiments, the housing may have a diameter of no more than about 4 cm and a length of no more than about 17 cm. Generally, in one embodiment, the air flow generator may weigh no more than about 1.5 pounds. The tube, in various embodiments, may have an outer diameter of no more than about 1.5 cm.

In some embodiments, the system may further include a sensor for sensing the occurrence of the apnea episode. Such embodiments may optionally further include a processor for processing sensed data from the sensor and providing a signal to the air flow generator to generate a higher flow rate than the relatively low flow rate. The sensor, for example, may be a pulse oximeter and/or an airflow rate sensor.

In another aspect of the present invention, a device for treating a patient suffering from obstructive sleep apnea or snoring may include: a mask having a contact surface for forming a seal between the mask and the patient's face such that the mask surrounds at least the patient's nostrils; an air flow generator attached to the mask and configured to generate air flow at a relatively low flow rate; a one-way, variable resistance expiration valve in the mask to allow exhaled air to exit the mask during exhalation; and an air flow generator valve in the mask to allow air from the air flow generator to enter the mask during inspiration. Again, the expiration valve may provide less resistance to expired air during an early portion of expiration than during a later portion of expiration. Optionally, the mask may cover the patient's nostrils and mouth.

In another aspect of the present invention, a method for treating a patient suffering from obstructive sleep apnea or snoring may involve providing a first amount of resistance to expiration during an early portion of an expiratory phase of breathing and providing a second, greater amount of resistance to expiration during a later portion of the expiratory phase. In one embodiment, providing the first and second amounts of resistance may involve providing a first amount of positive airflow into an airway of the patient during the early portion and providing a second, greater amount of positive airflow into the airway during the later portion.

In an alternative embodiment, providing the first and second amounts of resistance may involve providing a mask that surrounds both nostrils of the patient's nose and providing a one-way, variable resistance expiration valve in the mask. In one embodiment, the mask may surround the patient's nostrils and the patient's mouth. The mask and valve may have any characteristics described above. In some embodiments, the method may further involve opening and closing the expiration valve using a controller coupled with the valve. In some embodiments, the method may further involve sending signals wirelessly to the controller.

In another aspect of the present invention, a method for treating a patient suffering from obstructive sleep apnea or snoring may involve: providing a mask configured to contact the patient's face to form a seal between the mask and the face such that the mask surrounds the patient's nostrils; providing air flow into the mask at a relatively constant flow rate of about 1-12 liters per minute and a pressure of about 2-15 cm H2O, using a portable air flow generator and a tube connecting the generator to the mask; providing resistance to expiration of air from the patient via a one-way expiration valve coupled with the mask or the tube, the expiration valve having an opening pressure of about 0 cm H2O to about 15 cm H2O; and allowing inhalation of atmospheric air into the mask through a one-way inhalation valve on the mask or the tube.

In some embodiments, the mask may be configured to form the seal via an adhesive strip on the mask configured to surround the patient's nostrils. In some embodiments, the mask may be further configured to surround the patient's mouth. In some embodiments, the mask may be configured to form the seal and maintain contact with the patient's face without requiring a strap.

Oftentimes, providing resistance to expiration may involve providing resistance throughout at least a majority of an expiratory phase of a breathing cycle. In some embodiments, providing resistance to expiration may involve providing a first amount of resistance during an early portion of the expiratory phase and providing a second, greater amount of resistance during a later portion of the expiratory phase. In some embodiments, providing the amounts of resistance may involve providing increasing amounts of resistance throughout the expiratory phase and closing the expiration valve at an end of the expiratory phase. In some embodiments, providing resistance to expiration may involve providing an increased resistance at an end of the expiratory phase. In some embodiments, the opening pressure is about 2-5 cm H2O.

Optionally, the method may further include providing air flow at a higher flow rate, compared to the relatively low flow rate, during or after an apnea episode. Such an embodiment may also further include detecting the apnea episode and switching the portable air flow generator from the relatively low flow rate to the higher flow rate, in response to the detected apnea episode. In some embodiments, providing the air flow at the higher flow rate may involve providing a pressure within a pharynx of the patient of approximately an opening pressure of the expiration valve.

Optionally, the method may further include powering the air flow generator via a battery. The method may further include collecting energy from exhaled breath of the patient, using an energy collection device coupled with the mask, and using the energy to charge the battery.

In another aspect of the present invention, a method for treating a patient suffering from obstructive sleep apnea or snoring may involve providing a first resistance to expired air at the beginning of an expiratory phase of a breathing cycle of the patient via a one-way, variable resistance expiration valve on a device coupled with the patient, and providing a second, greater resistance to expired air later in the expiratory phase via the expiration valve.

In some embodiments, the expiration valve may include an opening that automatically adjusts from a first diameter, in which the first resistance is provided, to a second, smaller diameter, in which the second resistance is provided. In some embodiments, providing the second resistance may involve closing the valve from a larger diameter to a smaller diameter. In some embodiments, the method may further involve providing positive air flow to the patient during inhalation. In some embodiments, the expiration valve may include multiple openings, and each opening automatically decreases in size to provide the second resistance.

Optionally, the method may further include sensing an apnea episode and providing the air flow at an increased flow rate in response to the sensed apnea episode. The device may include, for example, a mask secured over at least the patient's nose. In some embodiments, the mask may surround the patient's nostrils and mouth. In an alternative embodiment, the device may include a tube coupled with a mask secured over at least the patient's nose. In some embodiments, providing the first and second resistances may involve continuously closing the valve.

In another aspect of the present invention, a method for treating a patient suffering from obstructive sleep apnea or snoring may involve providing increasing resistance to air exhaled by the patient over the course of an expiratory phase of a breathing cycle via a variable airflow resistance device coupled with the patient to cover at least part of the patient's nose. In one embodiment, providing the increasing resistance may involve providing an opening pressure upon commencement of the expiratory cycle of about 2-5 cm H2O. As discussed previously, in some embodiments, the variable airflow resistance device may include a one-way valve on a mask, and the mask may surrounds two nostrils and/or a mouth of the patient. In alternative embodiments, the variable airflow resistance device may be a one-way valve coupled with a tube, which is coupled with a mask that covers two nostrils of the patient's nose.

Some embodiments may optionally include providing positive air flow to the patient during inhalation and/or exhalation. In some embodiments, the airway resistance device may include a one-way valve having multiple openings, and wherein each opening automatically decreases in size during the expiratory phase to provide the second resistance. In some embodiments, the airway resistance device may include a one-way valve, and providing the increasing resistance may involve allowing the valve to automatically close in response to decreased flow of exhaled air from the patient. In some embodiments, the airway resistance device may include a one-way valve, and providing the increasing resistance may involve continuously closing the valve during the expiratory phase.

In another aspect of the present invention, a device for treating a respiratory disorder such as sleep apnea or snoring may include a nasal covering body for covering at least one nostril of a nose of a human and an airflow resistor on the nasal covering body configured to inhibit exhalation through the nostril more than inhalation through the nostril. The airflow resistor may provide increasing resistance during an expiratory phase of a breathing cycle.

In some embodiments, the airflow resistor may include a one-way, variable resistance valve in the nasal covering body, where the valve is closed during inspiration, opens at a predetermined opening pressure during the initial portion of the expiratory phase, and closes during the expiratory phase to providing the increasing resistance. In some embodiments, the valve completely closes at an end of the expiratory phase, while in alternative embodiments, it may stay slightly open.

In some embodiments, the nasal covering body covers both nostrils of the nose. In some embodiments, the nasal covering body may include a mask configured to surround both nostrils and at least a portion of the nose. In some embodiments, the mask may further surround a mouth of the human. In some embodiments, the mask may further include an adhesive surface for adhering to the nose. In some embodiments, the mask may include a custom made mask configured to conform to a shape of the human's nose. In some embodiments, the mask is configured to adhere to the nose without requiring a strap attached to the human's head. In some embodiments, the airflow resistor may include one resistor for each nostril. In some embodiments, the airflow resistor may include more than two resistors. In some embodiments, the mask may be configured to attach to a conventional CPAP system. In alternative embodiments, the mask may be configured to attach to a small diameter, low flow, airflow tube.

In another aspect of the present invention, a method for treating a patient suffering from obstructive sleep apnea or snoring may involve: providing a nasal mask to be worn by the patient over the patient's nose, where the nasal mask is configured to remain coupled over the patient's nose without requiring a strap around any portion of the patient's head; providing a first resistance to expired air at the beginning of an expiratory phase of a breathing cycle of the patient via a one-way, variable resistance, expiration valve on the mask or a tube coupled with the mask; and providing a second, greater resistance to expired air later in the expiratory phase via the expiration valve.

In some embodiments, the mask may be a custom made mask configured to conform to a shape of the patient's nose, and the method may further include forming the custom made mask in accordance with the shape. In some embodiments, the mask may include an adhesive surface for coupling with the patient's nose or face.

In another aspect of the present invention, a method for making a nasal mask for treating a patient suffering from obstructive sleep apnea or snoring, may involve assessing a shape of the patient's nose and/or an area of the patient's face surrounding the nose and making the nasal mask to conform to the patient's nose, based on the assessment of the shape. In some embodiments, assessing the shape of the patient's nose may involve acquiring a computed tomography scan of at least a portion of the patient's head. In some embodiments, making the mask may involve providing computed tomography data from the computed tomography scan to a manufacturing machine and using the manufacturing machine to make the mask, based on the computed tomography data. In alternative embodiments, assessing the shape of the patient's nose may involve attaching a trial nasal mask over the patient's nose. Assessing the shape of the patient's nose may involve attaching the mask in a first configuration over the patient's nose, and wherein making the nasal mask comprises altering the nasal mask into a second configuration to conform to the patient's nose.

In another aspect of the present invention, a method for treating a patient suffering from obstructive sleep apnea or snoring may involve increasing resistance to expiration during an expiratory phase of breathing, such that a pressure curve derived from the patient's breathing during expiration begins at a first, lower pressure and increases to at least a second, higher pressure. In some embodiments, providing the increasing resistance may involve providing continuously increasing resistance such that the pressure curve has a gradual upward slope. In alternative embodiments, providing the increasing resistance may involve providing incrementally increasing resistance such that the pressure curve has a stepped upward slope.

These and other aspects and embodiments of the present invention are described further below in relation to the attached drawings.

BRIEF DESCRIPTION OF THE DRAWINGS

FIG. 3C is a perspective view of an OSA treatment system, according to another embodiment;

FIGS. 4A-4E are various views of a nasal mask for use with an OSA treatment system, according to one embodiment;

FIGS. 5A and 5B are diagrams demonstrating operation of multiple valves in a mask of an OSA treatment system, according to one embodiment;

FIG. 11A is a graph with an intranasal pressure curve demonstrating breathing mechanics with a positive airway pressure system and unobstructed breathing, according to one embodiment;

FIGS. 12A-12C are intra-nasal pressure vs. expiration curves for, respectively, a Provent® nasal insert, a conventional EPAP device, and a variable resistance expiratory resistance device according to one embodiment of the present invention;

FIGS. 16A and 16B are perspective views of a fluted-tube valve for providing variable resistance during expiration, according to one embodiment;

DETAILED DESCRIPTION

As discussed above in the Brief Summary, various embodiments described herein are directed to improved devices, systems and methods for treating obstructive sleep apnea (OSA) and/or snoring. In general, these embodiments seek to improve upon currently available CPAP systems and/or currently available expiratory flow resistor devices, such as the Provent® Sleep Apnea Therapy. In some embodiments, an improved mask alone may be provided, while in alternative embodiments a system including a mask, air flow generator, and possibly a tube for connecting the two, may be provided. Ideally, the embodiments described herein will effectively ameliorate sleep apnea or snoring with fewer side effects and less discomfort than CPAP or EPAP. In alternative embodiments, devices, systems and methods described herein may be used to treat other respiratory and/or pulmonary conditions, such as COPD or asthma. Thus, even though this description focuses on the treatment of OSA and/or snoring, the embodiments herein may be used in other treatments as well.

One way in which the embodiments herein may achieve the goals of improved therapy and reduced side effects is by reducing air leaks and patient discomfort with a face-conforming mask that does not require straps, thus allowing for lower airflow rates and pressures. Another improvement is a variable, one-way expiration valve that provides lower resistance to expiration at the start of expiration and increased resistance over the course of the expiratory phase of breathing. This valve reduces the discomfort felt in currently available expiration resistance devices that require a high opening pressure. It also helps maintain airway pressure during and at the end of expiration, in contrast to currently available valves that provide reduced resistance, and thus reduced pressure, as expiratory airflow decreases during the expiratory phase. These and other improvements are described in greater detail below.

Figure 1A:
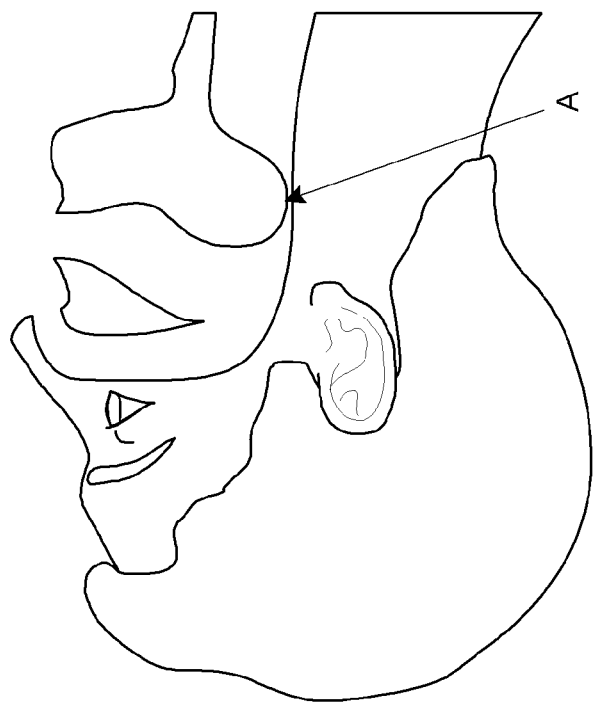
FIGS. 1A and 1B are side-view diagrams of a person's airway during normal breathing and during an episode of obstructive sleep apnea, respectively.
Figure 1B:
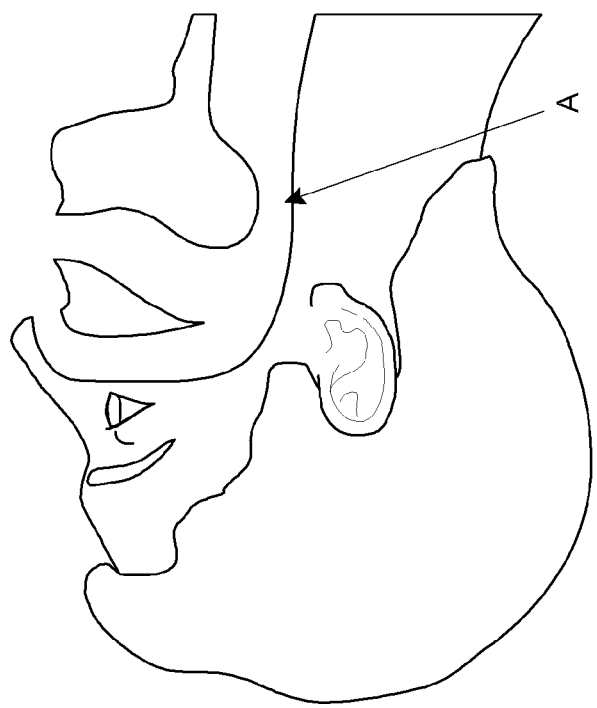
Figure 2:
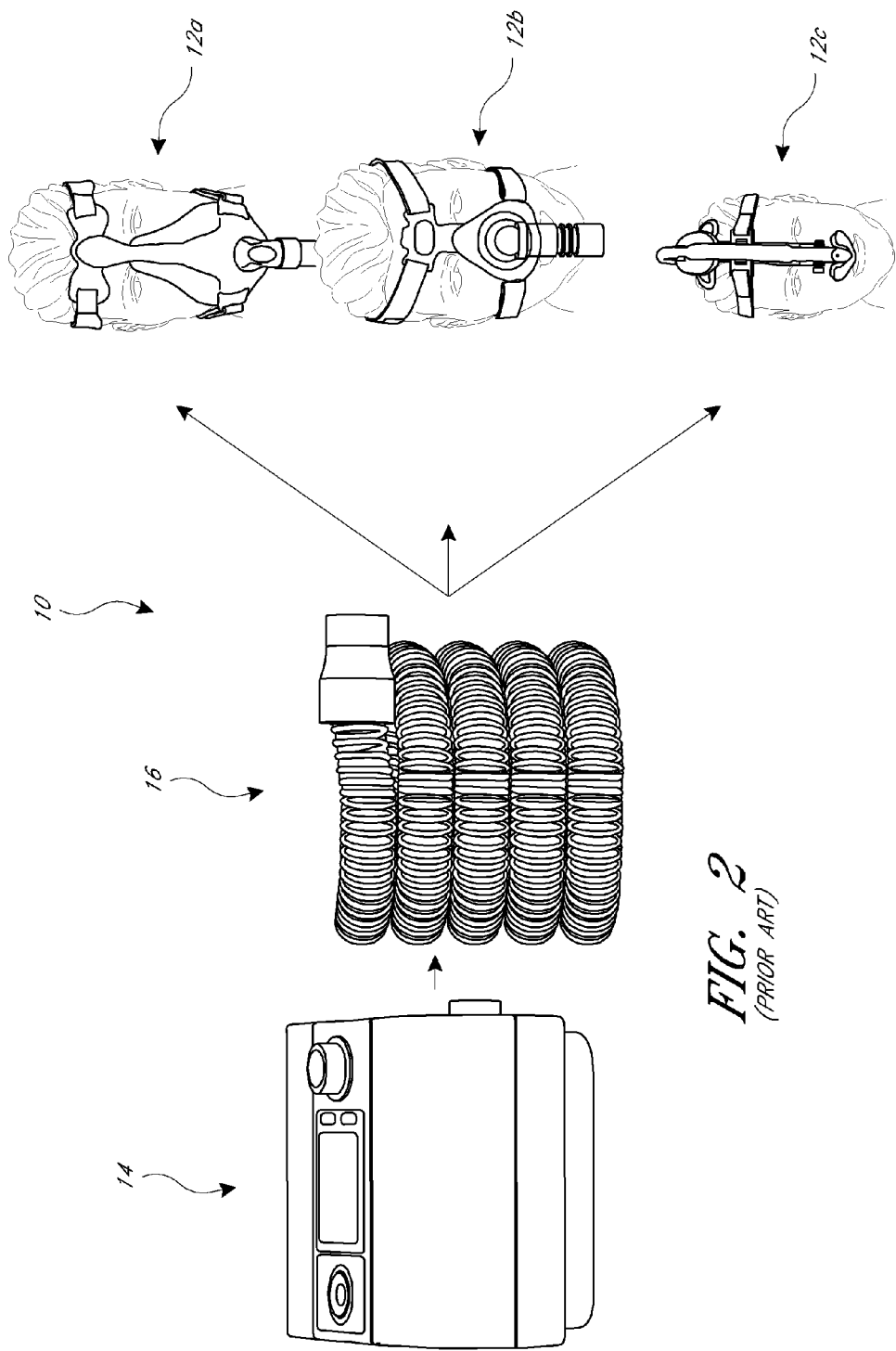
FIG. 2 is a perspective view of a conventional, prior art CPAP system.
Figure 3A:
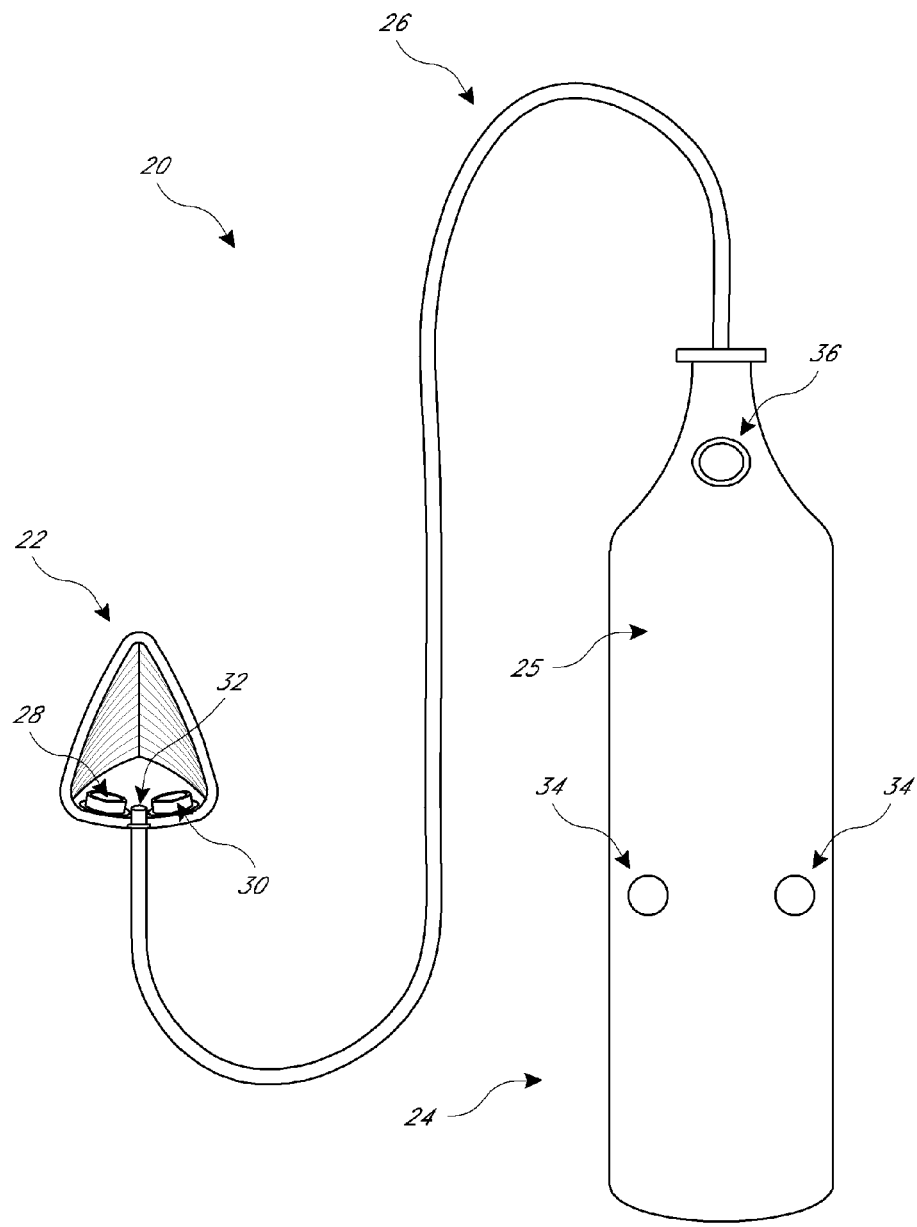
FIG. 3A is a perspective view of an OSA treatment system, according to one embodiment.

Referring now to FIG. 3A, in one embodiment, a system 20 for treating a patient suffering from OSA may include a mask 22, a portable air flow generator 24 and a tube 26 (or "tubing," "connector," or other analogous term) that connects the two. The view in FIG. 3A shows the inside of mask 22, which includes an expiration valve 28 (which also may be called an "exhalation valve" or "expiratory valve"), an inspiration valve 30 (which also may be called an "inhalation valve" or "inspiratory valve"), and a port 32 for connecting tube 26 to mask 22.

In one embodiment, mask 22 is configured to fit snugly about the patient's nose and adheres to the patient's skin via an adhesive contact surface to form an airtight seal with the patient. Alternatively or additionally, mask 22 may be custom fitted to conform closely to the shape of a patient's nose. Mask 22 is generally configured to be lightweight, comfortable for the patient to wear, and airtight when adhered to the patient. The airtight seal prevents air leaks and thus obviates the need for the high flow rates generally associated with CPAP. In some embodiments, mask 22 may be configured to form an open space (or "dead space") between the mask and a wearer's face of less than or equal to about 10 milliliters and may have a contact surface that contacts the wearer's face of greater than or equal to about 5 square centimeters. Mask 22 may alternatively be made of a relatively soft material that moves in and out with breathing or a harder, less compliant material that resists movement with breathing. In various alternative embodiments, mask 22 may cover the nose and mouth of the patient and/or may be attached via other means, such as by an elastic strap. Ideally, however, mask 22 will fit on the patient without the need for a strap, thus improving comfort and compliance. Various features and alternative embodiments of mask 22 are described further below.

In other alternative embodiments, a mask may cover the nose and mouth and may also include an energy converter for converting energy from the exhaled breath of a patient into energy that may be used to power or recharge a battery of air flow generator 24. Energy from the patient's breath may come in the form of airflow (wind) energy, heat of the breath, or both. This breath energy may pass through one or more turbines in the mask to convert the breath energy into electrical energy, and the electrical energy may in turn be passed through wiring to air flow generator 24. This is one example of a way in which air flow generator 24 may be self-powered.

In various alternative embodiments, one or more components of system 20 may be moved or eliminated. For example, in one alternative embodiment, one or both of valves 28 and 30 may be located somewhere within system 20 other than on mask 22. For example, one or both valves 28, 30 may be coupled with tube 26 in embodiment. In another alternative embodiment, tube 26 may be eliminated, and a smaller air flow generator (not shown) may be attached directly to mask 22.

Air flow generator 24, according to one embodiment, may include a housing 25 having one or more air intake apertures 34 and one or more air release valves 36. Housing 25 typically holds an air flow generation device and a power source (not shown). Housing 25, and more generally air flow generator 24, are portable, in that they may be easily carried and manipulated by a patient. The term "portable" is not meant to designate any specific size or weight of the device, but instead is meant simply as a general descriptor of the device as being more lightweight and smaller than a typical CPAP air flow generator. In one embodiment, housing 25 may have a diameter of no more than about 4 cm, a length of no more than about 17 cm, and a weight of no more than about 1 pound. In one embodiment, air flow generator 24 as a whole, including housing 25 and its contents, may have a weight of no more than about 1.5 pounds. Generally, air flow generator 24 may be smaller and lighter weight than a typical CPAP air flow generator, largely due to the fact that system 20 requires lower air flow rates than a typical CPAP system. Air flow generator 24 and its various features are described in further detail below.

Tube 26 is configured to be a small, lightweight, flexible connector that generally does not interfere with patient sleeping or comfort. Again, due to the low air flow rate required by system 20, tube 26 may have a significantly smaller diameter than tubing used in typical CPAP systems. For example, in one embodiment, tube 26 may have an outer diameter of no more than about 2 cm and preferably no more than about 0.6 cm. Tube 26 may be made of any flexible, durable material, such as but not limited to polymers, such as PTFE, PEBAX or the like. Tube 26 may also have a length that adds to ease of use and patient comfort. In some embodiments, a patient may be provided with multiple tubes 26 of different lengths to accommodate different placements of housing 25 on the body. For example, in one embodiment, housing 25 may be strapped onto one of the patient's arms, using a strap similar to those used for iPods. In another embodiment, housing 25 may be clipped to the patient's clothing, such as a shirt or waist band. In yet other embodiments, housing 25 may be placed on a nightstand table while the patient is sleeping. Tube 26 may be provided with any suitable length to accommodate such uses of system 20.

Figure 3B:
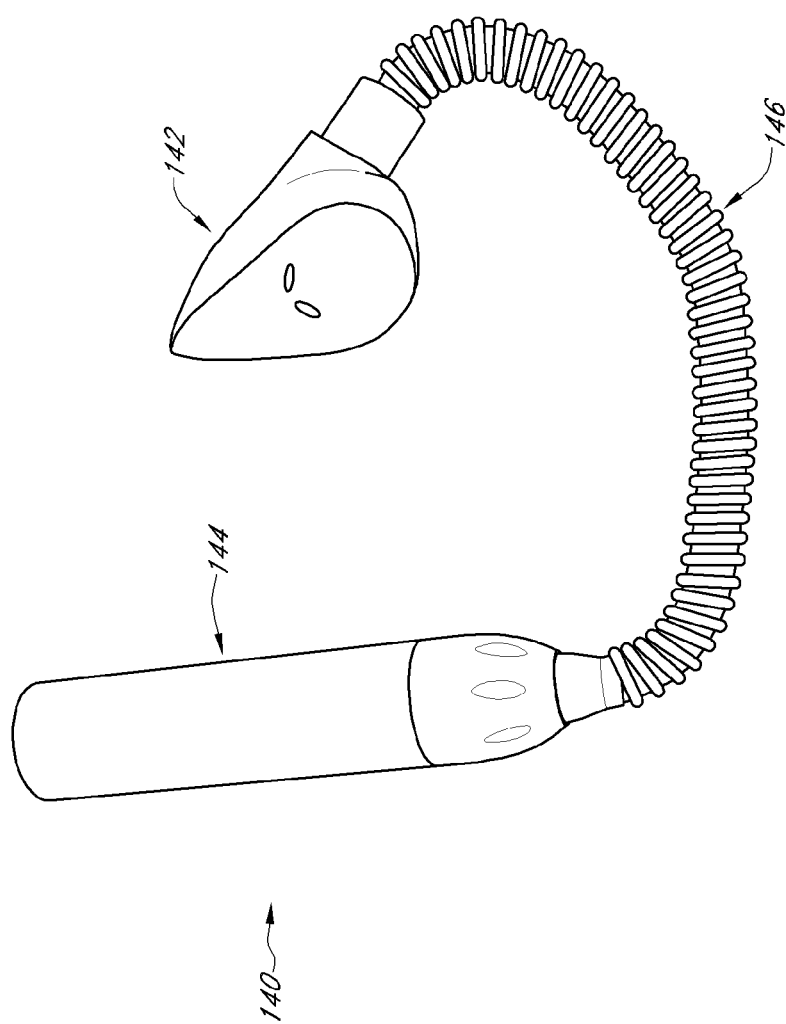
FIG. 3B is a perspective view of an OSA treatment system, according to another embodiment.

With reference now to FIG. 3B, another embodiment of a sleep apnea treatment system 140 is shown. Here, system 140 again includes a mask 142, air flow generator 144 and tube 146. Air flow generator 144 is the size and shape of an electric toothbrush handle, and mask 142 is custom formed to fit one patient's nose. This embodiment illustrates the small size that may be achieved in various embodiments.

FIG. 3C illustrates another embodiment of a sleep apnea treatment system 150. This embodiment includes a CPAP air flow generator 154 and standard CPAP tubing 156, coupled with an adapter/mask combination device 151 for providing improved sleep apnea therapy. Combined device 151 includes a mask 152, a one-way inspiratory valve 160, a one-way peak end expiratory valve 158 (or "PEEP valve"), and a flow restrictor 162 in line with tubing 156. Flow restrictor 162 may function to restrict the flow of air from the CPAP air flow generator to a specified flow rate that is lower than typically provided by CPAP. For example, while an unrestricted CPAP air flow generator may provide free flow at rates of 160-200 liters/minute, flow restrictor 162 may restrict this rate to about 10-40 liters/minute or less in one embodiment. In such an embodiment, generator pressure may be set to a level of about 7 cm H2O, and the PEEP valve 158 may be set to a pressure of about 5 cm H2O. Of course, these are only exemplary levels and may be set to other levels in alternative embodiments. This embodiment illustrates the fact that an improved device 151 may be provided, which may be used to optimize currently available CPAP systems. In other embodiments, a system including an air generator and tube may be provided, as shown in FIGS. 3A and 3B. The embodiment shown in FIG. 3C also illustrates the fact that valves 158, 160 need not be positioned on mask 152.

Referring now to FIGS. 4A-4E, mask 22 is described in further detail. According to one embodiment, mask 22 may include three one-way valves: expiration valve 28, inspiration valve 30 and air flow generator valve 36, which is disposed within port 32. Mask 22 is shaped to fit over the patient's nose such that a contact surface 38 contacts and forms a seal with the patient's skin. In some embodiments, contact surface 38 may include an adhesive. For example, as pictured in FIG. 4C, in some embodiments, a double-sided adhesive strip 39 may be attached to contact surface 38 to form the seal between mask 22 and the patient's skin. Adhesive strip 39 may be covered with a protective material, which may be removed by a patient/user immediately before use to expose adhesive strip 39. FIG. 4A is an internal/posterior view, FIG. 4B is a perspective view, FIG. 4D is a bottom view, and FIG. 4E is a side view of mask 22.

In general, mask 22 is designed to cover (or "surround") both of a patient's nostrils and most, or all, of a patient's nose. In the embodiment shown, for example, mask 22 is configured to surround a patient's nose and adhere to the patient's face around the nose via contact surface 38 and adhesive strip 39. In embodiments like this one, mask 22 may come in a variety of sizes (small, medium and large, for example), and may be made of plastic of sufficient strength to maintain its shape during breathing without collapsing. Mask 22 is typically configured to adhere to the patient's face/nose without requiring a strap. In other embodiments, mask 22 may be made larger to cover the mouth as well. In still other alternative embodiments, mask 22 may be smaller. For example, in one embodiment, mask 22 may include an adhesive strip that is applied over the nostrils and is coupled with one, two or three valves 28, 30, 36. In another embodiment, it may be possible to cover only one nostril.

In alternative embodiments, which are not shown, a mask may cover a patient's nose and mouth or only the patient's mouth. Although these alternative embodiments are not described in detail, the features of nasal mask 22 described herein may be equally applied to any such alternative embodiments. In particular, a mask that covers a patient's nose and mouth may be beneficial for patients who might convert to mouth breathing if only their noses are covered. In some embodiments, therefore, an OSA or snoring treatment system may include both a nasal mask and a nose/mouth mask, so that a patient can choose one or the other depending on symptoms and success with the nasal mask. In other embodiments, a physician may select a mask based on an individual patient's needs. Whichever mask is provided in a given system, any and all mask features described herein may be included, regardless of whether the mask covers only the nose or the nose and mouth.

In yet other embodiments, mask 22 may be custom manufactured to conform to a particular patient's nose/face shape. In one embodiment, for example, mask 22 may come in a first configuration, which may be placed over a patient's nose, and then treated in some way to assume a second configuration that conforms to the patient's nose shape. For example, mask 22 may be molded to conform to the patient's face, may be treated with mild heat, may be placed under vacuum and/or the like to assume the second configuration. In another embodiment, a computed tomography (CT) scan of the patient's head (or portion of the head) may be taken, and the CT data from the scan may be used to design a custom fitting mask 22. In one embodiment, for example, CT scan data can be used to generate a negative image of the patient's face, from which a mold may be generated, and the mold may be used to form mask 22. In various embodiments, any suitable method of custom building devices or parts may be used to form mask 22.

FIGS. 5A and 5B provide a diagrammatic illustration of the working of valves 28, 30, 36 of system 20. According to various embodiments, valves may be any of a number of different types of valves, such as but not limited to flap valves, hinge-less valves, balloon valves, stepper valves, ball valves, shape memory flap valves, membrane valves, iris valves, flute valves, slit valves or the like. Several examples of such valves are described in greater detail below, and FIGS. 5A and 5B are thus provided to illustrate the general principles of the workings of valves 28, 30, 36 in system 20. Also, as mentioned above, valves 28, 30, 36 may all be positioned on mask 22, as in FIGS. 4A-4E, or one or more valves may be positioned along or at one end of tube 156, as shown in FIG. 3C.

As illustrated in FIG. 5A, upon exhalation, air flow generator valve 36 and inspiration valve 30 close. The closing of air flow generator valve 36 prevents rebreathing of exhaled air upon inspiration. Expiration valve 28 is a one-way, variable resistance valve that will also remain closed until exhaled air generates a specified pressure within mask 22 (the "opening pressure"), at which point it will open to a first opening diameter (or opening configuration). For example, in various embodiments, the opening pressure for expiration valve 28 may be between about 0 cm H2O and about 25 cm H2O, and more preferably between about 0 cm H2O and about 12 cm H2O, and even more preferably between about 2 cm H2O and about 5 cm H2O. Expiration valve 28 is thus configured to open at an opening pressure that is less than the opening pressure of currently available expired air resistance devices, such as the Provent® device. This should provide improved patient comfort, because a device that requires a higher opening pressure is typically uncomfortable for a patient, as it is difficult to start exhaling. This difficulty in starting to exhale makes it feel difficult to breathe and produces a claustrophobic feeling. Expiration valve 28 provides resistance to exhaled air and thus provides positive end-expiratory pressure ("PEEP") and/or expiratory positive airway pressure ("EPAP"). Both PEEP and EPAP help keep an airway open during the breathing cycle and thus help prevent OSA.

In some embodiments, once expiration valve 28 opens at the opening pressure, it then begins to close as exhaled air flow decreases. In other words, during the expiratory phase of breathing with this type of expiration valve 28, resistance increases as flow decreases. This increased resistance provides increasing intra-airway pressure (or at least stable intra-airway pressure) during the expiratory phase of breathing, thus helping to keep the airway open during the later portion of the expiratory phase and at the end of expiration as the body prepares to transition to inhalation. This increased resistance to exhalation during the expiratory phase is exactly the opposite of what occurs with currently available PEEP or EPAP valves, where resistance and pressure decrease during expiration, thus providing less of a pneumatic splint at end-expiration. Therefore, expiration valve 28 may be advantageous relative to currently available valves that have only an open configuration and a closed configuration, because the increased resistance in response to decreased flow helps maintain the pneumatic splint throughout the expiratory phase. This advantage is described in further detail below in relation to several exemplary expiratory phase pressure curves.

In various alternative embodiments, expiration valve 28 may open at a predetermined opening pressure and may then either gradually/continuously close during the expiratory phase or may incrementally close during the expiratory phase. In other words, the valve may transition gradually from open to closed or may move in one or more increments. As will be described in greater detail below, in some embodiments, valve 28 may open and close in response to the breath, while in other embodiments, valve 28 may be driven open and closed by a timed mechanism. This mechanism may be timed according to the patient's breath or other physiological signals or may be pre-programmed at a desired timing, based on a desired or estimated breath pattern. In some embodiments, once valve 28 opens at the initial opening pressure, it may be able to open further, if expiratory flow initially increases during expiration. Valve 28 would then begin to close after achieving whatever is its most open configuration.

In some embodiments, the opening pressure for expiration valve 28 may be set at a desired pressure and not changed. Alternatively, in some embodiments the opening pressure may be adjustable. For example, the opening pressure may be adjusted by a physician and/or by a patient/user. This may enhance compliance, for example, since some patients may find a certain opening pressure uncomfortable and want less opening resistance, while others may want a higher resistance to increase the force of their pneumatic splint. In some embodiments, additionally or alternatively, the opening pressure may be controlled electrically or magnetically to deliver intermittent or variable opening pressure. The combination of the opening pressure required to open expiration valve 28 and the closure of air flow generator valve 36 and inspiration valve 30 upon exhalation provide an expiratory back pressure that creates the pneumatic splint to help keep the patient's airway open and prevent apnea episodes. Because expiration valve 28 opens to a variable degree depending on the amount of air flow during exhalation, expiration valve 28 thus provides variable resistance during exhalation, which produces improved pneumatic splinting and ease of breathing as compared to a valve that simply opens all the way at one pressure and closes at another pressure.

Referring now to FIG. 5B, at the end of expiration, expiration valve 28 closes, and air flow generator valve 36 and inspiration valve 30 open to allow pressurized air (from air flow generator 24) and room air to flow into mask 22. This pressurized air feature does not exist with devices that simply provide resistance to expiration. In an alternative embodiment, inspiration valve 30 may be eliminated, and all inspired air may be provided through air flow generator valve 36. It may be advantageous, however, to allow a user to inhale room air as well as pressurized air provided by air flow generator 24. In yet another alternative embodiment, inspiration valve 30 and expiration valve 28 may be combined into one valve that provides resistance to expired air and less or no resistance to inspired air.

Pressurized air provided through air flow generator valve 36 is typically provided at a relatively low flow rate, compared to conventional CPAP systems. In one embodiment, this low flow rate air is provided consistently throughout the breathing cycle, without any changes based on the patient's condition. In an alternative embodiment, if the patient becomes apneic (experiences an apnea episode) at end expiration, system 20 may switch from the relatively low flow rate to a higher flow rate, to pressurize the nasopharynx in a manner similar to CPAP. In such an embodiment, one or more sensors are incorporated into or used with system 20, such as but not limited to a conventional apnea monitor or a pulse oximeter. This sensing/switching feature is optional, however.

Finally, at the end of inspiration, air flow generator valve 36 and inspiration valve 30 close, and the expiratory phase of the breathing cycle starts again. Valves 28, 30, 36 thus move again into the configuration shown in FIG. 5A.

Figure 6B:
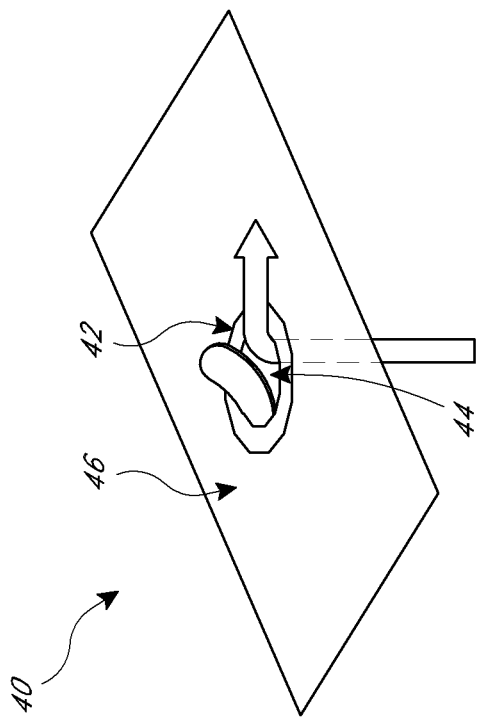
FIGS. 6A and 6B are perspective views of a Nitinol disc valve for use in a mask of an OSA treatment system, according to one embodiment.
Figure 6A:
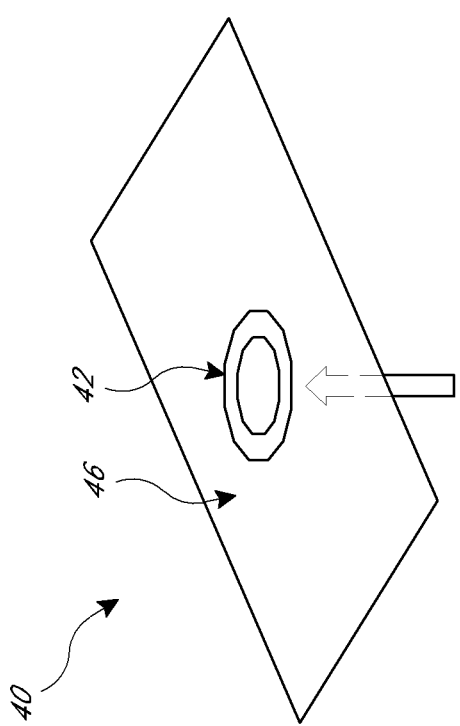

With reference now to FIGS. 6A and 6B, one embodiment of an expiration valve 40 may be a disc valve made of a flexible material such as Nitinol. Valve 40 generally includes a substrate 46 with an aperture 44 and a plate 42 of flexible material, such as Nitinol in this embodiment, attached to substrate 46 in such a way that it covers aperture 44 and flexes to allow exhaled air (large arrow) to pass through aperture 44. FIG. 6A shows valve 40 closed, and FIG. 6B shows valve open. Nitinol, being a shape memory nickel-titanium alloy, flexes under the pressure of exhaled air to open valve 40 at a set opening pressure. Nitinol plate 42 then continues to flex further in response to increasing expired air flow to allow aperture 44 to grow in size, thus reducing resistance and maintaining airway pressure within a desired range. As air flow then decreases, Nitinol plate 42 resumes its earlier configuration to cover aperture 44 and close valve 40. In various embodiments, the opening pressure may be between about 3 cm H2O and about 12 cm H2O, and in one embodiment about 5 cm H2O. In alternative embodiments, the opening pressure may be outside this range. Also in alternative embodiments, shape memory materials other than Nitinol may be used for plate 42. The material and/or configuration of plate 42 may be selected to provide a desired opening pressure. For example, some properties that may affect opening pressure include thickness, alloy/material type, temperature of metal, strain properties of metal, lamination of the material, and the like.

Figure 6D:
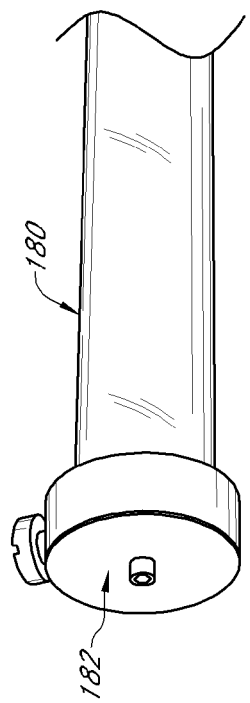
FIGS. 6C and 6D are perspective views of a Nitinol disc valve for use in a mask of an OSA treatment system, according to another embodiment.
Figure 6C:
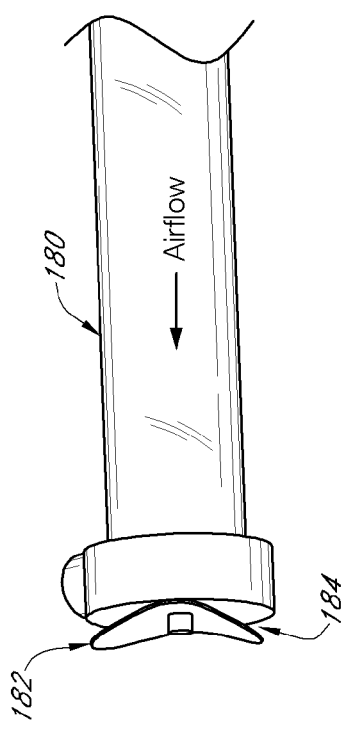

FIGS. 6C and 6D illustrate another example of a Nitinol flap valve 182, disposed at the end of a tube 180. When exhaled air moves through tube 180 with sufficient pressure, valve 182 flaps open to create an opening 184, as in FIG. 6C. As exhaled air flow decreases, opening 184 becomes smaller and finally closes, as in FIG. 6D.

Figure 7B:
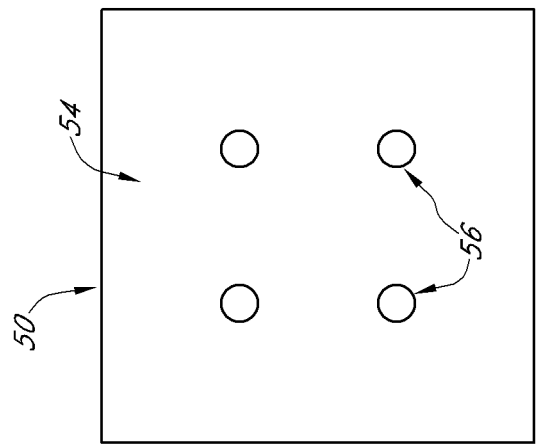
FIGS. 7A and 7B are diagrammatic frontal views of a flexible membrane valve for use in a mask of an OSA treatment system, according to one embodiment.
Figure 7A:
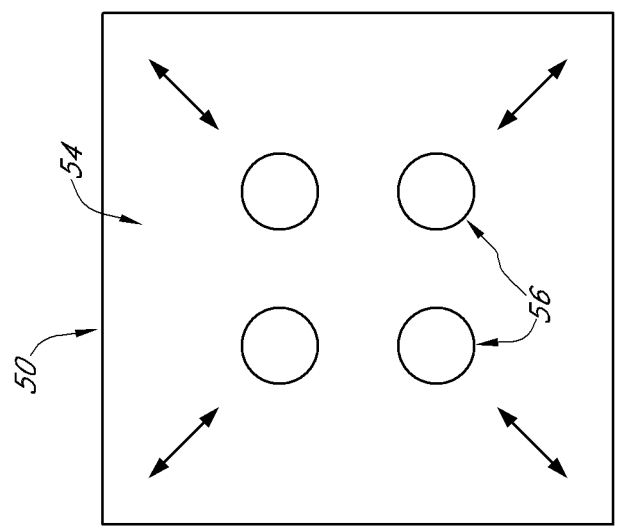

Referring now to FIGS. 7A and 7B, in another embodiment, an expiration valve 50 may include a flexible, expanding membrane 54. Expanding membrane 54 includes multiple small apertures 56, which remain closed until a specified opening exhalation pressure is reached. When opening pressure is reached, apertures 56 open to a first diameter, as illustrated by FIG. 7A. If expiratory pressure were to increase after opening pressure, apertures 56 would open further. Otherwise, apertures 56 generally decrease in size over the course of the expiratory phase as exhalation air flow decreases (FIG. 7B), thus increasing resistance and maintaining pressure within the pharynx/airway (the pneumatic splint).

As mentioned above, in alternative embodiments, an expiratory valve may provide resistance to expired air that increases over the course of the expiratory phase. Such valves may be configured, for example, to open a predetermined amount when the opening pressure is reached and then close slowly over the course of expiration. This increasing resistance may help augment the pneumatic splint and thus help keep the airway open during expiration. It may be achieved, for example, by a valve that "pops" open at a given expiratory opening pressure and then elastically closes back down over the course of expiration. Alternatively, such a valve may be programmed to open at an opening pressure and then close down during a certain amount of time. Additional alternative embodiments of valves are described further below.

Figure 8:
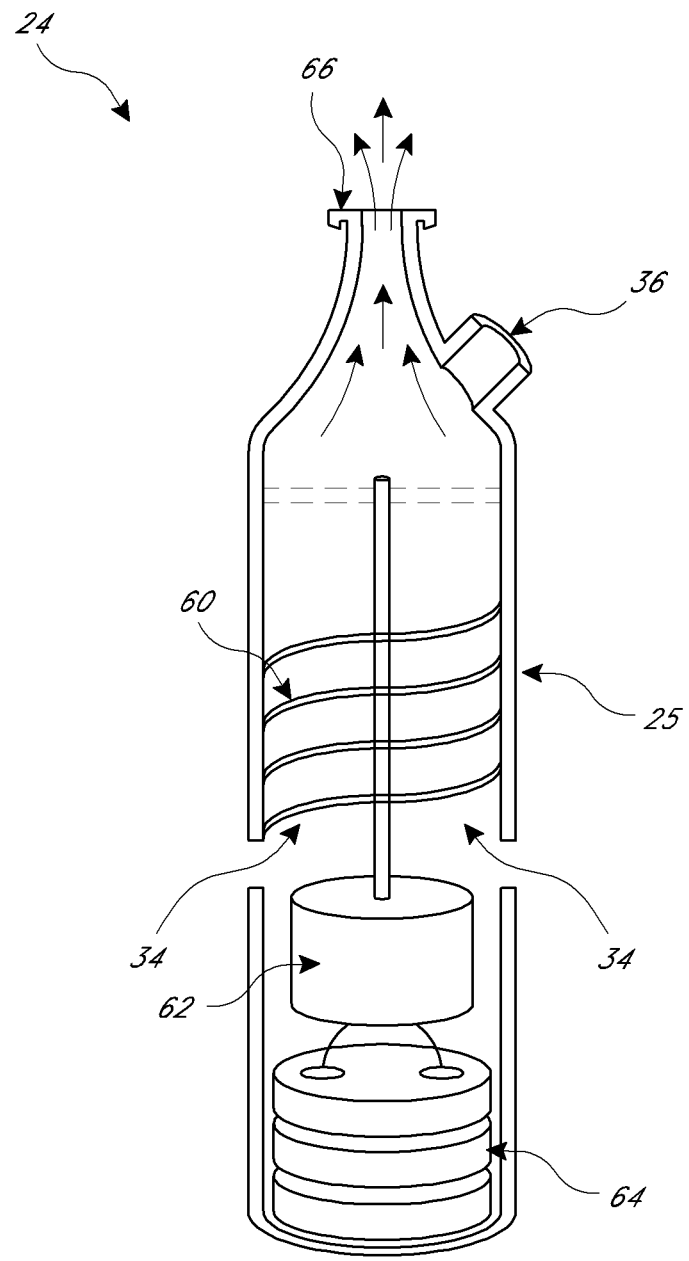
FIG. 8 is a cross-sectional view of a turbine air flow generator for use in an OSA treatment system, according to one embodiment.

Referring now to FIG. 8, because system 20 is configured to function at a lower air pressure and flow than traditional CPAP systems, there are a number of potential embodiments for an air flow generator to work with system 20. For example, in various embodiments, system 20 may include an air generator such as but not limited to a lithium powered turbine pump, a self-powered double bellows, a self-powered dual counter turbine or a self-powered air compressor and return. Any of these generators may be made significantly smaller than the typical CPAP air flow generator, due to the lower flow rates used in system 20.

In the embodiment illustrated in FIG. 8, air flow generator 24 includes housing 25, air intake apertures 34 and relief valve 36, as previously mentioned. Housing 25 also includes an air outflow aperture 66. A turbine 60 resides inside housing 25, coupled with a motor 62, which is coupled with a lithium battery 64 (or other power source in alternative embodiments). In use, battery 64 powers motor 62, which drives turbine 60, which pulls air in through air intake apertures 34 and pumps air out through air outflow aperture 66. This form of turbine air flow generator 24 is efficient enough, and air flow rates required by system 20 are low enough, that housing 25 can be made quite small. For example, in one embodiment, housing 25 may have a largest diameter of no more than about 6 cm and preferably no more than about 4 cm, and a length of no more than about 20 cm and preferably no more than about 17 cm. Additionally, the overall weight of air flow generator 24 may be about 1.5 pounds or less. Thus, size of air flow generator 24 may be comparable to that of a cell phone or electric toothbrush. This is significantly smaller than the typical CPAP air flow generator, which weighs approximately five pounds and measures approximately 10" by 8" by 6".

According to one embodiment, air flow generator 24 may provide an approximately constant air flow in a range of between about 1 liter per minute and about 15 liters per minute. This is significantly lower that the flow rates used in CPAP, which operate at flow rates as high as 200 liters of air per minute. Thus, a "low flow rate" for system 20 generally refers to a rate closer to the low end of the range of about 1-15 liters per minute, and a "high flow rate" for system 20 generally refers to a rate closer to the high end of the range of about 1-15 liters per minute. Thus, a "high flow rate" for system 20 is still typically lower than the flow rates used in CPAP. In some embodiments, air flow generator 24 may also sometimes operate at a flow rate below 1 liter per minute or may even provide no flow if a patient is breathing normally. Also in some embodiments, air flow generator 24 may provide air flow rates higher than 15 liters per minute, though generally flow rates will be lower than those used in CPAP.

The air pressure generated in air flow generator 24 is also typically less than the pressure required by a conventional CPAP machine. While conventional CPAP typically operates at about 4-20 cm of water, system 20 generally operates at the low end of a range of about 4-14 cm of water.

Relief valve 36 may be configured to open at a certain opening pressure to allow air to escape from housing 25, so that the air pressure delivered to mask 22 is not higher than desired. For example, in various embodiments, relief valve 36 may be set to open at a pressure of between about 10 cm H2O and about 15 cm H2O. In alternative embodiments, the opening pressure of relief valve 36 may be outside this range.

In an alternative embodiment, air flow generator 24 may be configured to provide variable flow rates. In some embodiments, flow rates may be adjusted based on sensed data from a patient. For example, if a patient experiences an apnea episode, an apnea monitor attached to the patient may detect the episode and send a signal to air flow generator 24 to switch from its usual low air flow rate to a higher air flow rate. Such an embodiment may also optionally be capable of shutting off completely if the patient is breathing normally without requiring positive pressure/flow during inhalation. In such an embodiment, system 20 may include an apnea monitor or other sensor and a processor for receiving and processing signals to instruct air flow generator 24. The advantage of such a system 20 is that it provides for variable flow rates. An air flow generator 24 designed to provide a constant, low flow rate, however, allows for a simpler system 20, without sensors/monitors or processors. Such a system 20 may be smaller, less cumbersome and require less power. In addition, because the air flow rates of system 20 are so much smaller than those of conventional CPAP, positively directed, continuous airflow should not be uncomfortable for a patient.

In other alternative embodiments, any of a number of different air flow generators may be used. These may include, but are not limited to, a self-powered double bellows, a self-powered dual counter turbine and/or a self-powered air compressor and return.

FIGS. 9-14 graphically illustrate breathing curves for different therapeutic devices and physiologic states. The normal resting breathing cycle is characterized by a rhythmic pattern of inspiration and expiration often with a pause at the end of expiration. Inspiration and expiration are often of relatively equal length (2-4 sec.) with a pause of shorter duration (1-2 sec.). As air moves through the nose and airway it encounters resistance due to natural narrowing of the passages. As such, pressure in the airway rises and falls during normal breathing.

Airway pressure is determined by a simple equation: $P = F \times R$, where F is airflow and R is resistance. Airflow (F) can be generated by the patient (inspiration and expiration) or by a machine such as a CPAP generator. Increasing airflow generally increases pressure (P) in a direct linear fashion. There is a natural resistance (R) in the nasal passages that causes moderate change in the airway pressure during normal respiration. Resistance can be increased naturally (e.g. stuffed nose) or by an external resistor. Increasing resistance generally increases pressure in a direct linear fashion.

Figure 9:
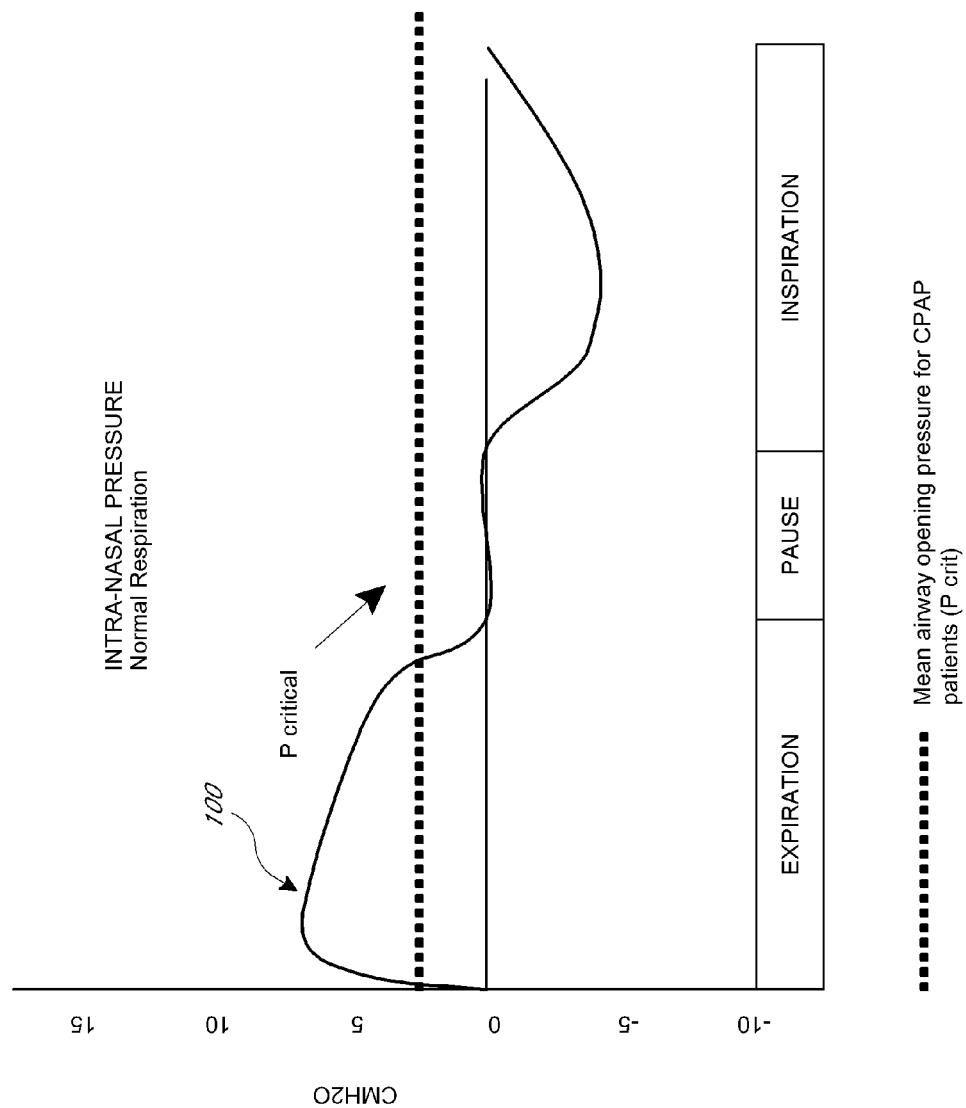
FIG. 9 is a graph with an intranasal pressure curve demonstrating normal respiratory mechanics.

Referring now to FIG. 9, an intranasal pressure curve 100 is shown for a complete, normal breathing cycle (expiration, end expiration pause, inspiration) in a person who does not have obstructive sleep apnea. The vertical axis shows intranasal pressure in cm H2O, and the horizontal axis represents one breath cycle, starting with the expiratory phase of breathing and ending at the end of the inspiratory phase. P critical is an approximated average pressure required to keep the airway open in OSA patients. The value for P critical varies from patient to patient, and thus is provided in these figures for exemplary purposes only.

In normal breathing without OSA, airway pressure is determined by expiratory flow and nasal resistance. Expiratory flow is variable and dependent on respiration, while nasal resistance is constant and independent of expiratory flow. The posterior pharynx stays open even at ambient air pressure (0 cm H2O) due to pharyngeal and glossal tone. In OSA patients, by contrast, the posterior pharynx becomes obstructed at end expiration as pharyngeal pressure drops below the critical pressure (P critical). In other words, such patients have insufficient PEEP (positive end expiratory pressure) and/or pharyngeal tone to keep their airways open. In experiments with OSA patients, the mean pressure required to partially open the airway is approximately 1 cm H20. A mean nasal pressure of about 11 cm H2O is required to fully eliminate obstructive resistance in the pharynx, but flow increases are linear above P critical.

Figure 10A:
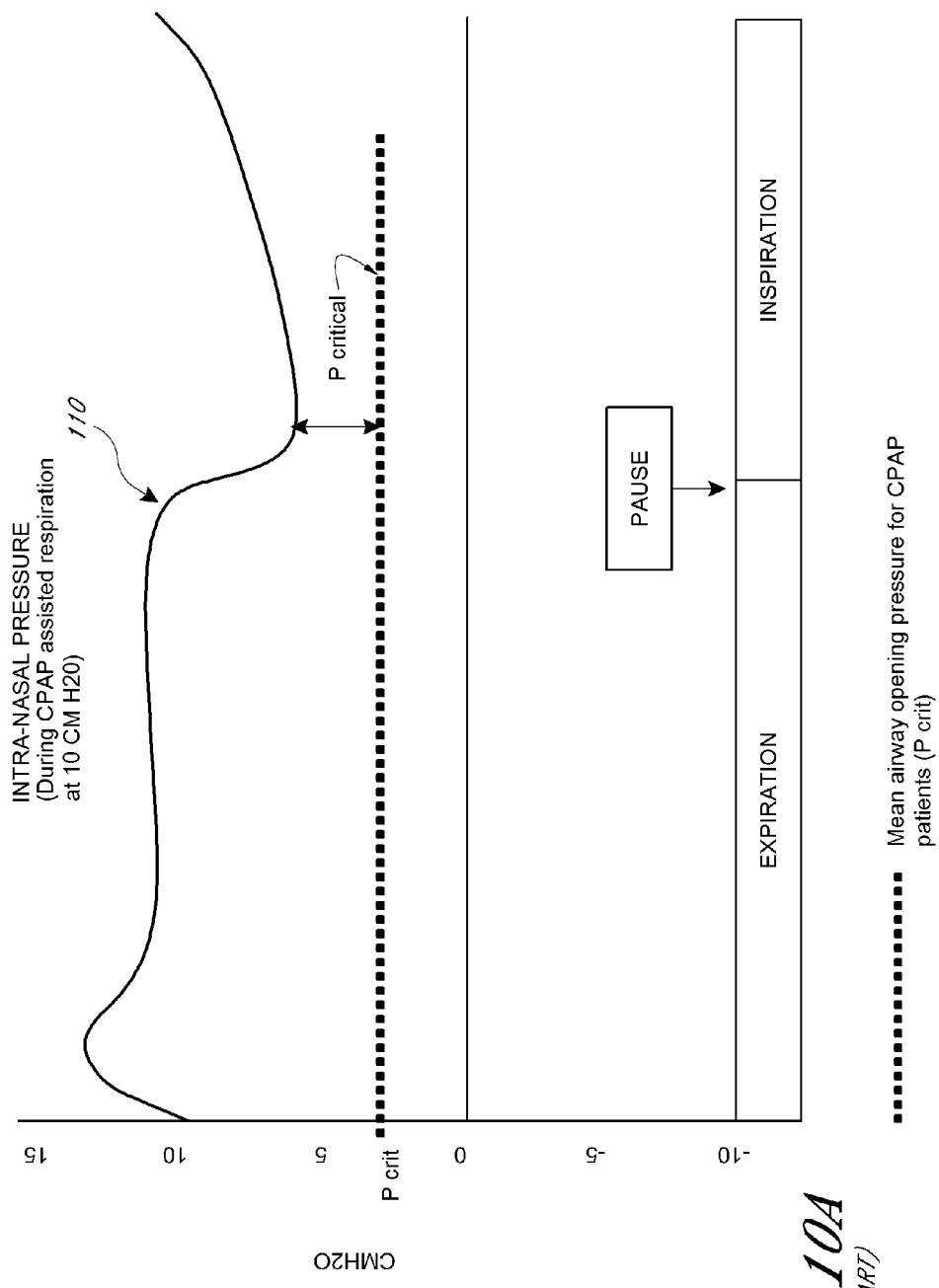
FIG. 10A is a graph with an intranasal pressure curve demonstrating breathing mechanics with OSA and conventional CPAP.

With reference to FIG. 10A, another intranasal pressure curve 110 is shown for a complete breathing cycle of a person using a CPAP system. CPAP works by keeping pharyngeal and nasal pressure above the critical pressure (P critical), as shown by curve 110, and thus preventing pharyngeal collapse. CPAP also slows expiration due to increased resistance caused by the restrictive nature of the mask and the high-rate inflow of air from the CPAP machine. This shortens the pause phase between expiration and inspiration.

With CPAP, resistance is determined by tubing and exit holes on the mask and remains relatively constant throughout the breathing cycle. Flow also remains constant because the CPAP system supplies a constant airflow to keep the pharynx open. Pressure is primarily related to the flow rate. As shown in FIG. 10A, a constant, high airflow rate increases pressure throughout the entire breathing cycle. Excess air flow is vented through holes on the CPAP mask which can lead to a frequent complaint of air blowing on the face. Excess air also circulates through the pharynx in a turbulent fashion which can lead to another frequent complaint of mucosal drying.

Shortcomings of CPAP include, however, discomfort due to the elevated expiratory resistance, air leaks from the CPAP mask that require high air flow rates to compensate, nasal dryness, ear pain, rhinitis, abdominal bloating and headaches that result from sinus pressure due to the required high flow rate. The high flow rate itself, which can be as high as 200 liters per minute in some cases, can be extremely uncomfortable, as a patient must exhale into what feels like a gale force wind being blown into his/her airway.

Figure 10B:
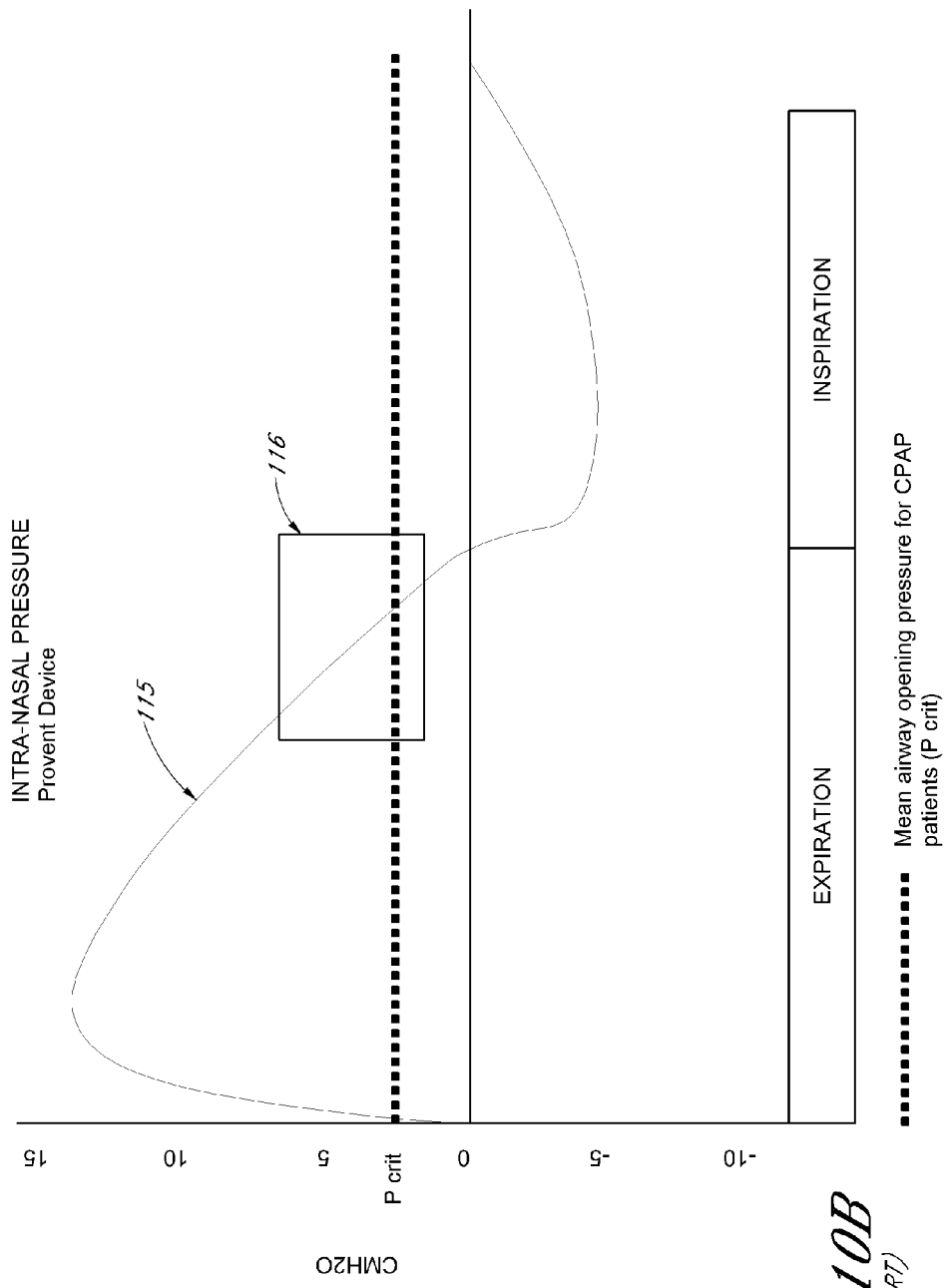
FIG. 10B is a graph with an intranasal pressure curve demonstrating breathing mechanics with OSA and a Provent® device.

Referring to FIG. 10B, another intranasal pressure curve 115 is shown, this time illustrating breathing mechanics of an OSA patient wearing a fixed orifice resistor EPAP device (e.g., Provent® Sleep Apnea Device (Ventus Inc.). The device uses one-way valves placed over each nostril to maintain constant resistance. Inspiration is minimally affected because the valves open when inhaling, but expiration is resisted because air must exit through small holes in the valve. This resistance to expiration raises intra-nasal pressure during expiration. In addition to maintaining a higher expiratory pressure, it is thought to work by slowing expiration to shorten the pause phase and thus lower the chance for airway collapse as well as to increase capillary pressure (auto-PEEP) leading to improved ventilation.

However, such a device has several drawbacks. First, intra-nasal pressure drops during expiration, because the valves of the device offer only fixed resistance. As flow decreases toward end expiration, pharyngeal pressure drops rapidly. This makes it difficult to maintain a therapeutic gap between P critical and end expiratory pressure. This is illustrated in FIG. 10B by the highlighted box 116. Within box 116, pharyngeal pressure can drop below P critical for long enough that collapse becomes more likely. In addition, if there is any pause between expiration and inspiration, intranasal pressure will drop to 0 cm H20, since there is no active PAP (positive airway pressure). This would lead to complete airway collapse in many OSA patients. Finally, with such a device, the patient must first generate relatively high pressure to start exhaling through the device. This high pressure can be very uncomfortable, as it may make patients feel like they cannot exhale. Thus, many physicians believe the Provent® device is useful only for patients with very mild OSA or in those cases only for patients who can tolerate the high opening pressure.

Figure 11B:
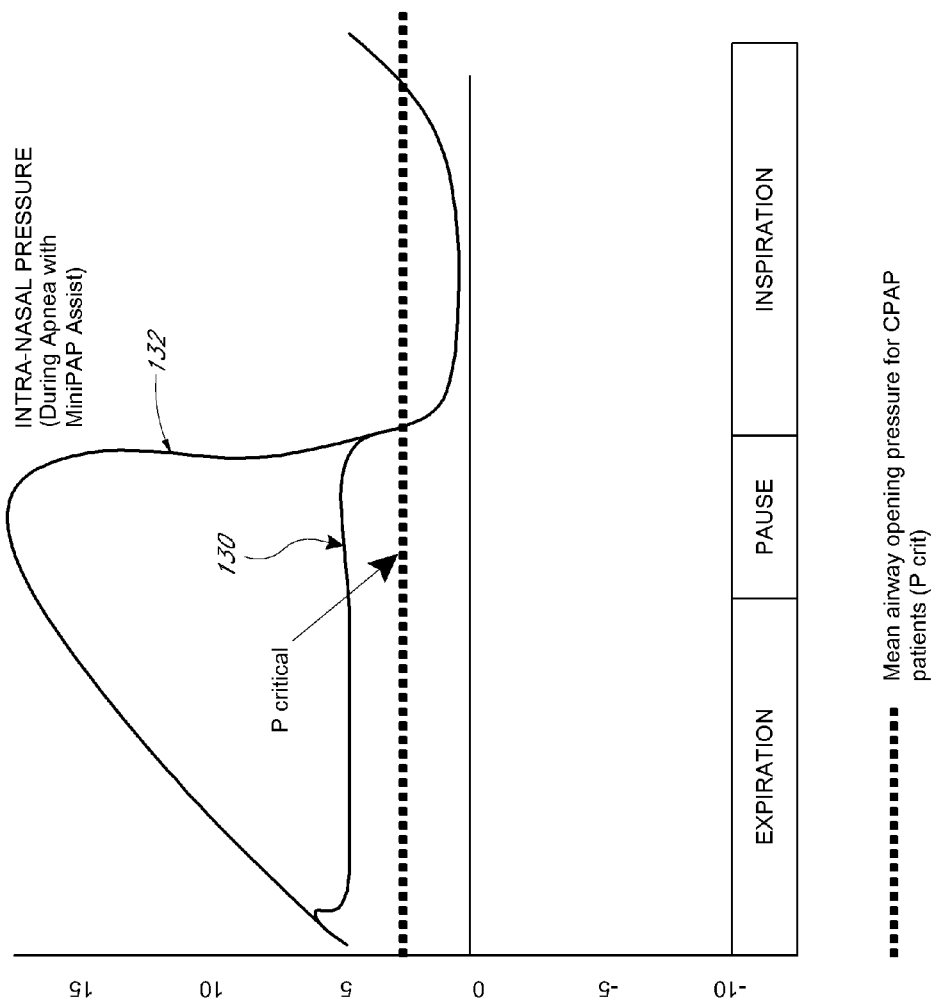
FIG. 11B is a graph with an intranasal pressure curve demonstrating breathing mechanics with a positive airway pressure system and apneic breathing, according to one embodiment.

Referring now to FIGS. 11A and 11B, various intranasal pressure curves 120, 122, 130, 132 are shown for breath cycles using the sleep apnea treatment system according to various embodiments described herein. Referring first to FIG. 11A, two alternative embodiments of curves 120, 122 for pressure vs. breath cycle are shown, each illustrating breathing assisted by a variable resistance, one-way expiration valve but without any positive airway pressure (PAP) coming from an air flow generator. Either curve 120, 122 may be used, in various embodiments, as well as any of a number of curves in between or approximately the same as those shown in FIG. 11A. Looking first at curve 120, in one embodiment, the initial opening pressure is less (about 5 cm H2O) than the opening pressure shown in FIG. 10B (about 15 cm H2O). In addition, intra-nasal pressure remains significantly above P critical throughout the expiratory phase and does not dip down until the very end of expiration/beginning of inspiration. This maintenance of airway pressure through the expiratory phase should help ameliorate OSA. In the embodiment illustrated by curve 120, intra-nasal pressure remains relatively constant throughout expiration. The expiratory valve thus increases resistance sufficient to maintain approximately the same pressure despite decrease expiratory air flow.

In another embodiment, illustrated by curve 122, the expiratory valve may increase resistance in such a way that intra-nasal pressure increases through the expiratory phase. This increasing pressure may work even more effectively to keep the airway open toward the end of the expiratory phase. Furthermore, an even lower opening pressure than shown by either curve 120 or curve 122, such as an opening pressure of between about 0 cm H2O and about 5 cm H2O, may provide enhanced patient comfort, since the patient will not have to struggle to start expiration. During the expiratory phase, intra-nasal pressure may be increased to any suitable level, such as about 15 cm H2O, between about 5 cm and about 15 cm H2O, or in some cases even above 15 cm H2O. Thus, the systems and devices described herein may generate a pressure vs. breath cycle curve that looks like either of curves 120, 122 or, alternatively, any of a number of suitable curves in between or approximately the same as those shown.

In FIG. 11B, pressure curves 130 and 132 illustrate a breathing cycles of two patients using two embodiments of the sleep apnea treatment system as described herein, during apneic breathing and with the air flow generator turned on. During an apnea episode (the "Pause" segment labeled at the bottom of the chart), the air flow generator maintains airway pressure. The air flow generator also augments airway pressure during inspiration. Pressure curve 132 illustrates an intra-nasal pressure that increases during expiration, as discussed above. The lower flow rates of the embodiments described herein, combined with the variable expiratory resistance provided by the expiration valve, helps provide many or all of the benefits of CPAP while reducing at least some of the side effects.

In one embodiment not yet described, a conventional newly invented PAP system may be programmed to provide a curve similar to the pressure vs. expiration curve 260, in FIG. 12C. In this embodiment, the PAP system could be programmed, such as with software, to provide an initial flow rate of positive air flow to the patient at the beginning and early portion of expiration and to increase the air flow rate during the later portion of expiration. Thus, a curve such as curve 260 may be provided, thus obviating at least some of the drawbacks of conventional CPAP. An air flow pattern of this type may be provided by timing the air flow rate changes according to an average breath cycle, or they may be customized for different patients.

Referring now to FIGS. 12A-12C, pressure vs. expiratory phase curves for various expiration resistance devices are compared. FIG. 12A illustrates an estimated Provent® pressure curve 240 of the intra-nasal pressure during exhalation while wearing the Provent® device. As already described, the Provent® pressure curve 240 spikes immediately, as the patient tries to overcome the high resistance of the fixed orifice valve. The curve then dips quickly during expiration, thus providing insufficient intra-nasal pressure at end expiration. FIG. 12B illustrates a conventional EPAP valve pressure curve 250. EPAP curve 250 also has a high opening pressure but one advantage of a mechanical EPAP valve is that expiratory pressure is more constant during the expiratory phase compared with a fixed orifice valve.

In contrast to the two prior art pressure curves 240 and 250, as shown by the variable resistance pressure curve 260 in FIG. 12C, the variable resistance, one-way valves described herein open at a much lower opening pressure and provide increasing resistance (and thus intra-nasal pressure) during the expiratory phase. This helps keep a patient's pharynx and airway open without the discomfort of a high opening pressure.

Figure 13:
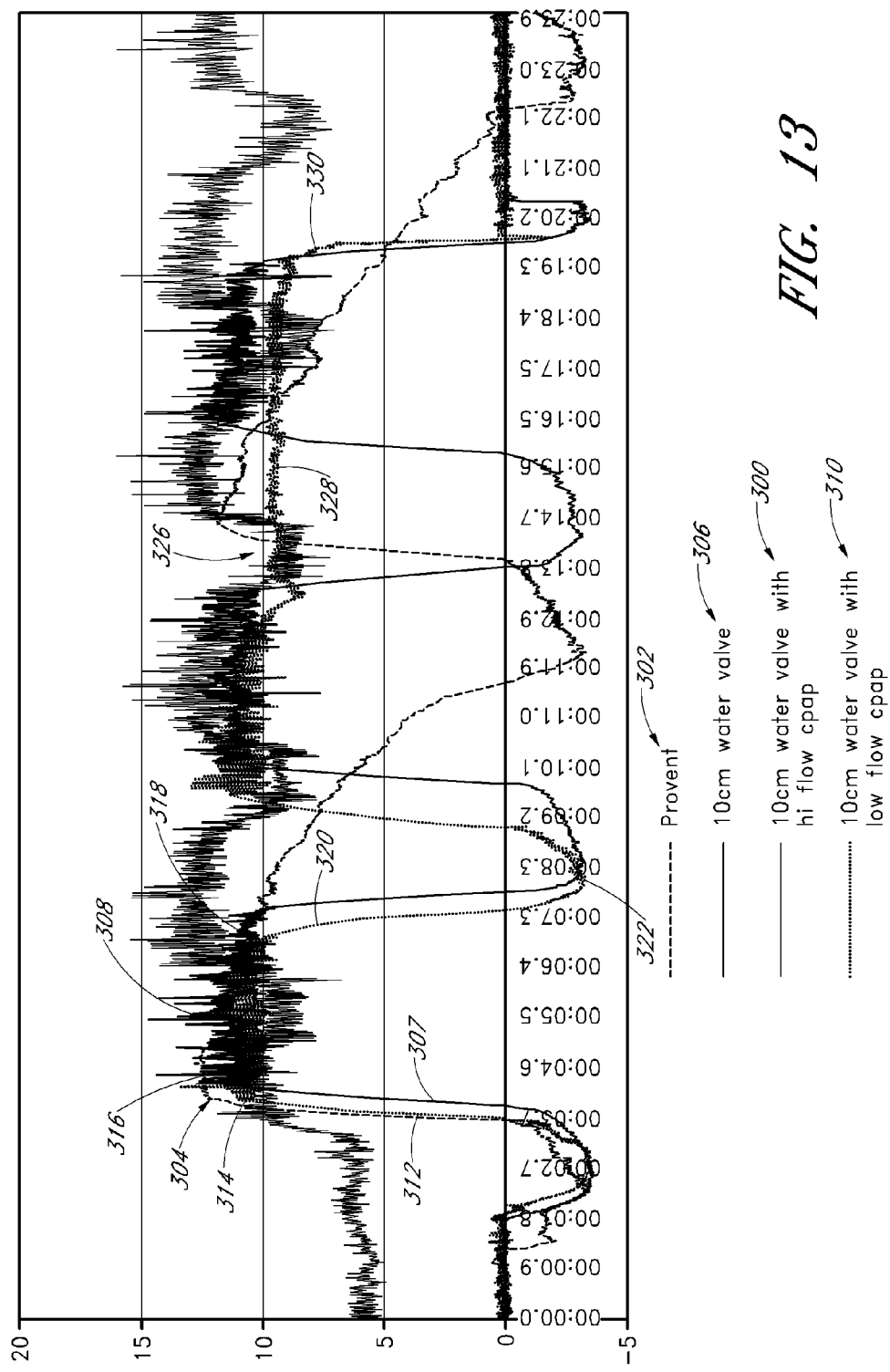
FIG. 13 is a graph comparing intranasal pressure curves for different devices including one embodiment of the present disclosure.
Figure 13A:
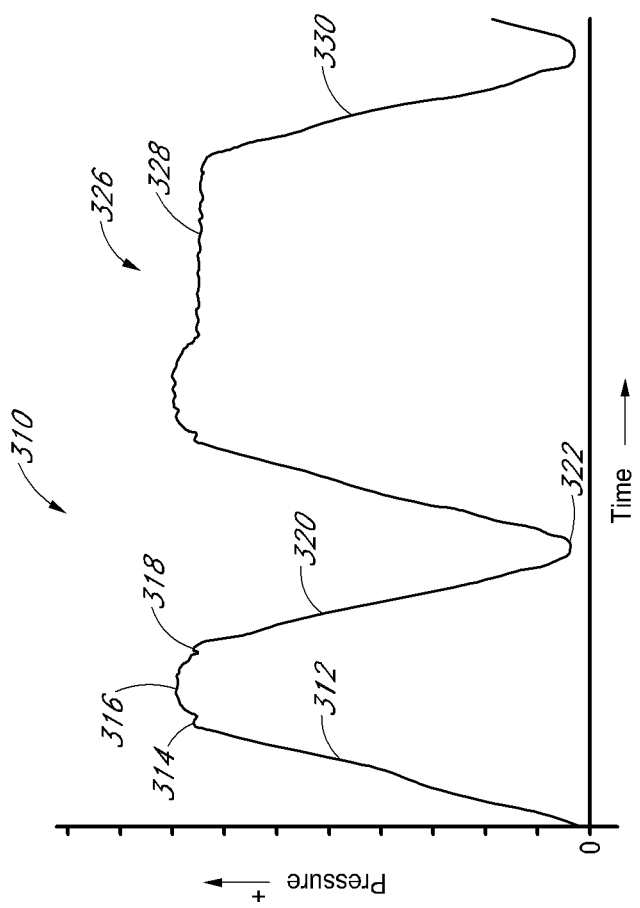
FIG. 13A illustrates the intranasal pressure curve demonstrating breathing mechanics according to the one embodiment shown in FIG. 13.

FIG. 13 compares respiratory curves for different sleep apnea devices. Specifically, FIG. 13 compares standard CPAP 300 and Provent® 302 with respiratory curves for some embodiments described herein 306, 310. FIG. 13A specifically illustrates the curve 310.

Figure 13B:
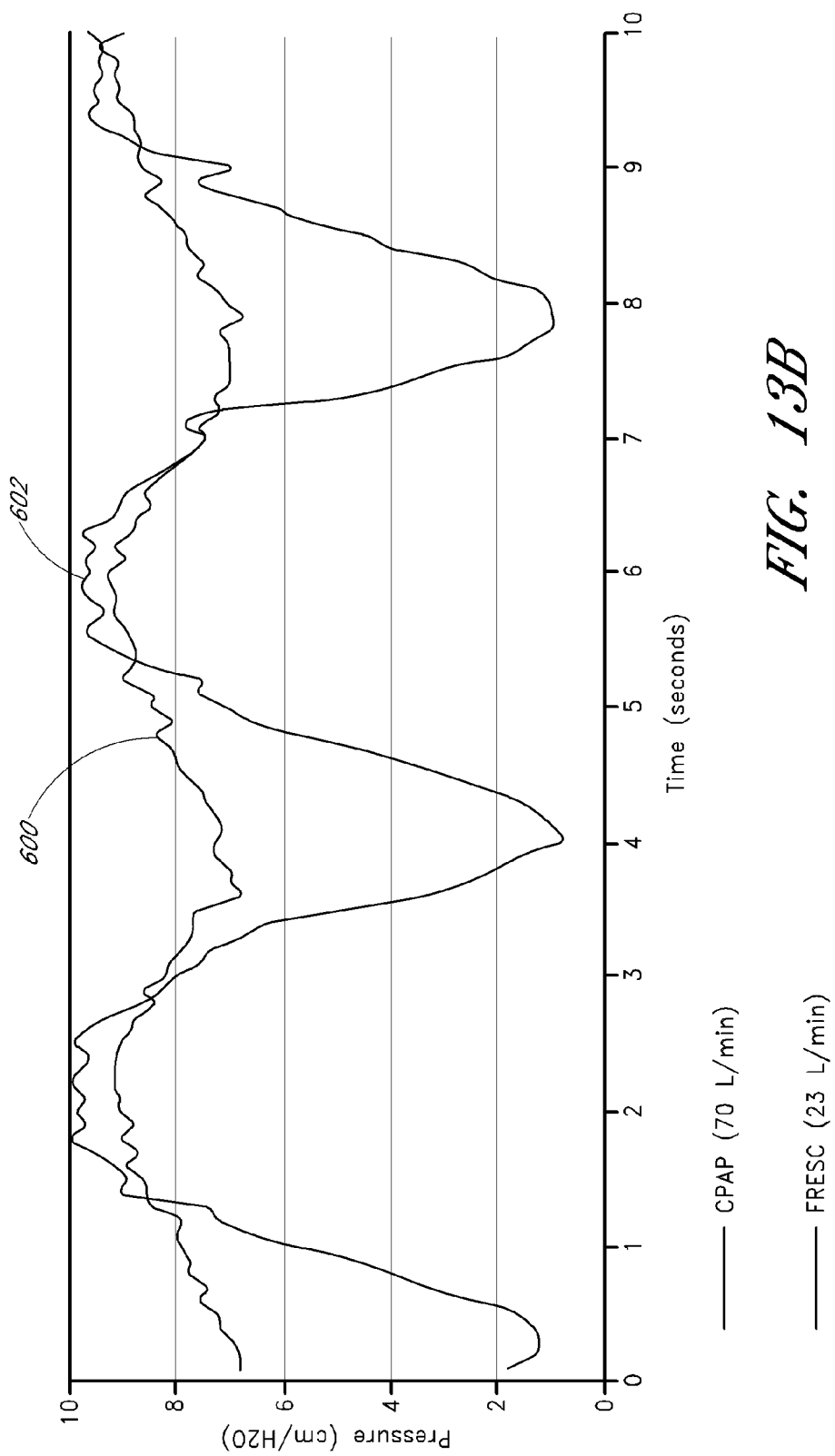
FIG. 13B is a graph comparing intranasal pressure curves for CPAP and the one embodiment shown in FIG. 13.

FIG. 13B is another graph comparing CPAP 600, and a curve 602 of an embodiment of a device 400 described herein with external airflow. The CPAP curve 600 can include features similar to the CPAP curve 300, while the curve 602 can include features similar to the curve 310. As described above, the CPAP curve 300 stays elevated during the breathing cycle because the airflow generator delivers air at high flow rates. The constant elevated pressure can make breathing generally difficult.

With Provent®, the respiratory curve 302 includes a sharp pressure transition 304 during the initial portion of exhalation because the Provent® device utilizes a fixed diameter hole to produce resistance. Accordingly, pressure is based primarily on the rate of exhalation. During initial expiration, the pressure starts at about 12 cmH2O and decreases gradually so that it is approximately 5 cmH20 near the end of expiration.

Curve 306 illustrates a respiratory curve for a device with an expiratory valve, as described herein, and no airflow generator. The expiratory valve can be configured to create pressure without external airflow. The expiratory valve used in curve 306 is configured to vary resistance and release pressure if the pressure exceeds a threshold pressure. As airflow increases, the expiratory valve can decrease resistance to keep pressure constant.

At the beginning of exhalation, the slope of the ramp 307 can be dependent on the force of exhalation. As expiratory force increases, the slope of the ramp 307 increases. However, above the threshold pressure, the valve can open and pressure can be controlled independent of flow. After the valve opens, the curve 306 can exhibit a plateau region 308. In the plateau region 308, the expiratory valve can maintain a generally constant pressure even as the rate of exhalation changes. The threshold pressure can be varied. In certain aspects, the pressure can remain generally constant and can be at least about 5 cmH20 and/or less than or equal to about 15 cmH20. In certain aspects, the pressure can remain generally constant, e.g., variation within a range of no more than about 4 cmH20, preferably no more than about 2 cmH20; in one implementation, between about 8 cmH20 and 12 cmH20 or within about 9 cmH20 and about 11 cmH20; and, in one embodiment, at about 10 cmH20.

In some embodiments, there is no external airflow. Without the external airflow, the breathing curve 306 can reach a minimum pressure that is lower than CPAP's minimum pressure. Accordingly, even without external airflow, the breathing curve 306 can better resemble a normal breathing curve. In certain aspects, the minimum pressure can be less than or equal to 5 cmH20, less than or equal to atmospheric pressure, or otherwise.

The curve 310 illustrates a respiratory curve for a device with an expiratory valve and an airflow generator supplying constant airflow. The expiratory valve can be configured to create pressure without external airflow. In certain aspect, the expiratory valve can be configured to open and release pressure if the pressure exceeds a threshold pressure. In certain aspects, the expiratory valve can vary resistance. In certain aspects, the resistance can be inversely dependent on flow. As airflow increases, resistance can decrease to keep pressure constant. In certain aspects, the expiratory valve can be a spring valve.

At the beginning of exhalation, the slope of the ramp 312 can be dependent on the rate of exhalation. The addition of air from the airflow generator can decrease the slope of the ramp 312 and create parabolic curve transitions 314, 318. In certain aspects, the change in pressure can be less than or equal to about 40 cmH20/sec, less than or equal to about 15 cmH20/sec, less than or equal to about 10 cmH20/sec, or otherwise. In effect, the airflow generator can make exhalation more comfortable.

In certain aspects, above a threshold pressure, the valve can open and pressure can be maintained independent of flow. After the valve opens, the curve 310 can exhibit a plateau region 316. In the plateau region 316, the pressure can remain generally constant even as the rate of exhalation changes. In certain aspects, the pressure can remain generally constant and can be at least about 5 cmH20 and/or less than or equal to about 15 cmH20. In certain aspects, the pressure can remain generally constant at about 10 cmH20. If the pressure were to exceed the threshold pressure, expiration could become difficult.

The combination of the expiratory valve and the airflow generator can influence the transition 320 from exhalation to inhalation. If pressure is kept elevated until the point when inhalation begins, it is less likely that the throat will collapse enough to obstruct inhalation. In certain aspects, the device can include a column of air that can help maintain airway pressure at a desired level at the critical time when the patient changes from expiration to inspiration. In certain aspects, as pressure decreases, the expiratory valve can gradually close to help maintain pressure. At the end of expiration, the expiratory valve can close completely.

In certain aspects, the pressure at the end of expiration is at least about 5 cmH20 and/or less than or equal to about 15 cmH20. In certain aspects, the pressure at the end of expiration is between about 9 cmH20 and about 11 cmH20, and in one embodiment, about 10 cmH20.

In certain aspects, the change in pressure can change from the pre-determined pressure to atmospheric pressure in less than about 1 second, less than about 0.5 seconds, or otherwise. In certain aspects, the pre-determined pressure can be at least about 5 cmH20 and/or less than or equal to about 15 cmH20. In certain aspects, the pre-determined pressure can be about 10 cmH20.

During inhalation, an inspiratory valve can open to allow ambient air to enter the device. The addition of airflow from the airflow generator can help round the bottom edge 322, which, in effect, eases the transition from exhalation to inhalation.

Although the curve 310 includes the application of an air flow generator, the air flow generator and related air supply sub-assembly supply air at a rate of less than or equal to about 60 L/min, less than or equal to about 40 L/min, or otherwise. In certain aspects, the airflow generator can be set at a pressure that is more than, less than or equal to about the threshold pressure of the expiratory valve. In certain aspects, the airflow generator can be set at a pressure that is at least about 5 cmH20 and/or less than or equal to about 20 cmH20. In certain aspects, the airflow generator can be set at a pressure that is less than or equal to about 10 cmH20.

With lower flow rates, the airflow generator maintains pressure during apneic events and improves comfort without high airflow. In addition, the breathing curve 310 can reach a minimum pressure that is lower than CPAP's minimum pressure. Accordingly, the breathing curve 306 can better resemble a normal breathing curve. In certain aspects, the minimum pressure can be less than or equal to about 5 cmH20, less than or equal to atmospheric pressure, or otherwise.

The curve 310 simulates an apnea at the second curve 326. Even during an apneic event, the pressure can stay elevated 328 due to the inflow of air from the airflow generator. For example, if the user stops breathing during exhalation, the pressure generated from the airflow generator helps increase pressure until the pharynx reaches a pressure equal to that which opens the expiratory valve. If the user stops breathing during inhalation, the inspiratory valve closes and the pressure from the air flow generator helps raise the pressure again until the user inhales normally. When breathing resumes, the pressure decreases normally 330 for inspiration.

The combination of ambient air and the additional airflow can help rapidly pressurize the system 328 to quickly eliminate any apneas. In certain aspects, the system can re-pressurize the system from atmospheric pressure to a threshold pressure in less than about 5 second, less than about 3 second, or less than or equal to about one second. In certain aspects, the threshold pressure can be at least about 5 cmH20 and/or less than or equal to about 15 cmH20. In certain aspects, the threshold pressure can be about 8 cmH20, about 10 cmH20, about 15 cmH20, or otherwise.

In certain aspects, the device can re-pressurize with an airflow generator and air supply tubing administering airflow at less than or equal to about 60 L/min, less than or equal to about 40 L/min, or otherwise.

In certain aspects, the system can re-pressurize the airway at a rate of at least about 10 cmH20/second at an external air flow of less than or equal to about 60 L/min. In certain aspects, the system can re-pressurize the system at a rate of at least about 20 cmH20/second at an external air flow of less than or equal to about 40 L/min. This rapid increase in pressure is also possible in part because of a lack of holes or leak paths in the device assembly and a low interior volume within the device assembly.

FIGS. 19-37 and the associated text describe an exemplary device assembly that can be used to achieve curve 306 or curve 310.

Figure 14:
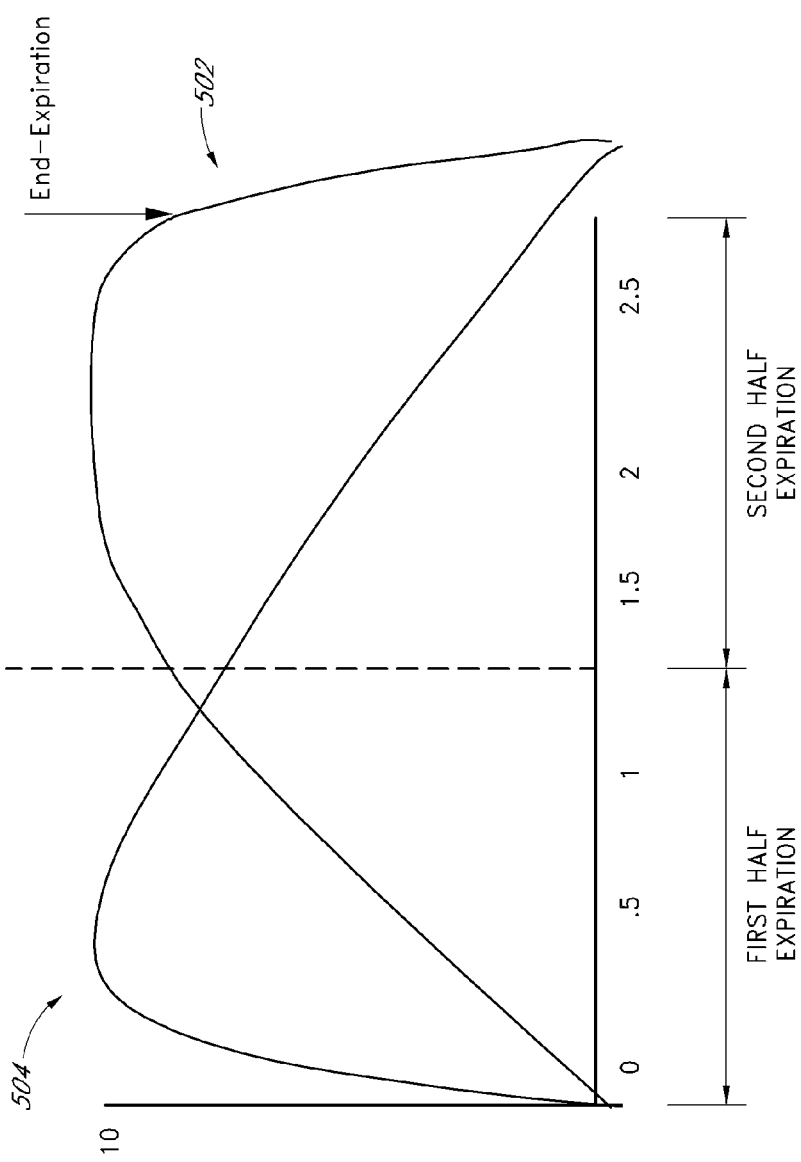
FIG. 14 is a graph comparing intranasal pressure curves for different devices including a device having a variable resistance valve capable of varying resistance independent of flow.

In certain variants, the expiratory valve can be a smart valve configured to apply an amount of resistance that is independent of flow. With the "smart valve," the device assembly can achieve high pressure even at low flow rates to maximize comfort. For example, if the flow rate is too high, the valve can open, so the pressure rises more slowly. If the flow rate is too low, the valve can close to help maintain pressure. FIG. 14 illustrates a smart valve curve 502 against a ProVent curve 504. The ProVent curve 504 exhibits features similar to the ProVent curve 302.

In certain aspects, the smart valve can help make expiration more comfortable by controlling one or more aspects of the breathing curve. As shown in curve 502, the smart valve can influence the slope of the ramp such that the rise in pressure is more gradual. In certain aspects, the rise in pressure is at a rate of no more than about 20 cmH20/second, no more than about 12 cmH20/second, and generally no more than about 10 cmH20/sec, or otherwise. Thus, the climb in pressure during exhalation to a reference pressure of 8 cmH20 requires greater than about 0.25 second, preferably greater than about 0.5 seconds, and, in some implementations, greater than about 1 second. In certain aspects, the expiratory valve can influence the slope of the ramp such that the mean pressure in the first half of expiration is less than the mean pressure in the second half of expiration.

In certain aspects, the expiratory valve can maintain a maximum pressure until the end of exhalation. In certain aspects, the maximum pressure is at least about 5 cmH20 and/or less than or equal to about 15 cmH20. In certain aspects, the maximum pressure is between about 9 cmH2O and 11 cmH20, and, in one embodiment, is about 10 cmH20.

In certain aspects, the resistance at about 0.5 seconds before the end of expiration can be higher than the resistance at about 0.5 seconds after the beginning of expiration. In certain aspects, the pressure can drop from the maximum threshold pressure to atmospheric pressure in less than one second, less than 0.5 seconds, or otherwise. Maintaining an elevated pressure until the end of exhalation ensures that the airway pressure is maintained at a desired level at the critical time when the patient changes from expiration to inspiration.

In certain aspects, the expiratory valve can help create an average expiratory time of less than or equal to three seconds to mimic normal breathing.

Figure 15A:
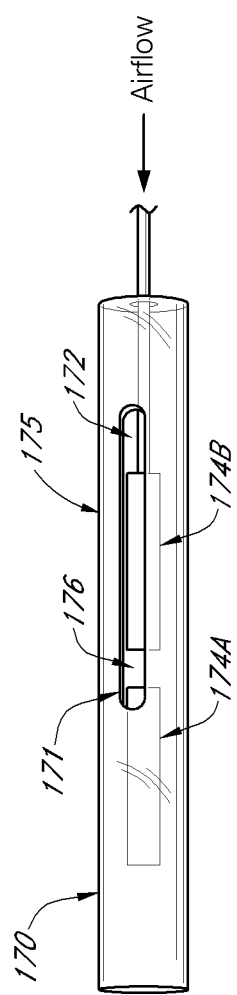
FIGS. 15A and 15B are perspective views of a slit-tube valve for providing variable resistance during expiration, according to one embodiment.
Figure 15B:
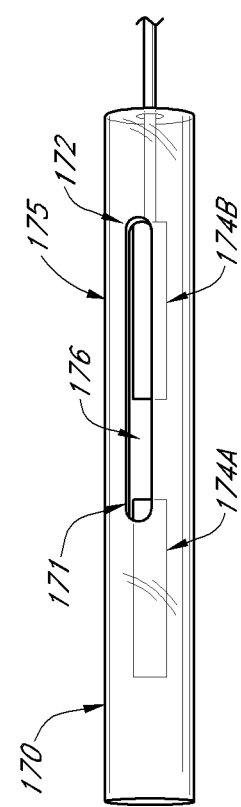

With reference now to FIGS. 15A and 15B, another variable resistance, one-way valve device 170, which may be used as part of an OSA device or system, is illustrated. In this embodiment, device 170 includes a tube 175 with a slit 171 and two opposing magnets, such as magnetic rods 174A and 174B, disposed in tube 175. As illustrated in FIG. 15A, rod 174B is displaced by airflow in the direction of rod 174A during an initial portion of the expiratory phase to shorten the gap 176 between them and create an opening 172 in slit 171, through which exhaled air may pass. As illustrated in FIG. 15B, as the expiratory airflow declines rod 174B will move farther away from rod 174A, thus closing opening 172. In various embodiments, one of rods 174 may be coupled with a stationary support member, and the other rod 174 may be free to move. In addition, rods 174 may have facing ends that either oppose or attract one another, according to various embodiments, and may be forced to move in one way or another, based on whether they tend to oppose or attract.

Referring now to FIGS. 16A and 16B, in another embodiment, a variable resistance valve device 190, which may be a one-way valve, may include a tube with multiple apertures 192 disposed along part of its length, and a movable airflow blocker 196, such as a piston or other movable wall carried within the tube. A spring 194 is attached at one end to airflow blocker 194, and at the other end to an attachment point such as the sidewall of the tube or a stationary support member 198. As illustrated in FIG. 16A, when a patient exhales ("<<Airflow"), the force of the exhaled air pushes against air flow blocker 196, which compresses spring 194 and exposes a number of apertures 192 in proportion to the exhaled air flow, through which exhaled air can escape from tube 191. As the flow of exhaled air decreases, as in FIG. 14B, spring 194 elongates, pushing airflow blocker through tube 191, such that fewer apertures 192 are exposed for the release of exhaled air. At the end of exhalation, no apertures 192 are available—i.e., valve 190 is closed. The apertures can be replaced by one or two or more axially extending slits, and the spring can be mounted for either compression or tension under exhaled airflow.

Figure 17A:
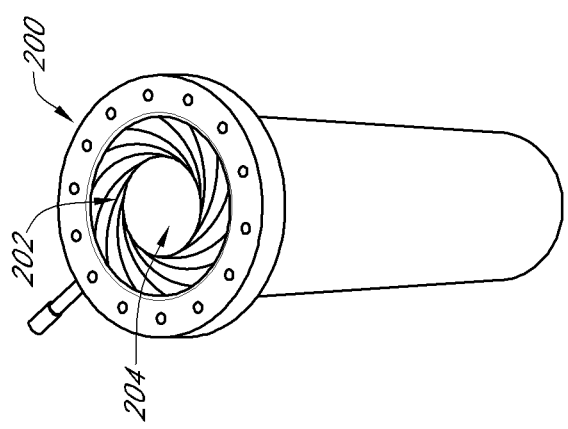
FIGS. 17A-17C are perspective views of an iris valve for providing variable resistance during expiration, according to one embodiment.
Figure 17B:
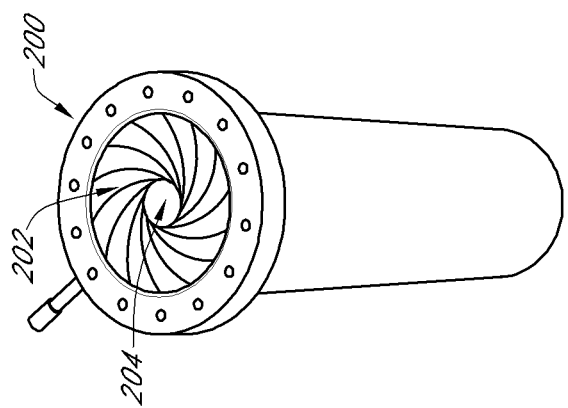
Figure 17C:
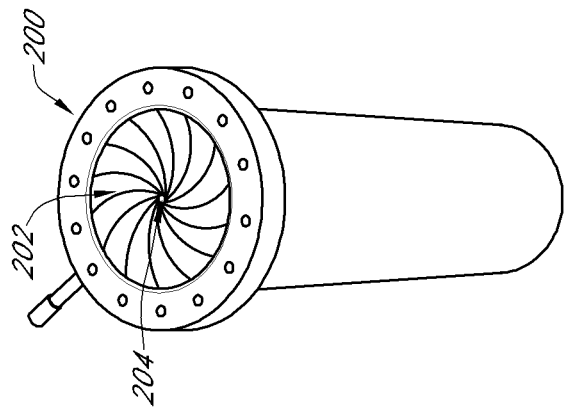

With reference now to FIGS. 17A-17C, in yet another embodiment, a variable resistance valve device 200, which may be a one-way valve, may include an iris valve 202 that opens and closes to allow exhaled air to escape while providing resistance to expired air. As shown in FIG. 17A, at the beginning of expiration, iris 202 may open to provide an opening 204 having a first diameter. As airflow decreases during the course of the expiratory phase, as in FIG. 17B, iris may close partially, so that opening 204 assumes a second, smaller diameter to maintain pressure above a predetermined minimum. Finally, toward the end of expiration, as in FIG. 17C, opening 204 may shrink to a third, smallest diameter and may close all the way at end expiration. As with the previously described embodiments, closure of valve 200 may occur in increments or continuously during expiration, according to various embodiments.

As mentioned above, the various embodiments of variable resistance, one-way, expiration valves described in this application may generally be driven (or actuated) in one of two different ways. In some embodiments, expiration valves may be automatically driven in response to the patient's breath. For example, a flap valve, comprising a flexible diaphragm of a resilient material, such as Nitinol, may open when the opening pressure of exhalation is achieved and then may close gradually as the flow of exhaled air decreases. A Nitinol valve may also change its shape in response to the heat from a patient's breath. In other embodiments, expiration valves may be driven by mechanical or electromechanical means. For example, an iris valve as described in FIGS. 17A-17C may be electromechanically programmed to open and close with specified timing, or a blocker such as the one described in FIGS. 16A and 16B may be moved back and forth with a solenoid or other mechanical means. This timing may be according to general timing of breath cycles or may be customized for a patient. In some embodiments, an OSA treatment system may measure patient breathing patterns and use that information to time the opening and closing of a valve. The opening and closing of a valve may be actuated by a controller coupled with the valve, and the controller may receive instructions via wired or wireless electronic connections or by built-in electronics.

In various embodiments, an expiratory valve may be configured to open and close or may be electromechanically forced to open and close at any of a number of suitable pressures and combinations of pressures. In some embodiments, a valve may open and then close continuously/gradually during expiration, while in alternative embodiments, the valve may close in increments. In various embodiments, a valve may have an opening pressure of between about 0 cm H2O and about 15 cm H2O, or more preferably between about 2 cm H2O and about 5 cm H2O. In some embodiments, the expiration valve may open at an opening pressure of about 0-5 cm H2O and close at a pressure of at least about 5 cm H2O. Alternatively or additionally, the valve may be configured to generate an intra-airway pressure of about 0-5 cm H2O during an early portion of expiration and an intra-airway pressure of about 5-15 cm H2O during a later portion of expiration. In some embodiments, the expiration valve is configured to generate greater intra-airway pressure during the later portion of expiration than during the early portion. In some embodiments, an opening of the expiration valve may have a larger surface area and/or diameter during the early portion of expiration and a smaller surface area and/or diameter during the later portion of expiration.

In one embodiment, a device for treating OSA and/or snoring may include simply a mask (or nostril insert or covering) for covering the nose (or at least the nostrils) of a patient, along with one or two variable resistance, one-way, expiration valves. Such a device may be configured as a nasal pillow, a nose-only mask, a mouth-only mask, or a nose-and-mouth mask. Such a device may be used by itself, without any positive airflow device (airflow generator, tube, etc.), to help treat OSA and/or snoring by generating expiratory resistance during the expiratory phase of breathing. In some embodiments, such a device may also be compatible with a positive airflow generator—either a CPAP machine or a smaller, low-flow machine as described herein. In other embodiments, such a device may be a stand-alone therapy.

Figure 18B:
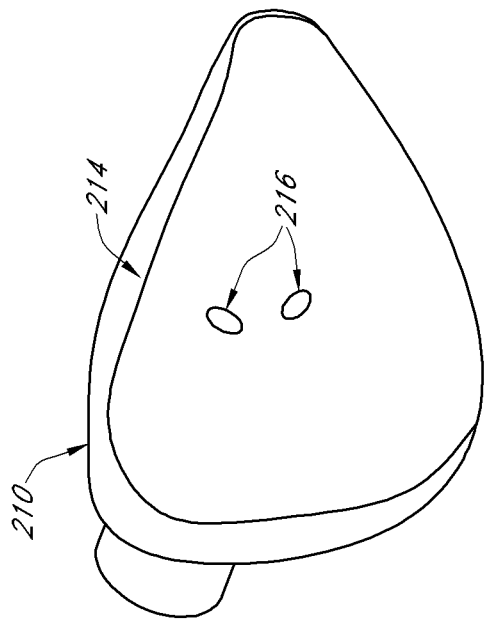
FIGS. 18A and 18B are perspective views of a custom made nasal mask, according to one embodiment.
Figure 18A:
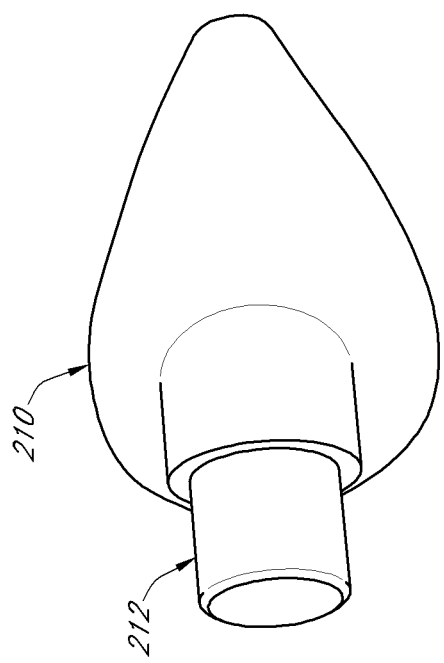

With reference now to FIGS. 18A and 18B, a prototype of one embodiment of a custom manufactured nasal mask 210 is illustrated. Nasal mask 210 generally includes a port 212 for attaching to an airflow generator tube, a sealing surface 214 for creating a seal (or at least for conforming with) the patient's face around the nose, and openings 216 for allowing breathing through the nostrils. Custom made mask 210 may be manufactured in any suitable fashion. In one embodiment, mask 210 may be made by placing a mask making material or standard-shaped mask over a patient's face, assessing the shape of the patient's face using the material, and then customizing the mask based on the assessment. In another embodiment, mask 210 may be made by assessing the patient's face in advance, such as by taking a digital photographic image or CT scan of the patient's head, and then using that data to form mask 210. For example, CT scan data may be used to make a negative image of the patient's face, and the negative image may be used to make a mold from which mask 210 may be formed.

As mentioned previously, in alternative embodiments, a mask may take any of a number of other forms and sizes. In some embodiments, for example, a mask may be configured similar to a nasal pillow. In other embodiments, a mask may be a nasal-only mask, resting over the patient's nose and surrounding the nostrils. In yet another embodiment, a mask may cover only the mouth of the patient, and in yet another embodiment, the mask may cover the patient's mouth and nose. In some embodiments, a mask may include an energy conversion device for converting breath energy into electrical energy. In some embodiments, a mask may alternatively or additionally include an air flow generator attached directly to the mask. In these and other embodiments, one or more straps may be attached to the mask to help attach it to a patient's head.

In many embodiments, however, such as the embodiment shown in FIGS. 18A and 18B, mask 210 is configured to conform to a patient's nose and/or includes a contact surface with adhesive, such that it may be comfortably worn over the nose without the use of any straps and without falling off. By conforming to the patient's face, forming a seal with the patient's face, or both, masks 210 described in this application will reduce or eliminate the air leaks that occur with currently available CPAP mask, thus eliminating the need for high-pressure, high-flow-rate air and thus eliminating many of the side effects of CPAP.

In some embodiments, the system that has been described herein may be used not only for providing air flow and resistance when needed to help treat OSA or snoring, but may also be used to deliver one or more airborne therapeutic substances to a patient. For example, an OSA system as described herein may be used to deliver oxygen, supplements, steroids, or any other medication or treatment that may be delivered in gaseous form or aerosolized. Some potential conditions that may be treated using the system as a therapeutic substance delivery device include but are not limited to COPD, rhinitis, pneumonia, acute respiratory distress syndrome, and/or acute lung injury.

Additionally, the OSA treatment system described herein may also be used to treat conditions other than OSA. For example, the system may be used to treat some patients with chronic obstructive pulmonary disease (COPD) or emphysema. In these cases, the system may be adjusted to provide a different amount of positive air flow than that used in treating OSA. In COPD or emphysema, for example, little or no positive air flow may be used, and the system may predominantly work by providing resistance to exhalation. The system may be similarly used in/adjusted for treatment of other disease states.

In various alternative embodiments, a device for treating OSA may include one or more nasal coverings to cover one or both nostrils and one or more expiration airflow resistors coupled with the nasal coverings in such a way as to provide resistance to expired/exhaled air. In one embodiment, for example, the nasal covering may be a mask similar to that shown in FIGS. 4A-4E. However, rather than being attached to a tube and air flow generator, this alternative embodiment of a mask would not include an air flow generator valve and would be a stand-alone device. It may include one or multiple expiration valves. It may also include an inspiration valve, or expiration and inspiration valve(s) may be combined, with resistance to expiration being greater than resistance to inspiration. The mask may form an airtight seal, as previously described. Such a device would thus help provide expiratory pressure (PEEP and/or EPAP), but would not provide enhanced inspiratory pressure. In some embodiments, the exhalation valve may increase resistance to exhaled air over the course of the expiratory phase, as described in detail above.

In one example of such an alternative embodiment, a nasal device such as those described in U.S. Pat. Nos. 8,061,357 and 7,798,148 (hereby incorporated by reference) may be improved by providing such a device with a variable resistance valve, as described above. Again, such a valve may be configured to open at an opening pressure and then gradually, continuously, and/or progressively close over the course of an expiratory phase to provide increasing amounts of resistance. Alternatively, such a valve may open at an opening pressure and then open further during exhalation to provide decreased resistance and maintain pressure within a desired range. Such a device, with any of a number of "variable resistance" valves, may help provide PEEP and/or EPAP in a way not achieved by the valves described in the above-referenced patents. In various alternative embodiments, the variable resistance valve may be used on a single-nostril device, a two-nostril (whole-nose) device, a mask that covers the nose (both nostrils) or a mask that covers the nose and mouth. A single nostril device typically includes one valve, while two-nostril devices may include one valve or multiple valves, such as one valve per nostril. In some patients, a mask that covers the nose and mouth may be advantageous, since some patients switch to mouth breathing when experiencing resistance to exhaling through the nose.

Any of the valves described above may be used with these nasal covering/airway resistor embodiments. For example, valves may include but are not limited to the flap valve and the membrane valve described above. In alternative embodiments, valves that open initially at a predetermined opening pressure and later close down partially during exhalation to increase resistance may be used in some embodiments.

FIGS. 19-37 illustrate an exemplary embodiment of a device 400 configured to exhibit one or more respiratory properties discussed herein. The features of the device 400 described below are generally designed to create a unique breathing profile as discussed above, increase patient comfort, and create an aesthetically pleasing device. Increasing patient comfort will help increase patient compliance.

In certain aspects, the dimensions of the device 400 can be configured to decrease the total size and weight of the device 400 as compared to traditional CPAP devices. The embodiments described herein can unchain the customer from the bedside table where traditional CPAP air flow generators usually sit. In addition, the embodiments described herein can be travel size, so that they do not need to be checked at the airport. Further details regarding the dimensions of the device assembly are described below.

Figure 19:
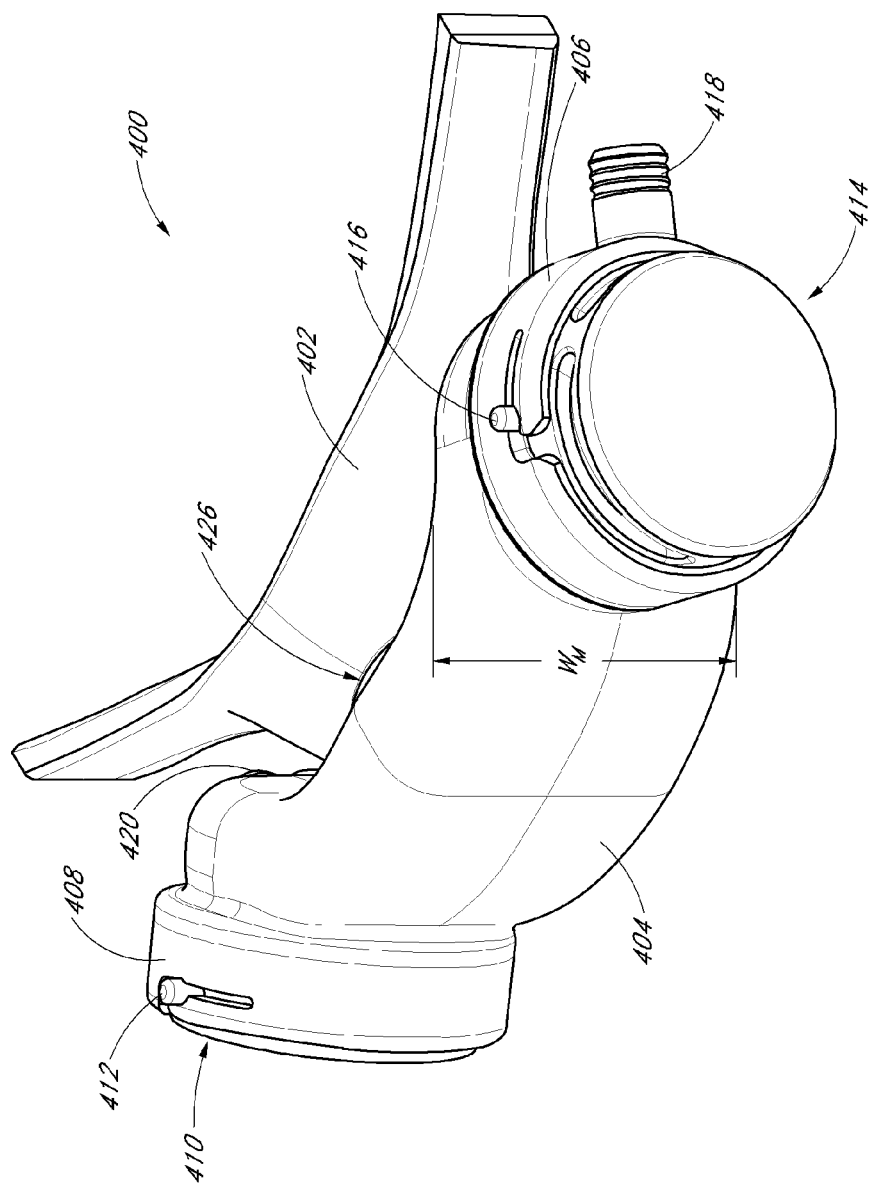
FIG. 19 illustrates an exemplary embodiment of a device assembly.

As shown in FIG. 19, the device 400 can be configured to be worn by a user. The mask portion 402 and/or manifold 404 can be secured to a user's face using any securing feature, including, but not limited to, a frame, an adhesive, straps, Velcro, and/or buckles. In certain aspects, the device 400 can be strapped to the user's face using one or more straps. In certain aspects, the straps are provided with a releasable connection to the device 400, such that they are replaceable or exchangeable. For example, the user can use one set of straps for travel or otherwise while awake and a different set of straps for bed. In certain aspects, the device assembly can include frame portions extending from the manifold 404 or mask 402. The frame portions can extend across at least a part of the user's face, for example, to a position near the user's ears or over the user's ears. At least a part of the frame portions can include a resilient material, such as a rubber material, to increase patient comfort.

In certain aspects, the mask portion 402 can include any of a variety of resilient materials capable of conforming to the user's face. For example, the mask portion 402 can include a gel to help conform the mask portion 402 to the user's face, or an interface comprising silicone or other elastomers or polymers known in the art.

In certain aspects, the mask portion 402 can include one or more openings configured to permit the inflow and outflow of air. Each of the one or more openings can be configured to be in air flow communication with, and potentially at least partially align with a nasal cavity. In certain aspects, the mask portion 402 can include two openings, each opening configured to align with a nasal cavity.

Figure 20:
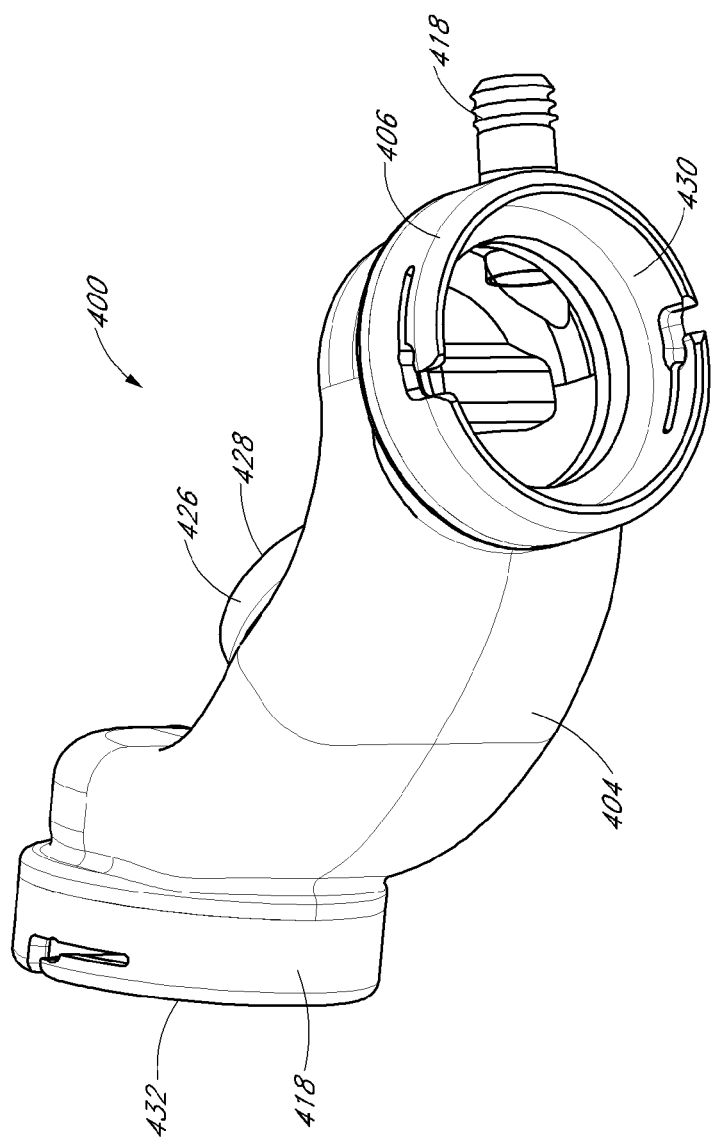
FIG. 20 illustrates an exemplary embodiment of a manifold of the device assembly illustrated in FIG. 19.
Figure 21A:
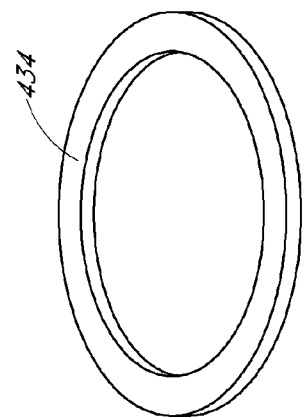
FIGS. 21A-C illustrate an exemplary embodiment of a valve seat seal of the device assembly illustrated in FIG. 19.
Figure 21C:
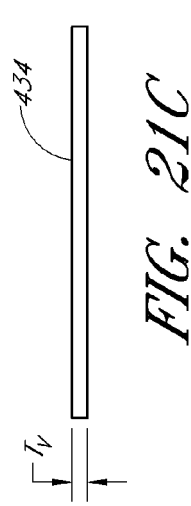
Figure 21B:
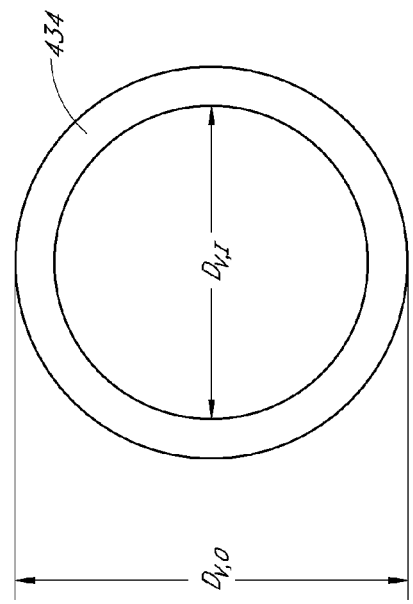

As shown in FIGS. 19-20, the device 400 can include a manifold 404. In certain aspects, the manifold 404 can be configured to generally fit the contours of the user's face. For example, the manifold 404 can have a generally curved configuration.

The mask portion 402 can be coupled directly or indirectly to the manifold 404. In certain aspects, the manifold 404 can directly engage the mask portion 402 using any connection mechanism, including, but not limited to, a detent, an adhesive, a curing technique, a molding technique, a screw-fit, a snap fit, and/or an interference fit. As shown in FIG. 20, the manifold 404 can include a fitting 426 designed to removably or permanently engage the mask portion 402.

In certain aspects, the manifold 404 can include one or more openings configured to permit the inflow and/or outflow of air through a valve, air supply tubing, and/or the mask. Unlike traditional CPAP devices, neither the manifold 404 nor the mask 402 typically includes intentional leak paths.

In certain aspects, the manifold 404 can include a mask opening 428 disposed on the same side of the manifold as the mask portion 402 and in communication with the user's nasal cavity. In certain aspects, the manifold 404 can include an inspiratory opening 432 in communication with an inspiratory valve 410 and/or an expiratory opening 430 in communication with an expiratory valve 414.

The manifold 404 can be directly or indirectly connected to one or more valves. In certain aspects, the manifold 404 can engage the mask portion 402 on a first side of the manifold 404 and engage the one or more valves on a second side of the manifold 404. In certain aspects, the mask portion 402 and valves can be positioned on the same side of the manifold 404. In some examples, the manifold 404 can be coupled to a first side of a valve, and the mask portion 402 can be coupled to a second side of the valve.

In certain aspects, the device 400 can include a separate inspiratory valve 410 and an exhalation valve 414 to help create tailored breathing profiles as described above. In certain aspects, the inhalation 410 and exhalation 414 valves are sized and positioned so that they do not blow on the patient in an uncomfortable way. In addition, the inhalation 410 and exhalation 414 valves can be sized and positioned for better aesthetics and ergonomics. In certain aspects, the valves can be configured to minimize noisy outflow. For example, the valves can be designed with smaller outlets. Further details regarding valve dimensions are described below.

In the exemplary embodiment shown in FIGS. 19-20, the manifold 404 can engage one or more valve inserts, such as an expiratory valve insert 406 and/or an inspiratory valve insert 408. Each valve insert 406, 408 can be coupled together with the manifold 404 using any connection mechanism, including, but not limited to, an adhesive, a cure technique, a molding technique, a detent, a screw-fit, a snap fit, and/or an interference fit.

Each valve insert 406, 408 can engage a valve 410, 414. The valve inserts 406, 408 can be configured to facilitate the exchange of valves 410, 414 depending on the desired resistance profiles. The ability to exchange valves can improve the capability of doctors to perform patient evaluations and customize or adjust the performance of the device 400.

In certain aspects, the inspiratory valve insert 408 can be coupled to the inspiratory valve 410. Although FIG. 19 illustrates a detent 412 connecting the inspiratory valve insert 408 and the inspiratory valve 410, the inspiratory valve insert 408 and the inspiratory valve 410 can be coupled together using any connection mechanism in alternative to or in addition to the detent 412, including, but not limited to, an adhesive, a cure technique, a molding technique, a screw-fit, snap fit, and/or an interference fit.

In certain aspects, the expiratory valve insert 406 can be coupled to the expiratory valve 414. Although FIG. 19 illustrates a detent 416 connecting the expiratory valve insert 406 and the expiratory valve 414, the expiratory valve insert 406 and the expiratory valve 414 can be coupled together using any connection mechanism in alternative to or in addition to the detent 416, including, but not limited to, an adhesive, a cure technique, a molding technique, a screw-fit, a snap fit, and/or an interference fit.

In certain aspects, one or both of the valves 410, 414 can be directly connected to the manifold 404 and/or mask 402 using any suitable connection mechanism, including, but not limited to, an adhesive, a cure technique, a molding technique, a detent, a screw-fit, a snap fit, and/or an interference fit.

In certain aspects, the device 400 can include one or more air supply connectors 418, 420 configured to engage one or more air supply tubes. Each connector 418, 420 can be coupled to the device 400 using any connection mechanism, including, but not limited to, an adhesive, a curing technique, a molding technique, a detent, a screw-fit, snap fit, and/or an interference fit. The connectors 418, 420 can permit the inflow of air from an air flow generator. Although FIGS. 19-20 illustrate the device 400 having a first air supply connector 420 positioned near the inspiratory valve 410 and a second air supply connector 418 positioned near the expiratory valve 414, the one or more air supply connectors 418, 420 can be positioned anywhere along the device 400 to provide air flow communication with the interior of the manifold, including, but not limited to, a front surface of the manifold 404, a side surface of the manifold 404, a rear surface of the manifold 404, and/or to the mask portion 402.

Figure 19A:
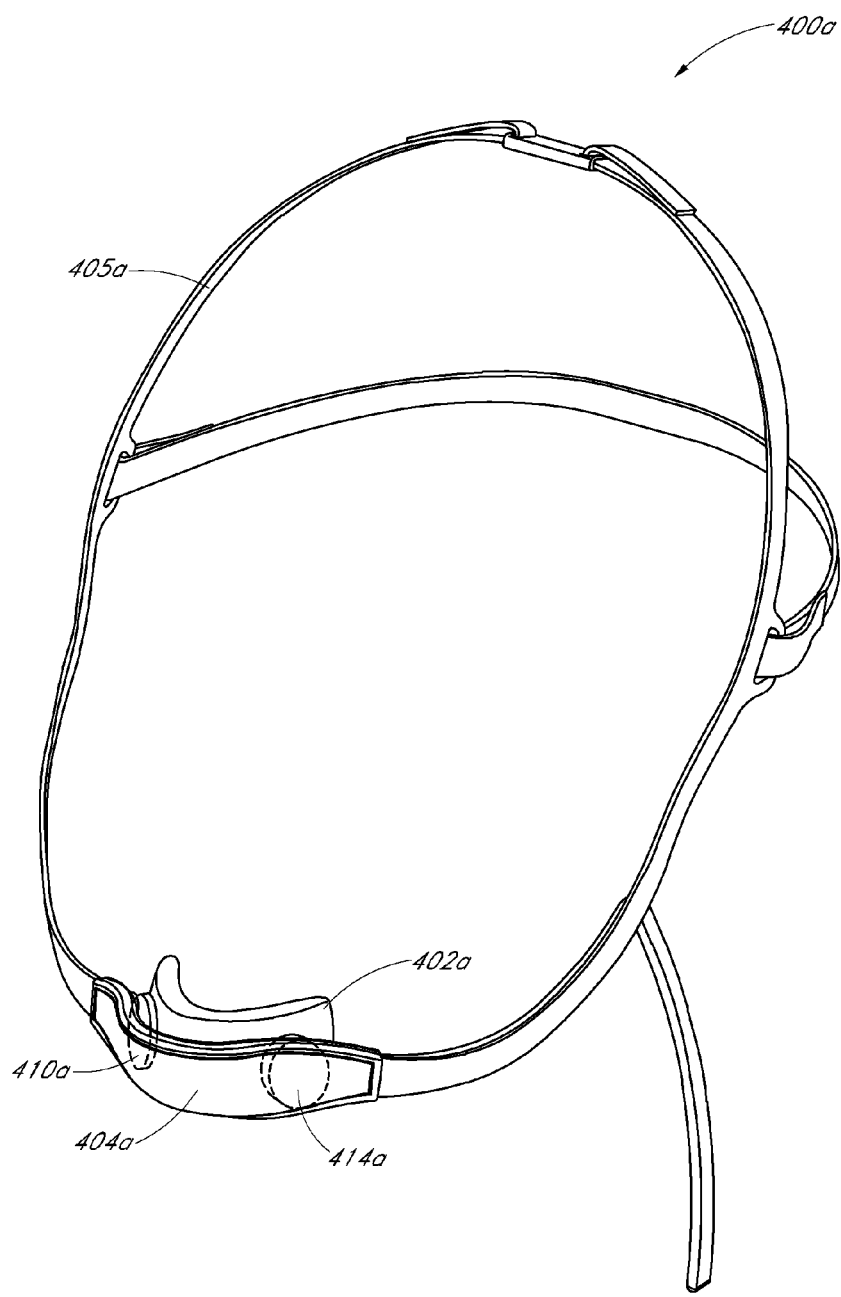
FIGS. 19A-B illustrate another exemplary embodiment of the device assembly.
Figure 19B:
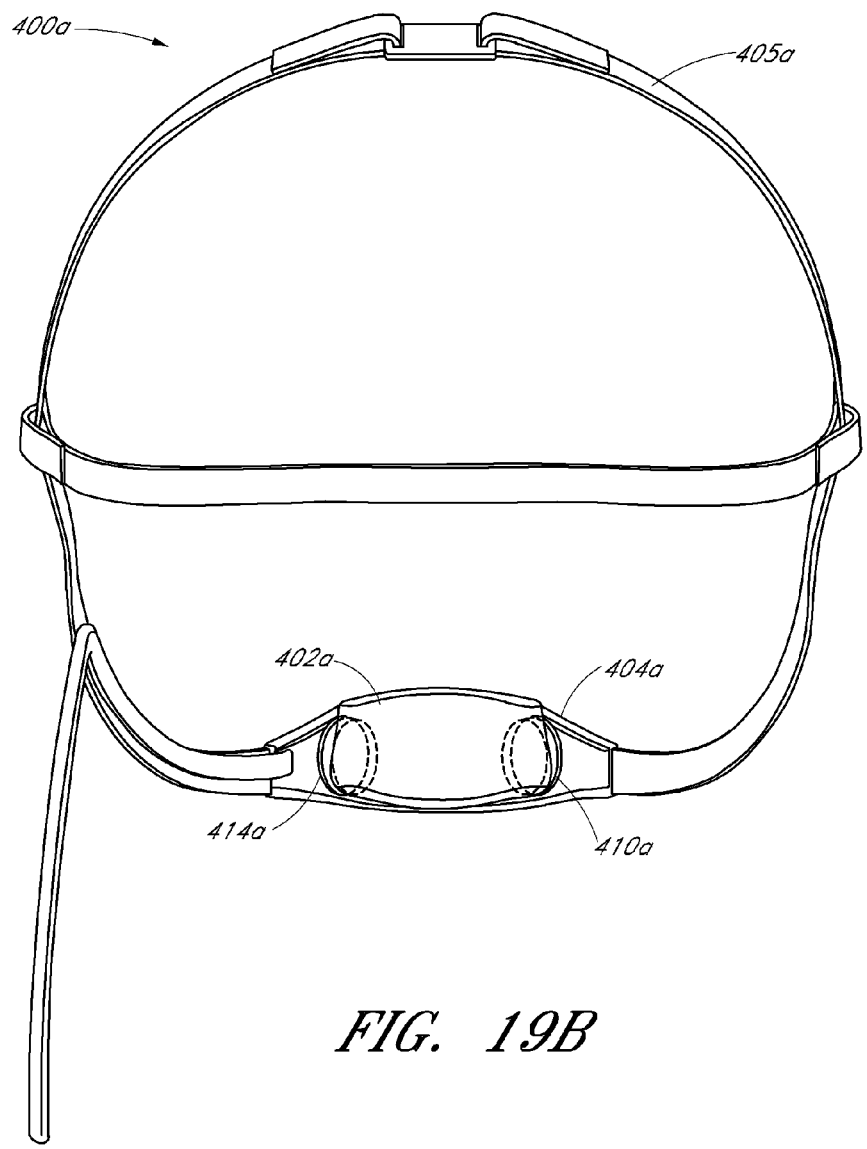

FIGS. 19A and 19B illustrate another embodiment of the device 400a including a mask 402a, a manifold 404a, and straps 405a. The device 400a can include any of the features (e.g., valves, connectors, etc.) described in connection with the device 400 shown in FIG. 19. In addition, the device 400a can include any of the dimensions described in connection with the device 400.

Although the components described with respect to FIGS. 19-20 and sub-components described below are described as separate components, one or more of the components and/or sub-components can be constructed together as a single integral component such as by molding. Each component of the device 400 is described in further detail below.

The device 400 can include a valve seat seal 434 in contact with each valve insert 406, 408 or manifold 404. In certain aspects, the valve seat seal 434 can be an O-ring. The valve seat seal 434 can provide a sealing mechanism for ensuring that no air leaks or flow disruptions occur even during pressurization changes of less than or equal to about 0.001 psig. The valve seat seal 434 can be constructed using any number of suitable techniques, including, but not limited to machining, stamping, molding, SLA processing, or casting. In certain aspects, the valve seat seal 434 can be constructed from any medical grade polymers or metals, including, but not limited to, silicone, rubber, polyethylene, polyethylene terephthalate, Teflon®, copper, gold, palladium, and/or silver. In certain aspects, the valve seat seal 434 can include a material having a durometer of at least about 10 A and/or less than or equal to about 50 D.

In certain aspects, each valve insert 406, 409 and/or manifold 404 can include a support structure to support the valve seat seal 434, such as a ridge or a recess.

In certain aspects, the valve seat seal 434 can have a thickness $T_V$ of less than or equal to about 0.1 inches, less than or equal to about 0.04 inches, or otherwise. In certain aspects, the outer diameter $D_{V,O}$ of the seal 434 can be less than or equal to about an inner diameter of a valve insert 406, 408, greater than or equal to about an outer diameter of a valve 410, 414, greater than or equal to about a diameter of a manifold opening 430, 432, or otherwise. In certain aspects, the outer diameter $D_{V,O}$ of the seal 434 can be less than or equal to about 1.5 inches, less than or equal to about 1.0 inches, or otherwise. In certain aspects, the valve seat seal 434 can have an inner diameter $D_{V,I}$ of less than or equal to about 1.0 inches, less than or equal to about 0.8 inches, or otherwise.

Figure 22A:
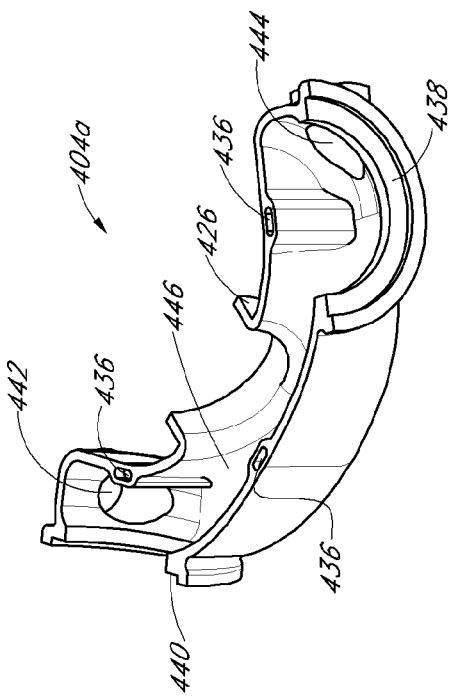
FIGS. 22A-C and 23A-C illustrate portions of the manifold illustrated in FIG. 20.
Figure 22B:
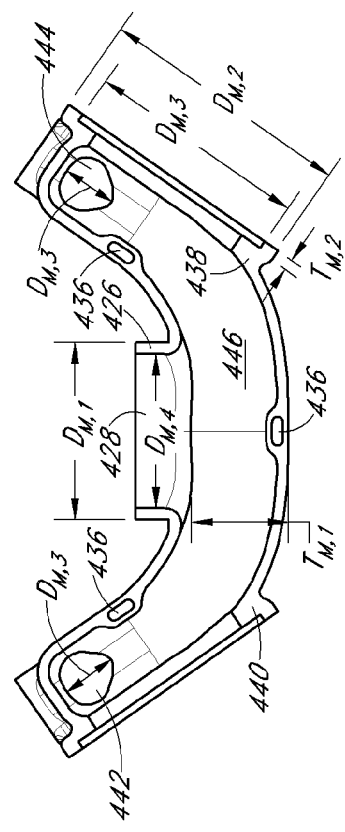
Figure 22C:
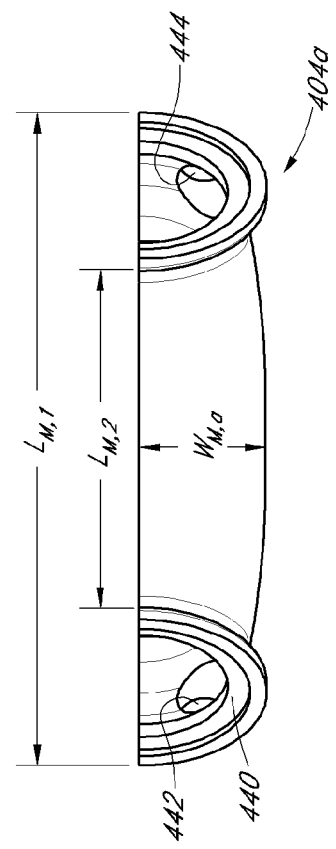
Figure 23A:
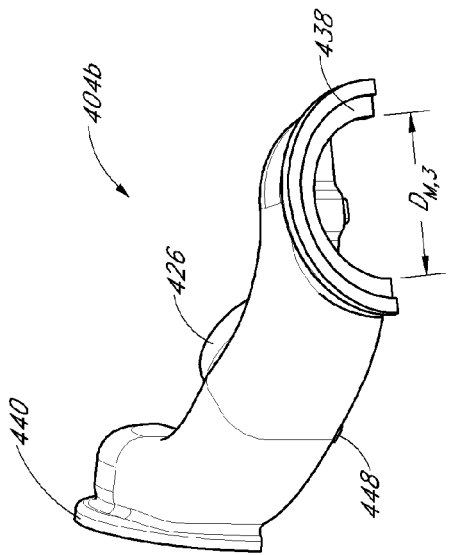
Figure 23B:
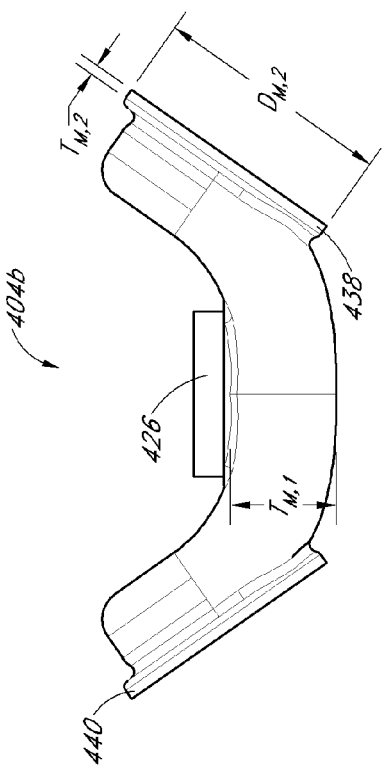
Figure 23C:
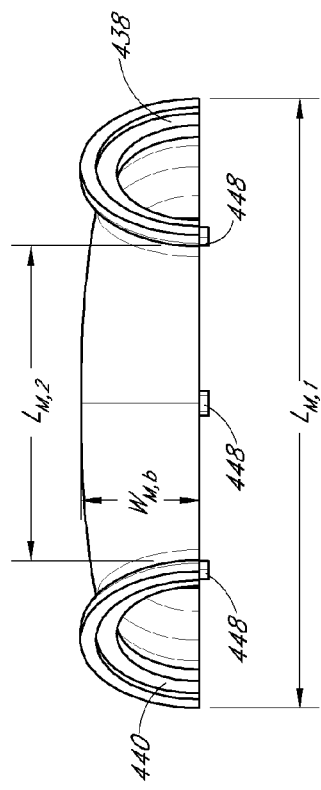

FIGS. 22-23 illustrate a bottom half portion 404a (FIGS. 22A-C) and a top half portion 404b (FIGS. 23A-C) of the manifold 404. The manifold 404 helps maintain the pressure and flow from the inspiratory valve 410 and flow to the expiratory valve 414. The manifold 404 also assists in communicating air supply to the user's air passageway.

Although FIGS. 22 and 33 illustrate the manifold 404 as two separate portions, the manifold can be constructed using any number of components, including a single component. With multiple components, the multiple components can be coupled using any suitable technique, including, but not limited to, bonding, molding, casting, insert molding, SLA processing, stamping, riveting/screwing together, or otherwise. As shown in FIGS. 22-23, the bottom half portion 404a can include one or more connection features 436, such as grooves, configured to mate with one or more corresponding features 448 on the top half portion 404b, such as protrusions.

The manifold 404 can include any medical grade polymers or metals, including, but not limited to, ABS, polycarbonate, nylon, Pebax®, acrylic, ceramic, carbon fiber, palladium, stainless steel, amorphous metal, and/or copper. In addition, the manifold 404 can be plated, coated with corrosion resistant materials, and/or painted.

Figure 35A:
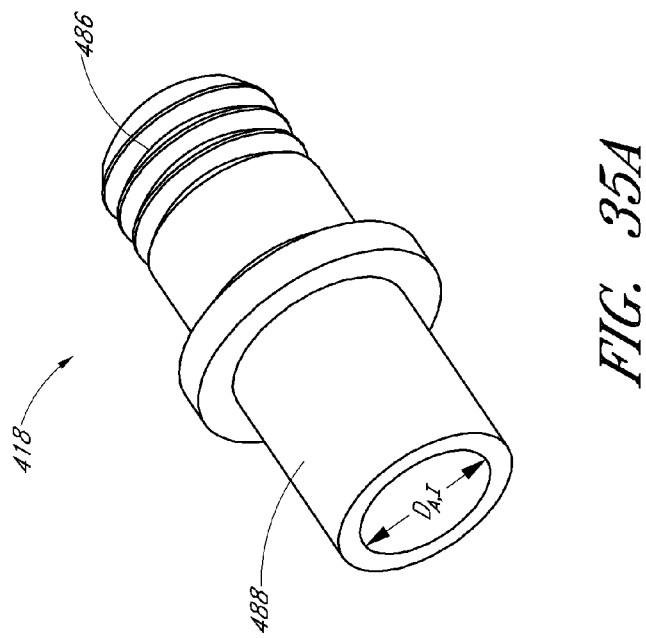
FIGS. 35A-35C illustrate an exemplary embodiment of an air supply connector.
Figure 35B:
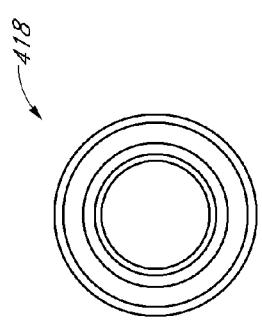
Figure 35C:
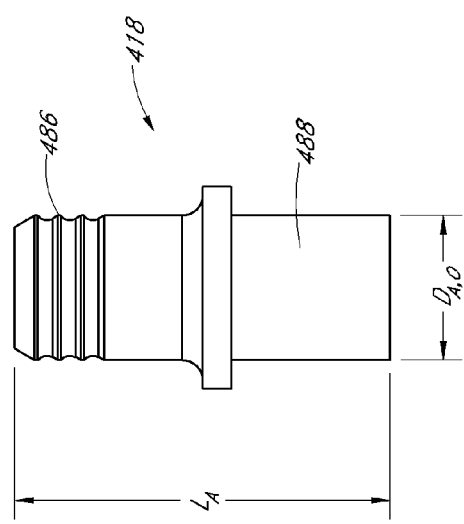

The manifold 404 can include one or more openings 442, 444 in communication with an airflow generator. As shown in FIGS. 22A-22C, the openings 442, 444 can be positioned on along a bottom surface of the manifold 404. However, as described above, the openings 442, 444 can be positioned elsewhere along the manifold 404 and/or mask 402. In certain aspects, the manifold 404 can connect to the air supply tubing (FIG. 36) using air supply connectors 418, 420 (FIGS. 35A-35C). In certain aspects, the manifold 404 can connect directly to the air supply tubing using any connection mechanism, including, but not limited to, adhesive bonding (e.g., using cyanoacrylate), curing (e.g., ultraviolet or otherwise), and/or insert molding.

In certain aspects, the manifold 404 can include one or more valve seats 438, 440 configured to mate with a corresponding feature of each valve insert 406, 408 or valve 410, 414. As shown in FIGS. 22C and 23C, the valve seat 438, 440 can be a recessed portion; however, the valve seat 438, 440 can additionally or alternatively include a groove, flange, protrusion, or otherwise.

The outer diameter $D_{M,2}$ of each of the valve seats 438, 440 can be the same or different. In certain aspects, the outer diameter $D_{M,2}$ the valve seats 438, 440 can be less than or equal to about 1.5 inches, less than or equal to about 1.0 inches, or otherwise. In certain aspects, the inner diameter $D_{M,3}$ the valve seats 438, 440 can be less than or equal to about 1.5 inches, less than or equal to about 1.0 inches, or otherwise.

In certain aspects, each of the valve seats 438, 440 can include a flange portion surrounding the valve seat 438, 440. In certain aspects, the thickness $T_{M,2}$ of each of the flange portions can be less than or equal to about 0.1 inches. In certain aspects, the thickness $T_{M,2}$ can be less than or equal to about 0.05 inches.

In certain aspects, the length $L_{M,2}$ between the valve seat 438 and the valve seat 440 can be less than or equal to about 2 inches, less than or equal to about 1.75 inches, or otherwise. In certain aspects, the $L_{M,2}$ between the valve seat 438 and the valve seat 440 can be less than or equal to two times the outer diameter of the valve seat $D_{M,2}$, less than or equal to about 1.75 times the outer diameter of the valve seat $D_{M,2}$, less than or equal to about 1.5 times the outer diameter of the valve seat $D_{M,2}$, or otherwise.

In certain aspects, the manifold 404 can have the mask opening 428 in communication with the user's naval cavity. In certain aspects, the mask opening 428 can have an outer diameter $D_{M,1}$ that can be less than or equal to an outer diameter $D_{M,2}$ of the valve seats 438, 440. In certain aspects, the mask opening 428 can have an inner diameter $D_{M,4}$ that can be less than or equal to an inner diameter $D_{M,3}$ of the valve seats 438, 440. In certain aspects, the mask opening 428 can have an outer diameter $D_{M,1}$ that can be less than or equal to about 1.0 inch, less than or equal to about 0.8 inches, or otherwise. In certain aspects, the mask opening 428 can have an inner diameter $D_{M,4}$ that can be less than or equal to about 0.8 inches, less than or equal to about 0.7 inches, or otherwise.

In certain aspects, the thickness of the manifold 404 can be generally uniform along a length of the manifold 404. In certain aspects, the thickness of the manifold 404 can taper toward the end portions of the manifold 404. In certain aspects, the thickness $T_{M,1}$ of the manifold 404 at the region of greatest thickness can be less than or equal to about 1.0 inches, less than or equal to about 0.5 inches, or otherwise. In at least a portion of the manifold 404, the thickness can be less than or equal to about 0.3 inches, less than or equal to about 0.25 inches, or otherwise.

In certain aspects, the diameter $D_{M,3}$ of each air supply opening can be less than or equal to about one-half the diameter $D_{M,2}$ of each valve seat, less than or equal to about one-third the internal diameter $D_{M,3}$ of a valve seat 438, 440, less than or equal to about one-fourth the internal diameter $D_{M,3}$ of a valve seat 438, 440, or otherwise. In certain aspects, the diameter $D_{M,3}$ of each air supply opening 442, 444 can be less than or equal to about 0.5 inches, less than or equal to about 0.25 inches, or otherwise.

In certain aspects, the width $W_M$ ($W_{M,a}+W_{M,b}$) of the manifold can be less than or equal to about three times the outer diameter $D_{M,2}$, less than or equal to about two times the outer diameter $D_{M,2}$, less than or equal to about 1.5 times the outer diameter $D_{M,2}$, or otherwise. In certain aspects, the width $W_M$ of the manifold 404 can be less than or equal to about 2 inches, less than or equal to about 1.5 inches, less than or equal to about 1.25 inches, or otherwise.

In certain aspects, the length $L_{M,1}$ of the manifold 404 can be less than or equal to about five times the size of the outer diameter $D_{M,2}$, less than or equal to about three times the size of the outer diameter $D_{M,2}$, less than or equal to about two times the size of the outer diameter $D_{M,2}$, or otherwise. In certain aspects, the length $L_{M,1}$ of the manifold 404 can be less or equal to about 3 inches, less than or equal to about 2.5 inches, or otherwise. In certain aspects, the length $L_{M,1}$ of the manifold 404 can be about 2.75 inches. In certain aspects, the length $L_{M,1}$ can be less than or equal to about 3 times the width $W_M$, less than or equal to about 2.5 times the width $W_M$, less than or equal to about 2 times the width $W_M$, or otherwise. In certain aspects, the length $L_{M,1}$ can be less than or equal to about 10 times the thickness $T_{M,1}$, less than or equal to about 6 times the thickness $T_{M,1}$, less than or equal to about 5 times the thickness $T_{M,1}$, or otherwise.

In certain aspects, the manifold 404 can carry air in an interior volume 446 of the manifold. Due to the reduced interior volume 446 of the manifold as compared to traditional CPAP device, as well as the inspiratory and expiratory valves, no intentional leak paths are necessary. In certain embodiments, the interior volume 446 of the manifold 404 and/or mask 402 can be less than about 150 mL, less than about 100 mL, less than 50 mL, or otherwise. In certain embodiments, an interior volume of the air supply tubes can be less than about 50 mL, less than about 20 mL, or less than about 15 mL. Accordingly, the ratio between the interior volume 446 of the manifold 404 and/or mask 402 to an interior volume of the air supply tubes can be about 5:1, 5:2, or otherwise.

FIGS. 24-27 illustrate an exemplary embodiment of the inspiratory valve 410 and each of its components. The inspiratory valve 410 can be a one-way valve, including, but not limited to, a flap valve. The inspiratory valve 410 can be configured to open during inhalation and close during exhalation. In certain aspects, the inspiratory valve 410 can be configured to open when the pressure gradient between the mask and ambient is less than or equal to about 0.01 psig.

The inspiratory valve 410 can be positioned anywhere along the flow path between the mask 402 and the air flow generator. For example, the inspiratory valve 410 can be positioned on the manifold 404 or along an air supply tube. In certain aspects, the inspiratory valve 410 can be positioned along an anterior surface of the manifold 404. In certain aspects, the inspiratory valve 410 can be positioned along a posterior surface of the manifold.

Figure 24A:
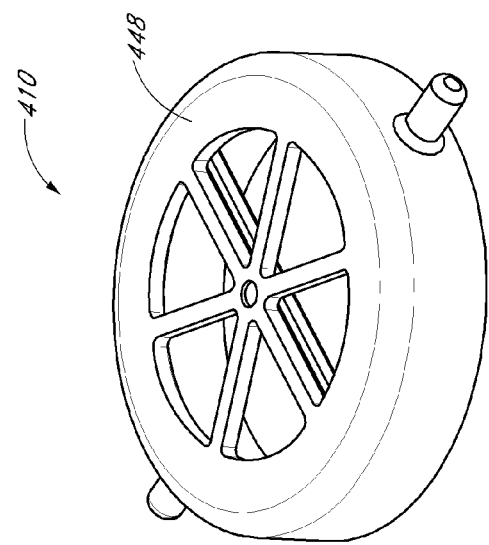
FIGS. 24A-27C illustrate an exemplary embodiment of an inspiratory valve and each of its components.
Figure 24B:
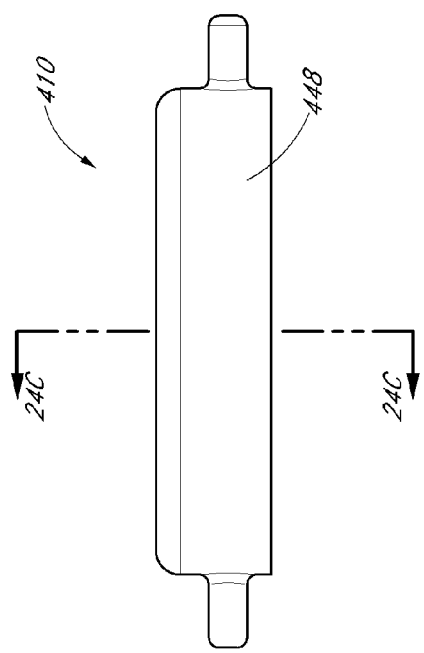
Figure 24C:
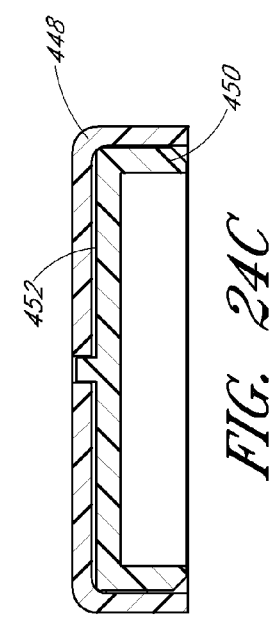

As shown in FIG. 24, the inspiratory valve 410 can include a cap 448, a body 450, and a membrane 452. Each of the inspiratory valve components can be coaxially aligned and substantially circular or cylindrical. An outer diameter of the body 450 can be less than an inner diameter of the cap 448, such that the body 450 can fit within the cap 448. The membrane 452 can be disposed between an inner surface of the cap 448 and an outer surface of the body 450.

In certain aspects, the cap 448 and the body 450 can include metallic materials, including, but not limited to, aluminum, stainless steel, titanium, cobalt chrome, and/or nitinol. In certain aspects, the cap 448 and the body 450 can include plastic materials, including, but not limited to, Pebax®, Grilamid®, nylon, Delrin®, Teflon®, ABS, polycarbonate, and/or PVC. In certain aspects, the cap 448 and the body 450 can include any material having a durometer of at least about 30 A and/or less than or equal to about 95 D.

Figure 25A:
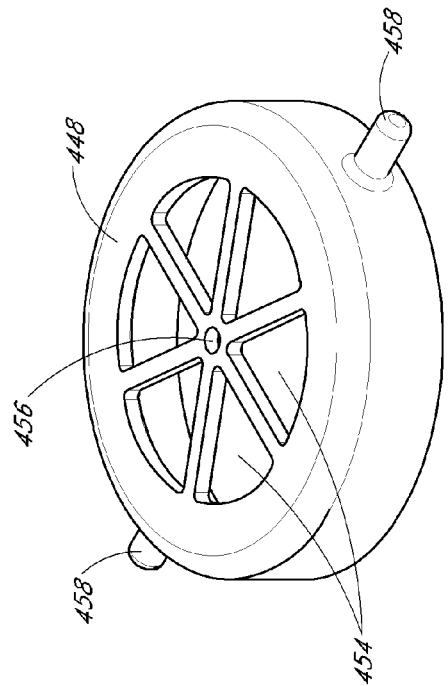
Figure 25B:
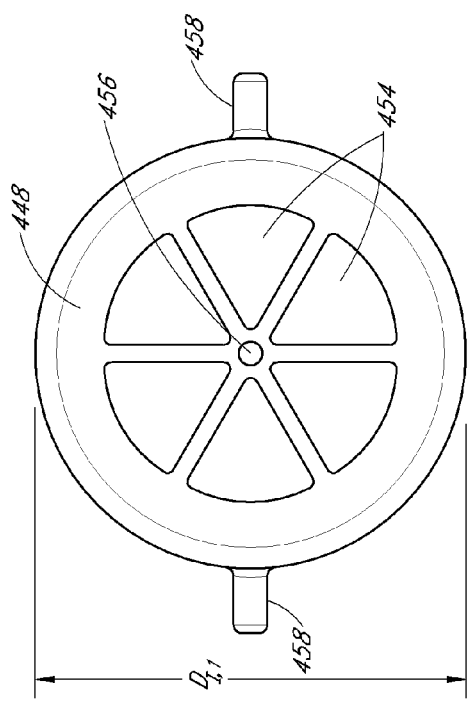
Figure 25C:
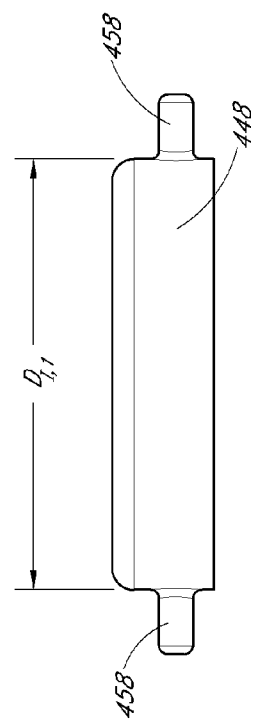

As shown in FIGS. 25A-25C, the cap 448 can include one or more openings 454 through which air can flow into the manifold 404. The cap 448 can include six openings 454 or otherwise. In certain aspects, the cap 448 can include an opening 456 for receiving a portion of the body 450. Although the opening 456 shown in FIG. 25A is centrally located, the opening 456 can also be off-center.

In certain aspects, the cap 448 can include one or more detent portions 458 for engaging the inspiratory valve insert 408. In certain aspects, the width $W_{I,1}$ of each detent portion 458 can be less than or equal to about 0.1 inches. Although, as described above, the inspiratory valve 410 can couple with the inspiratory valve insert 408 using any connection mechanism described herein.

In certain aspects, the outer diameter $D_{I,1}$ of the cap 448 can be less than or equal to about the outer diameter $D_{M,2}$ of at least one of the valve seats 438, 440. In certain aspects, the outer diameter $D_{I,1}$ of the cap 448 can be less than or equal to about 1.0 inch. In certain aspects the width $W_M (W_{M,a}+W_{M,b})$ of the manifold 404 can be less than three times the outer diameter $D_{I,1}$, less than two times the outer diameter $D_{I,1}$, less than 1.5 times the outer diameter $D_{I,1}$, or otherwise. In certain aspects, the length $L_M$ of the manifold 404 can be less than about five times the outer diameter $D_{I,1}$, less than about three times the outer diameter $D_{I,1}$, or otherwise.

Figure 26A:
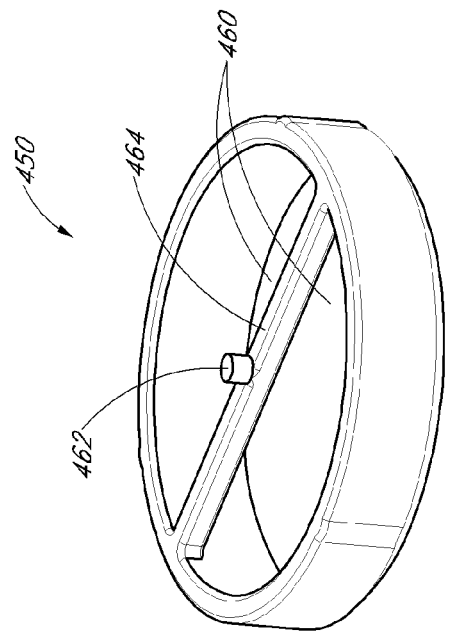
Figure 26B:
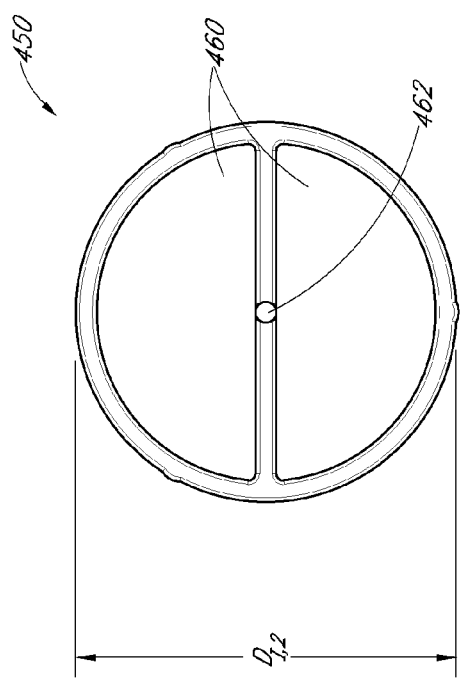
Figure 26C:
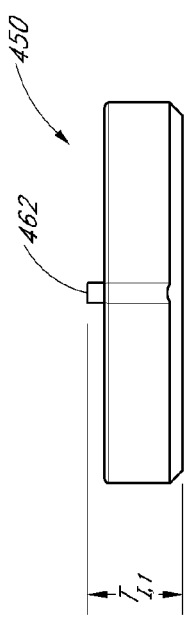

As shown in FIGS. 26A-26C, the body 450 can include one or more openings 460 to permit the inflow of air and movement of the membrane 452. For example, the body 450 can include a cross-bar 464 to create two openings 460. In certain aspects, the body 450 can include a protrusion 462 configured to be received by the opening 456 of the cap 448.

In certain aspects, the outer diameter of $D_{I,2}$ the body 450 can be less than or equal to about 1.0 inches, less than or equal to about 0.9 inches, or otherwise. In certain aspects, the thickness $T_{I,1}$ of the body 450 can be less than or equal to about one-third the outer diameter of $D_{I,2}$ the body 450, less than or equal to about one-fourth the outer diameter of $D_{I,2}$ the body 450, or otherwise. In certain aspects, the thickness $T_{I,1}$ of the body 450 can be less than or equal to about 0.25 inches.

Figure 27A:
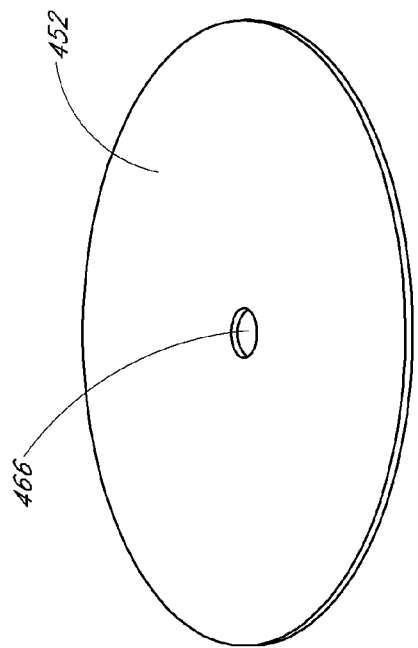
Figure 27B:
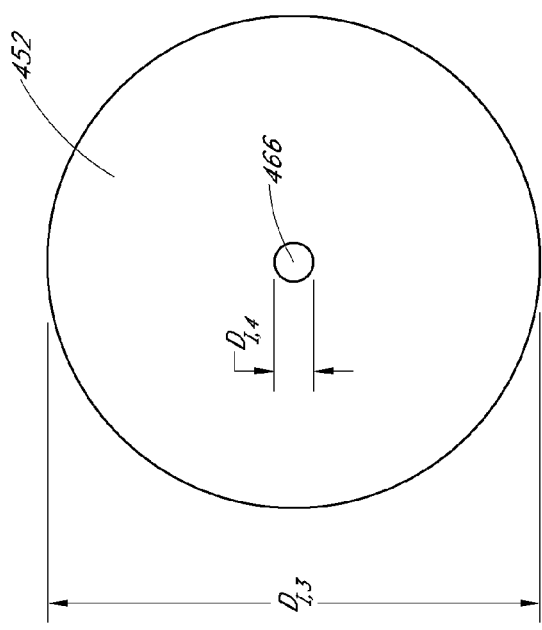
Figure 27C:
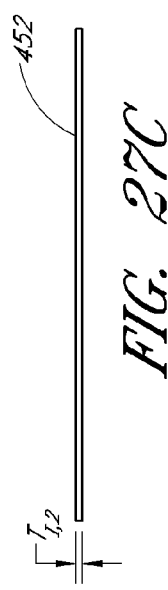
Figure 28A:
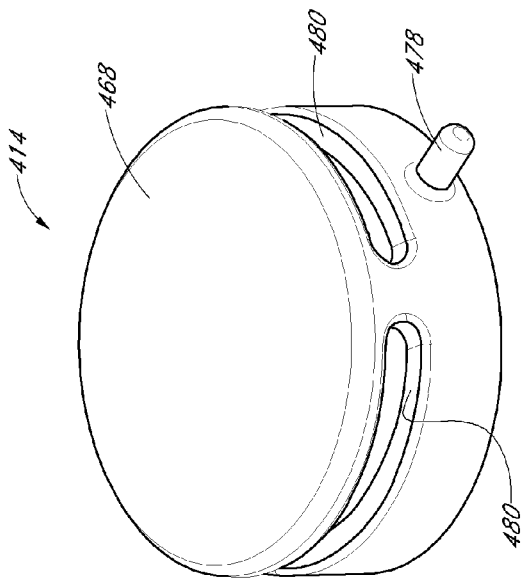
FIGS. 28A-33C illustrate an exemplary embodiment of an expiratory valve and each of its components.
Figure 28B:
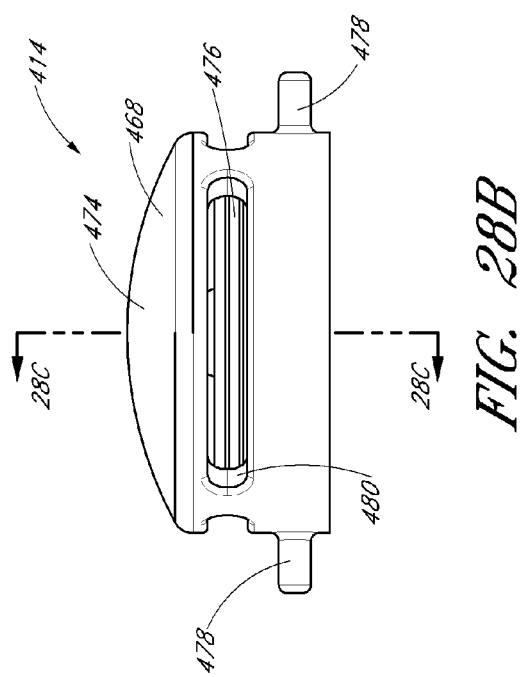
Figure 28C:
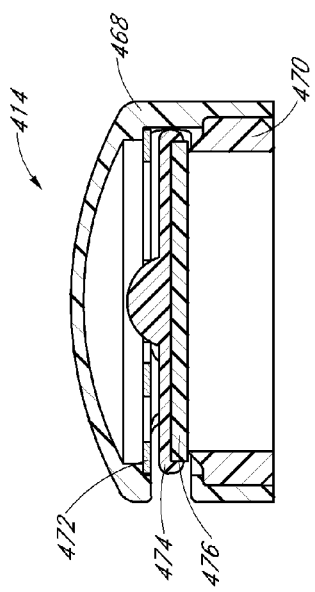

FIGS. 27A-27C illustrate different views of the membrane 452. In certain aspects, the membrane 452 can include a soft durometer material of less than or equal to about 50 D. In certain aspects, the membrane 452 can include a material including, but not limited to, rubber, silicone, nylon, and/or polyethylene. The membrane 452 can be manufactured using any suitable technique, including, but not limited to, extruding, casting, or molding. In certain aspects, the membrane 452 can include an opening 466, centrally located, or otherwise, configured to receive the protrusion 462 of the body 450. In certain aspects, a diameter $D_{I,3}$ of the membrane 452 can be less than or equal to about 1.0 inch, less than or equal to about 0.75 inches, or otherwise. In certain aspects, the diameter $D_{I,4}$ of the opening 466 can be less than or equal to about 0.1 inches, less than or equal to about 0.6 inches, or otherwise. In certain aspects, the thickness $T_{I,2}$ of the membrane can be less than or equal to about 0.01 inches.

FIGS. 28-33 illustrate an exemplary embodiment of an expiratory valve 414 and each of its components. In certain aspects, the expiratory valve can be a spring-loaded valve, a relief valve, smart valve, or otherwise.

The expiratory valve 414 can be positioned anywhere along the flow path between the mask 402 and the air flow generator. For example, the expiratory valve 414 can be positioned on the manifold 404 or along an air supply tube. In certain aspects, the expiratory valve 414 can be positioned along an anterior surface of the manifold 404. In certain aspects, the expiratory valve 414 can be positioned along a posterior surface of the manifold 404.

The expiratory valve 414 can be a one-way valve configured to create pressure without external air flow. In certain aspects, the expiratory valve 414 can be configured to open during period of exhalation when the pressure exceeds a threshold value. In certain aspects, the expiratory valve 414 can be configured to relieve pressure at a threshold pressure of at least about 5 cmH2O and/or less than or equal to about 15 cmH20. In certain aspects, the threshold pressure can be within the range of about 8 cmH20 and about 12 cmH20, and, in one embodiment, is about 10 cmH20. In certain aspects, the expiratory valve 414 can close again when the pressure falls below the threshold pressure.

In certain scenarios, it may be desirable for the expiratory valve to vary resistance based on the flow rate. For example, the expiratory valve can be a spring-loaded valve configured to vary resistance. The change in resistance can be inversely dependent on flow. As air flow increases, the expiratory valve can decrease resistance to keep pressure substantially constant. As air flow decreases, the expiratory valve can increase resistance, which can facilitate the application of positive airway pressure.

In certain aspects, the expiratory valve 414 can include a cap 468, a body 470, a spring 472, a follower 474, and/or a seal 476. Each of the expiratory valve components can be coaxially aligned and substantially circular or cylindrical.

In certain aspects, the spring 472, the follower 474, and the seal 476 can be configured to create the necessary spring force to create the desired level of resistance. In certain aspects, the spring force can be at least about 0.001 lbs./inch in a low profile (less than or equal to about 25 mm height and less than or equal to about 25 mm diameter) minimal orifice opening area at least about 0.1 sq. mm for break pressure and a maximum of about 90 sq. mm for full head pressure opening. The desired level of resistance and/or threshold pressure can be adjustable and used for titration.

The cap 468 and the body 460 can be manufactured using any suitable technique, including, but not limited to, machining, molding, extruding, casting, or SLA processing. In certain aspects, the cap 468 and the body 460 can include a ceramic material or any metallic material, including, but not limited to aluminum (with or without a finish), stainless steel (e.g., 300 series), titanium, cobalt chrome, nitinol, and/or polymer. In certain aspects, the cap 468 and the body 460 can include a medical grade material having a durometer of at least about 50 A and/or less than or equal to about 50 D.

Figure 29A:
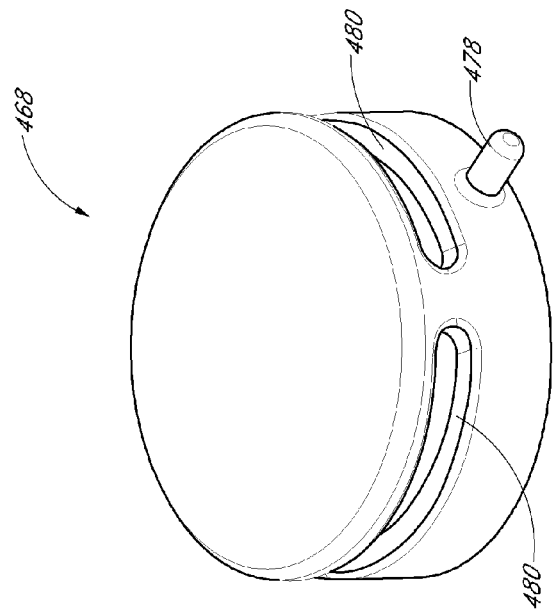
Figure 29B:
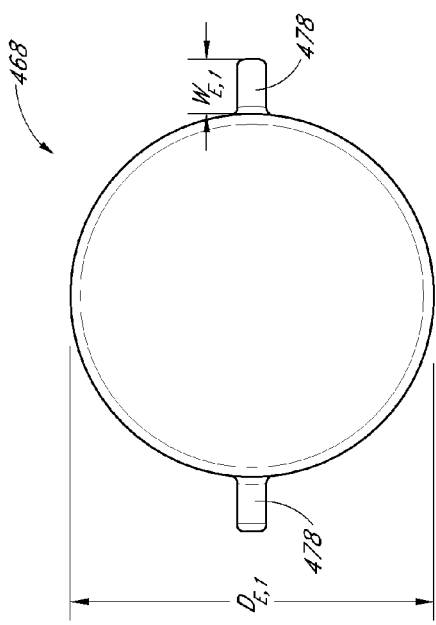
Figure 29C:
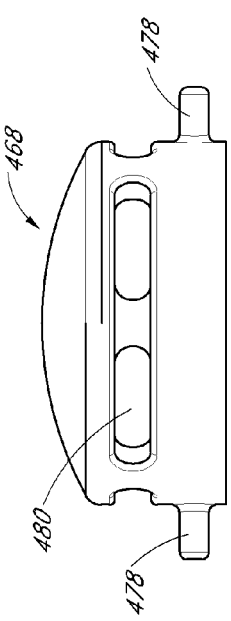

As shown in FIGS. 29A-29C, the cap 468 can include one or more openings 480 along a sidewall of the cap 468. In certain aspects, the cap 468 can include three openings 480 along the sidewall of the cap 468. These 480 openings permit the outflow of air through the valve 414.

In certain aspects, the expiratory valve 414 can include one or more detent portions 478 configured to couple the expiratory valve 414 to the expiratory valve insert 406. In certain aspects, the width $W_{E,1}$ of each detent portion 478 can be less than or equal to about 0.1 inches, less than or equal to about 0.08 inches, or otherwise. Although, as described above, any other connection mechanism discussed herein can be used to couple the expiratory valve 414 and the expiratory valve insert 406.

In certain aspects, the outer diameter $D_{E,1}$ of the cap 468 can be less than or equal to about the outer diameter $D_{M,2}$ of at least one of the valve seats 438, 440. In certain aspects, the outer diameter $D_{E,1}$ of the cap 468 can be less than or equal to about 1.0 inches. In certain aspects, the greatest width $W_M$ ($W_{M,a}+W_{M,b}$) of the manifold 404 can be less than three times the outer diameter $D_{E,1}$, less than two times the outer diameter $D_{E,1}$, less than 1.5 times the outer diameter $D_{E,1}$, or otherwise. In certain aspects, the length $L_M$ of the manifold 404 can be less than about five times the size of the outer diameter $D_{E,1}$, less than about three times the size of the outer diameter $D_{E,1}$, or otherwise.

Figure 30A:
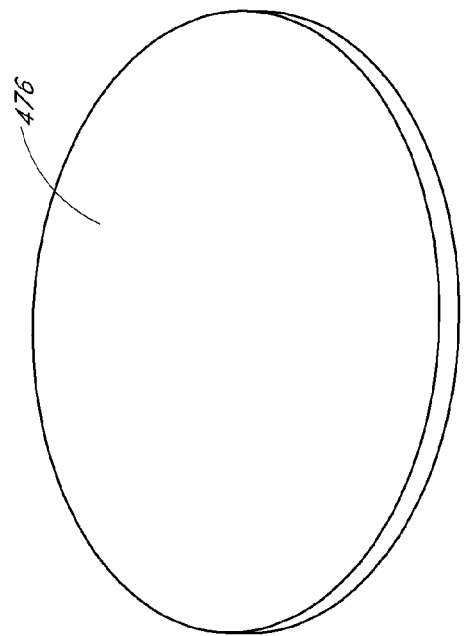
Figure 30B:
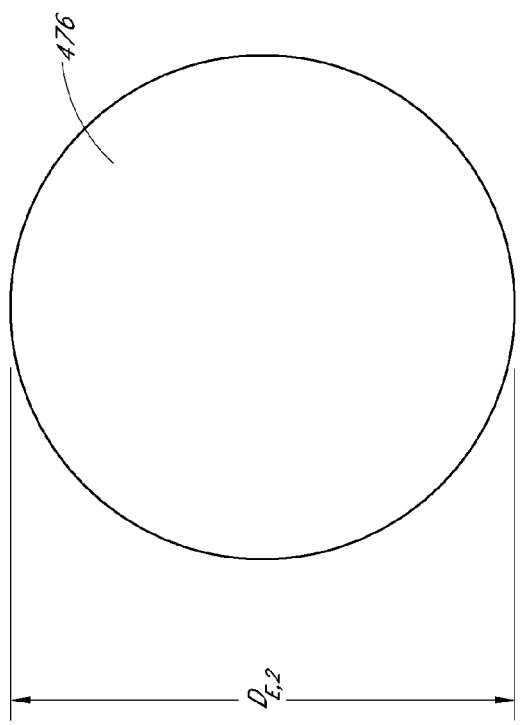
Figure 30C:
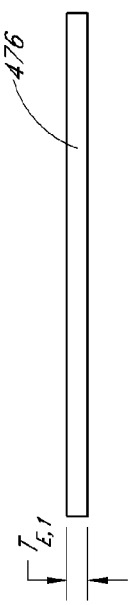
Figure 31A:
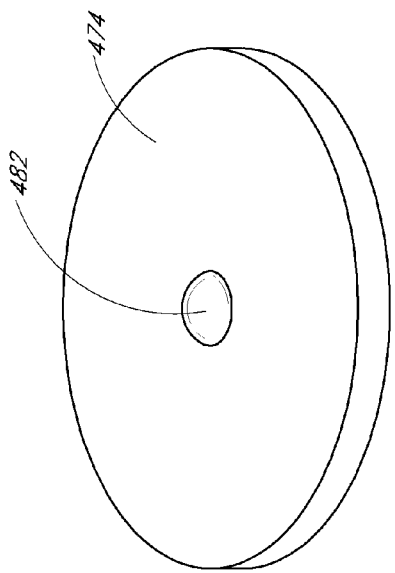
Figure 31B:
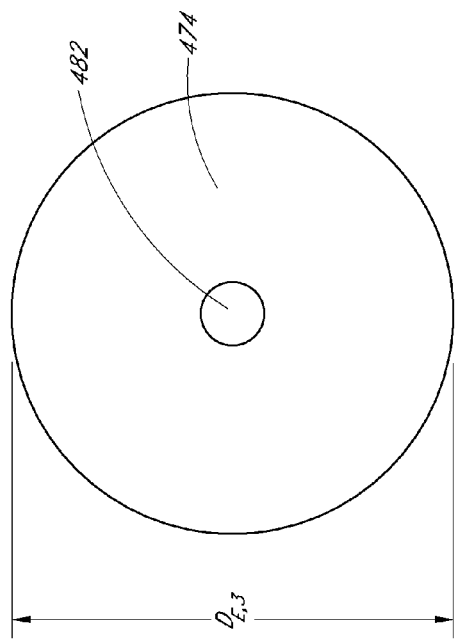
Figure 31C:

FIGS. 30A-30C illustrate different views of the seal 476, and FIGS. 31A-31C illustrate different views of the follower 474. In certain aspects, the follower 474 and the seal 476 can include any medical grade metallic or plastic material, including, but not limited to, aluminum, stainless steel (e.g., 300 series), cobalt chrome, palladium, nitinol, titanium, polyethylene, ABS, nylon, Pebax®, silicone, rubber, Teflon®, urethane, and/or Delrin®. In certain aspects, the follower 474 and the seal 476 can include any material having a durometer of at least about 20 A and/or less than or equal to about 50 D. In certain aspects, the follower 474 and the seal 476 can be constructed using any suitable manufacturing technique, including, but not limited to machining, extruding, casting, molding, or stamping.

In certain aspects, the diameter $D_{E,2}$ of the seal 476 can be less than the diameter $D_{E,1}$ of the cap 468. In certain aspects, the diameter $D_{E,1}$ of the seal 476 can be less than or equal to about 0.8 inches. In certain aspects, the thickness $T_{E,1}$ of the seal 476 can be less than or equal to about 0.1 inches, less than or equal to about 0.05 inches, about 0.04 inches, or otherwise.

As shown in FIGS. 31A-31C, the follower can include a protruding portion 482 about which the spring 472 can be positioned. In certain aspects, the diameter $D_{E,3}$ of the follower 474 can be less than the diameter $D_{E,1}$ of the cap 468 and/or greater than the diameter $D_{E,2}$ of the seal 476. In certain aspects, the diameter $D_{E,3}$ of the follower 474 can be less than or equal to about 1.0 inches, less than or equal to about 0.9 inches, or otherwise. In certain aspects, the thickness $T_{E,2}$ of the protrusion can vary depending on the desired spring force of the valve. For example, the thickness $T_{E,2}$ can be at least about 0.05 inches and/or less than or equal to about 0.1 inches.

Figure 32A:
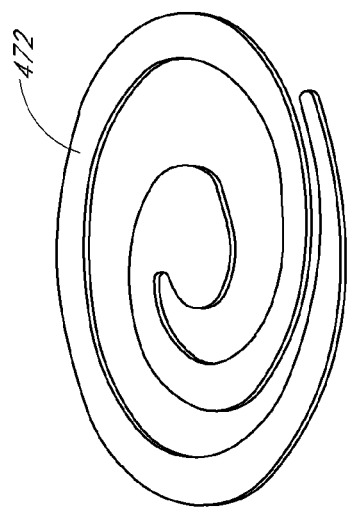
Figure 32B:
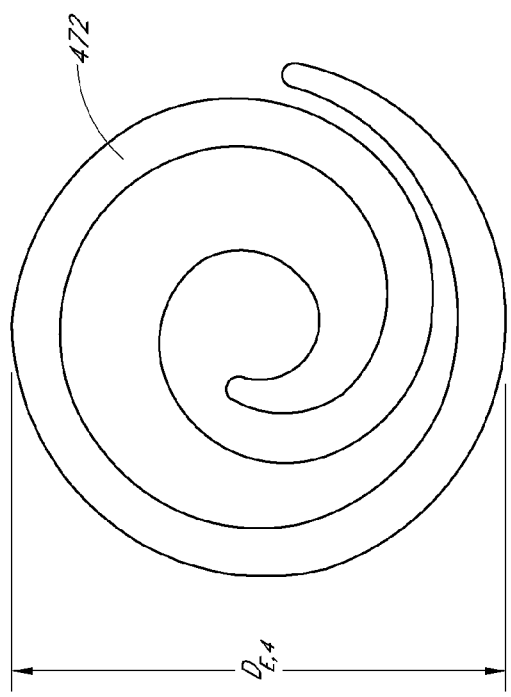
Figure 32C:
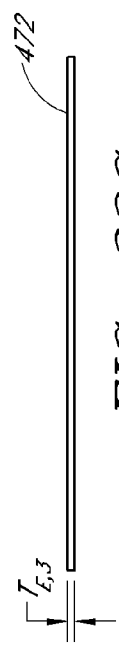

FIGS. 32A-32C illustrate different views of the spring 472. In certain aspects, the spring 472, the spring can be generally circular. In certain aspects, the spring 472 can include one or more protrusions extending from the spring 472 and coplanar with a top surface and/or bottom surface of the spring 472. In certain aspects, the spring 472 can include medical grade metallic or plastic materials, including, but not limited to, stainless steel (e.g., 300 series), nitinol, spring steel, palladium, copper, titanium, ABS, Pebax®, nylon, polyethylene, polyethylene terephthalate, and/or rubber. In certain aspects, the spring 472 can include a material having a durometer of at least about 10 A and/or less than or equal to about 50 D. The spring 472 can be manufactured using any suitable technique, including, but not limited to, laser cutting, water jetting, stamping, broaching, coining, machining, chemical etching, or electrical discharge machining.

In certain aspects, the diameter $D_{E,4}$ of the spring 472 can be less than the diameter $D_{E,1}$ of the cap 468, greater than the diameter $D_{E,2}$ of the seal 476, and/or substantially the same as the diameter $D_{E,3}$ of the follower 474. In certain aspects, the diameter $D_{E,4}$ of the spring 472 can be less than or equal to about 1.0 inches, less than or equal to about 0.9 inches, or otherwise. In certain aspects, the thickness $T_{E,3}$ of the spring 472 can vary depending on the desired spring force of the valve. For example, the thickness $T_{E,3}$ can be at least about 0.005 inches and/or less than or equal to about 0.015 inches. In certain aspects, as the desired relief pressure increases, the thickness $T_{E,3}$ of the spring increases. In certain aspects, the thickness $T_{E,3}$ of the spring can increase linearly with the desired relief pressure. In certain aspects, for a threshold relief pressure of about 5 cmH2O, the thickness $T_{E,3}$ can be about 0.005 inches. In certain aspects, for a threshold relief pressure of about 7 cmH2O, the thickness $T_{E,3}$ can be about 0.007 inches. In certain aspects, for a threshold relief pressure of about 9 cmH2O, the thickness $T_{E,3}$ can be about 0.009 inches. In certain aspects, for a threshold relief pressure of about 11 cmH2O, the thickness $T_{E,3}$ can be about 0.011 inches. In certain aspects, for a threshold relief pressure of about 13 cmH2O, the thickness $T_{E,3}$ can be about 0.013 inches. In certain aspects, for a threshold relief pressure of about 15 cmH2O, the thickness $T_{E,3}$ can be about 0.015 inches.

Figure 33A:
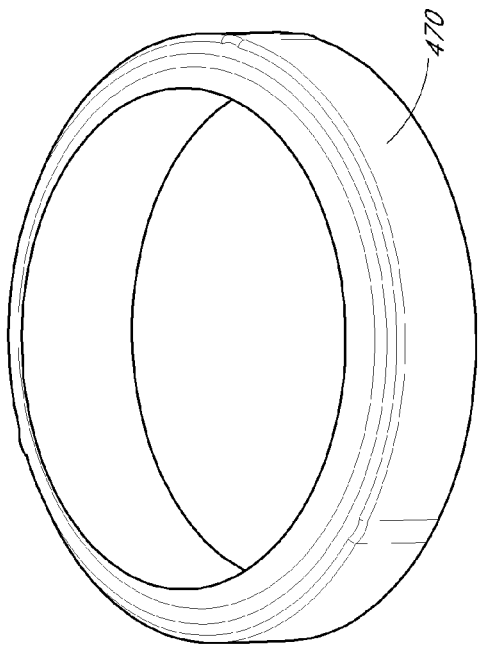
Figure 33B:
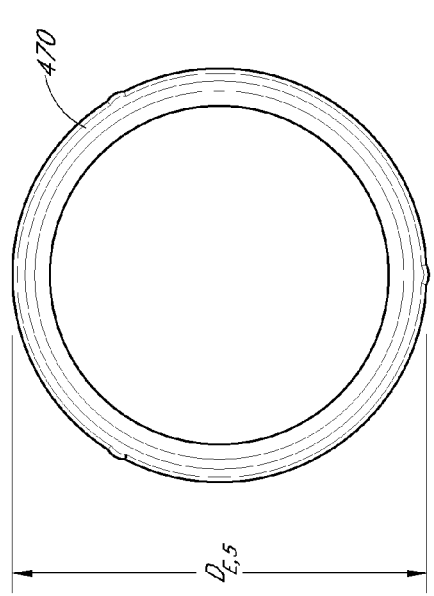
Figure 33C:
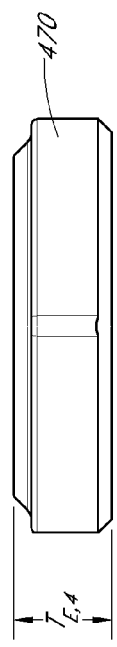

FIGS. 33A-33C illustrate different views of the body 470. In certain aspects, the diameter $D_{E,5}$ of the body 470 can be less than the diameter $D_{E,1}$ of the cap 468, and/or greater than the diameter of the seal 476, the follower 474, and/or the spring 472. In certain aspects, the diameter $D_{E,5}$ of the body 470 can be less than or equal to about 1.0 inches. In certain aspects, the thickness $T_{E,4}$ of the body 470 can be less than or equal to about one-third the diameter $D_{E,5}$ of the body 470, less than or equal to about one-fourth the diameter $D_{E,5}$ of the body 470, or otherwise. In certain aspects, the thickness $T_{E,4}$ of the body can be less than or equal to about 0.25 inches.

In certain variants, it may be desirable for the expiratory valve to vary resistance independent of flow rate. In doing so, the device assembly can increase pressure even during period of low flow to help maximize comfort. The smart expiratory valve can include any of the features of the expiratory valve 414 described herein.

In certain variants, it may be desirable to adjust the expiratory valve pressure setting. For example, it may be desirable to increase or decrease the threshold pressure during the titration process to help determine the ideal pressure setting for the user. In certain embodiments, the entire expiratory valve can be replaced with an expiratory valve having a different pressure setting. In certain embodiments, the expiratory valve can include a processor configured to adjust the pressure setting. For example, the technician can send the expiratory valve a signal to change the pressure setting. In certain aspects, the expiratory valve can include a wireless receiver configured to receive the signal sent from the technician. In certain aspects, when the air flow generator setting changes, the expiratory valve can receive a signal to adjust the pressure setting. In certain embodiments, the pressure settings can be automatically adjusted. For example, the expiratory valve can be smart valve configured to automatically adjust the pressure setting if the valve detects inadequate pressure or flow rates.

Figure 34A:
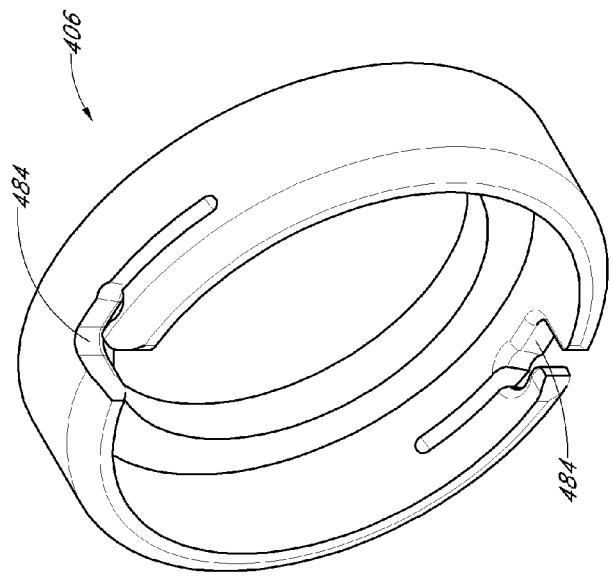
FIGS. 34A-34C illustrate an exemplary embodiment of a valve insert.
Figure 34B:
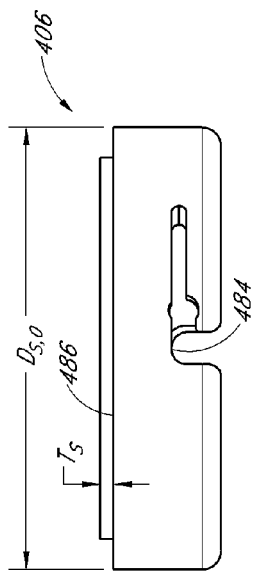
Figure 34C:
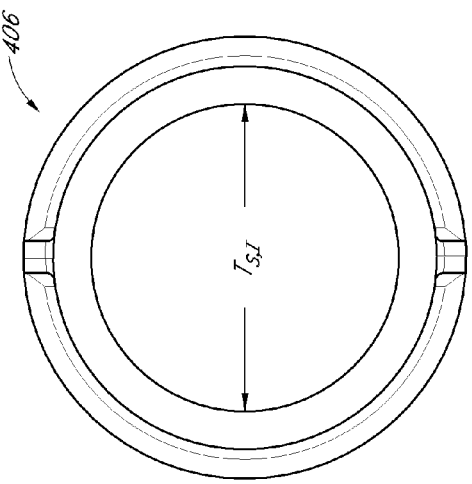

FIGS. 34A-34C illustrate an exemplary embodiment of the expiratory valve insert 406. The expiratory valve insert 406 can be configured to facilitate the exchange of valves depending on the desired relief pressure and improve the capability of doctors to perform patient evaluations. In certain aspects, the inspiratory valve insert 408 can be the same or substantially the same as the expiratory valve insert 406.

The valve insert 406 can be manufactured using any suitable technique, including, but not limited to, machining, molding, extruding, casting, or SLA processing. In certain aspects, the valve insert 406 can include a ceramic material or any metallic material, including, but not limited to aluminum (with or without a finish), stainless steel (e.g., 300 series), titanium, cobalt chrome, nitinol, and/or polymer. In certain aspects, the valve insert 406 can include a medical grade material having a durometer of at least about 50 A and/or less than or equal to about 50 D.

As shown in FIG. 34A, the insert 406 can include one or more detent receiving portions 484 for engaging the expiratory valve 414. In certain aspects, the insert 406 can include a flange portion 486 or other feature to mate with the valve seat 438. In certain aspects, the thickness $T_S$ of the flange portion 486 can be less than or equal to about 0.1 inches, less than or equal to about 0.5 inches, or otherwise. In certain aspects, the thickness $T_S$ of the flange portion can be about 0.035 inches.

In certain aspects, the outer diameter $D_{S,O}$ of the insert 406 can be less than or equal to about 1.5 inches, less than or equal to about 1.25 inches, less than or equal to about 1.0 inches, or otherwise. In certain aspects, the outer diameter $D_{S,I}$ of the insert 406 can be less than or equal to about 1.25 inches, less than or equal to about 1.0 inches, or otherwise.

As described earlier, the device 400 can include one or more air supply connectors 418, 420 to connect the device 400 to any standard air supply tubing. FIGS. 35A-35C illustrates an exemplary embodiment of an air supply connector 418. The connector 418 can be manufactured using any suitable technique, including, but not limited to, machining, molding, or SLA processing. In certain aspects, the connector 418 can include any material having a durometer of at least about 10 A and/or less than or equal to about 50 D. In certain aspects, the connector 418 incudes any medical grade polymer material, including, but not limited to, ABS, PVC, nylon, Pebax®, polycarbonate, Delrin®, rubber, Teflon®, and/or urethane.

In certain aspects, the length $L_A$ of the connector 418 can be less than or equal to about 0.75 inches, less than or equal to about 0.65 inches, or otherwise.

In certain aspects, the connector 418 can include a first connector portion 488 configured to connect to the manifold 404. In certain aspects, the first connector portion 488 can be coupled to the manifold 404 using any connection mechanism, including, but not limited to, an adhesive, a curing technique, a molding technique, a detent, a screw-fit, snap fit, and/or an interference fit. In certain aspects, the outer diameter $D_{A,O}$ of the first connector portion 488 can be less than or equal to about 0.5 inches, less than or equal to about 0.25 inches, or otherwise. In certain aspects, the inner diameter $D_{A,I}$ of the first connector portion 488 can be less than or equal to about 0.25 inches, less than or equal to about 0.2 inches, or otherwise.

In certain aspects, the connector 418 can include a second connector portion 486 configured to connect to any standard air supply tubing. In certain aspects, the second connector portion 486 can be coupled to the air supply tubing using any connection mechanism, including, but not limited to, an adhesive, a curing technique, a molding technique, a detent, a screw-fit, snap fit, and/or an interference fit. In certain aspects, as shown in FIG. 35A, the second connector portion 486 can include a threaded region.

In certain aspects, the manifold 404 and/or mask 402 can be connected to one or more air supply tubes 494. In certain aspects, at least a portion of the air supply tubes 494 can be secured to a strap securing the device 400 to the user's face.

Figure 36:
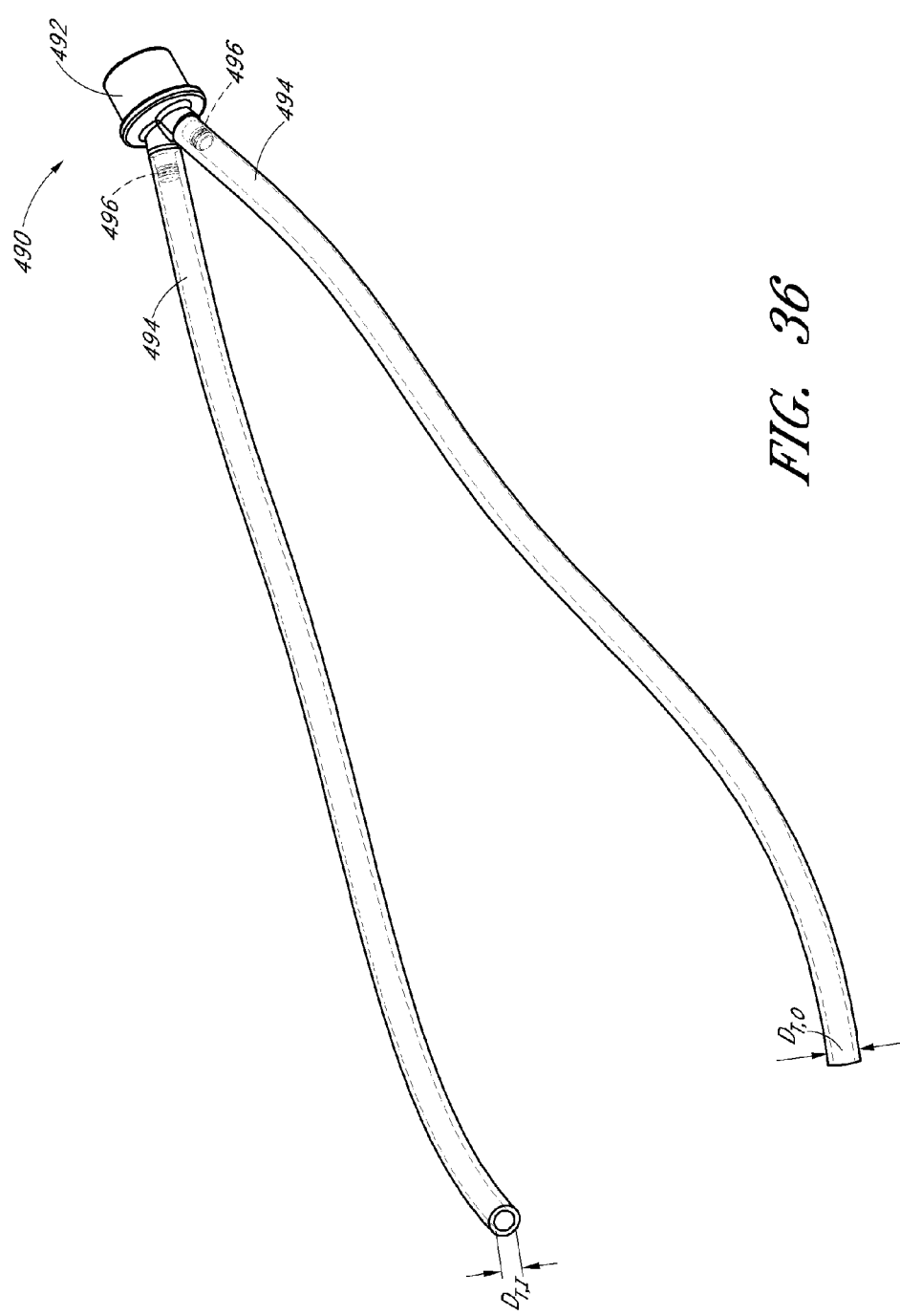
FIG. 36 illustrates an exemplary embodiment of an air supply sub-assembly.

FIG. 36 illustrates an exemplary embodiment of the air supply sub-assembly 490. The sub-assembly 490 can be configured to simultaneously maintain uniform pressure from the air flow generator to the interior volume of the manifold 404 and facilitate re-pressurization during the breathing cycle.

In certain aspects, the sub-assembly 490 can include two air supply tubes 494 and an airflow generator connector 492. In certain aspects, the sub-assembly 490 can be configured to reduce the industry standard flow rate from the airflow generator of greater than 150 L/min to no more than about 80 L/min, typically less than or equal to about 60 L/min. In certain aspects, the flow rate can be less than or equal to about 40 L/min. In certain aspects, the connector 492 can provide an initial constriction and/or the air supply tube(s) 494 can restrict air flow. In certain aspects, the connector 492 can include one or more valves to control air flow from the airflow generator.

The connector 492 can be manufactured using any suitable technique, including, but not limited to, machining, molding, or SLA processing. In certain aspects, the connector 492 can include any material having a durometer of at least about 10 A and/or less than or equal to about 50 D. In certain aspects, the connector 492 incudes any medical grade polymer material, including, but not limited to, ABS, PVC, nylon, Pebax®, polycarbonate, Delrin®, rubber, Teflon®, and/or urethane.

In certain aspects, the connector 492 can include an inlet portion 498 having a single inlet connected to the air flow generator (not shown). In certain aspects, the outer diameter $D_{F,1}$ of the inlet portion 498 can be at least about three times the outer diameter $D_{A,O}$ of the first connector portion 488 and/or less than or equal to about four times the outer diameter $D_{A,O}$ of the first connector portion 488. In certain aspects, the outer diameter $D_{F,1}$ of the inlet portion 498 can be less than or equal to about 1.0 inch, less than or equal to about 0.9 inches, or otherwise.

Figure 37A:
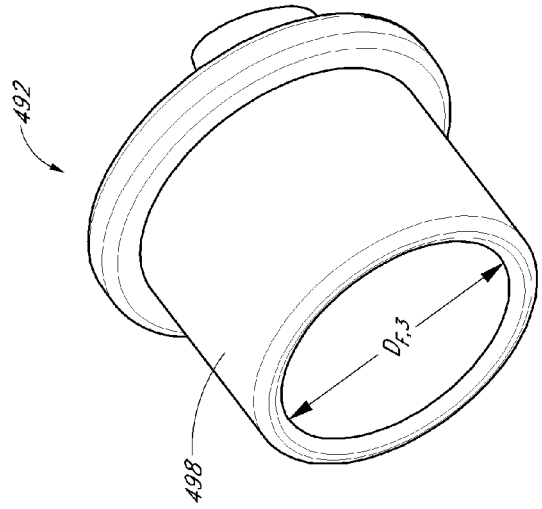
FIGS. 37A-C illustrate an exemplary embodiment of an air supply connector.
Figure 37B:
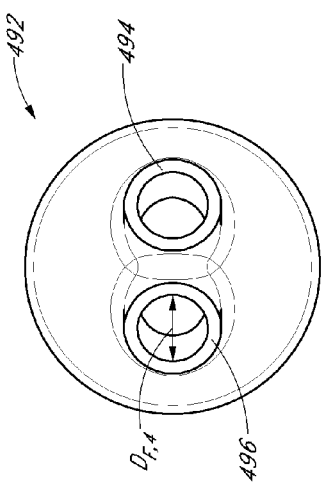
Figure 37C:
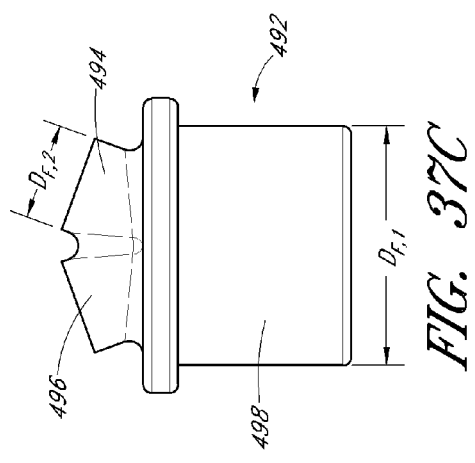

As shown in FIG. 37B, the connector 492 can include two outlet openings 494, 496, each configured to connect to an air supply tube 494. In certain aspects, the outer diameter $D_{F,2}$ of each outlet 494, 496 can be less than or equal to about one-third the outer diameter $D_{F,1}$ of the inlet portion 498, less than or equal to about one-fourth the outer diameter $D_{F,1}$ of the inlet portion 498, or otherwise. In certain aspects, the outer diameter $D_{F,2}$ of the outlet openings 494, 496 can be greater than or equal to the outer diameter $D_{A,O}$ of the first connector portion 488. In certain aspects, the outer diameter $D_{F,2}$ of each outlet 494, 496 can be less than or equal to about 0.3 inches, less than or equal to about 0.25 inches, or otherwise.

In certain aspects, the internal diameter $D_{F,4}$ of each outlet 494, 496 can be less than or equal to about one-third $D_{F,4}$ the internal diameter of the inlet portion 498, less than or equal to about one-fourth the inner diameter $D_{F,4}$ of the inlet portion 498, or otherwise. In certain aspects, the inner diameter $D_{F,4}$ of the outlet openings 494, 496 can be greater than or equal to the internal diameter $D_{A,I}$ of the first connector portion 488, less than or equal to about 1.5 times the internal diameter $D_{A,I}$ of the first connector portion 488, and/or less than or equal to about 1.25 times the internal diameter $D_{A,I}$ of the first connector portion 488.

The air supply tubing 494 can be manufactured using any suitable technique, including, but not limited to, extruding, casting, or necking to create the desired diameter. In certain aspects, the tubing 494 can include any medical grade polymer, including, but not limited to, Tygon®, urethane, Pellethane®, Tecoflex®, silicone, Pebax®, nylon, polyethylene terephthalate, polyethylene, and/or PVC. In certain aspects, the tubing 494 can include a support structure including a metallic material, including, but not limited to, stainless steel (e.g., 300 series), nitinol, steel, carbon fiber, tantalum, palladium, titanium, copper, and/or cobalt chrome.

In certain aspects, the tubing 494 can be configured with a smaller diameter or smaller length as compared to traditional CPAP devices. With smaller tubing 494, the tubing 494 will not kink and will be more user friendly. In certain aspects, the dimensions of the tubing 494 can be controlled to control the amount of air that flows to the mask. In certain aspects, the dimensions of the tubing can vary along the air supply tubing sub-assembly to vary flow. In certain aspects, the tubing 494 can be exchanged depending on the amount of air flow the user desires.

In certain aspects, the cross-section of the air supply tubing 494 can be generally circular or generally elliptical. In certain aspects, the tubing 494 can include an outer diameter $D_{T,O}$ of less than or equal to about the outer diameter $D_{F,1}$ of the first connector portion 498, less than or equal to about one-third of the outer diameter $D_{F,1}$ of the first connector portion 498, less than or equal to about one-fourth of the outer diameter $D_{F,1}$ of the first connector portion 498, or otherwise.

In certain aspects, the tubing 494 can include an internal diameter $D_{T,I}$ of less than or equal to about the internal diameter $D_{F,3}$ of the first connector portion 498, less than or equal to about 80% of the internal diameter $D_{F,3}$ of the first connector portion 498, less than or equal to about 50% of the internal diameter $D_{F,3}$ of the first connector portion 498, less than or equal to about 25% of the internal diameter $D_{F,3}$ of the first connector portion 498, less than or equal to about 20% of the internal diameter $D_{F,3}$ of the first connector portion 498, or otherwise. In certain aspects, the tubing 494 can include an internal diameter $D_{T,I}$ of less than or equal to about the internal diameter $D_{F,4}$ of the outlet opening 496, less than or equal to about three-fourths the internal diameter $D_{F,4}$ of the outlet opening 496, or otherwise. In certain aspects, the tubing 494 can include an internal diameter $D_{T,I}$ of less than or equal to about 0.75 inches, less than or equal to about 0.5 inches, less than or equal to about 0.25 inches, less than or equal to about 0.2 inches, or otherwise. In certain aspects, the tubing 494 can include an internal diameter $D_{T,I}$ of at least about 0.15 inches and/or less than or equal to about 0.25 inches.

As described earlier, the device 400 can be in communication with an air flow generator (not shown). The air flow generator can supply air to the user in addition to the ambient air flowing in through the inspiratory valve 410. The air flow generator can help maintain pressure. For example, if the user stops breathing during exhalation, the pressure generated from the air flow generator helps increase pressure until the expiratory valve opens. If the user stops breathing during inhalation, the inspiratory valve closes and the pressure from the air flow generator helps raise the pressure again until the user inhales normally.

In contrast to traditional CPAP devices that create flow rates greater than or equal to about 150 L/min, the air flow generator in combination with the air supply tubing 494 can create air flow at a rate of less than or equal to about 60 L/min, less than or equal to about 40 L/min, or otherwise. In certain aspects, the air flow generator can be set to a pressure similar to traditional CPAP devices, but the airflow can be restricted and controlled by a restrictor that can adjust the air flow while maintaining constant pressure. The restrictor can be the air supply tubing itself or a separate component disposed within the air supply tubing. The ability to adjust the flow rate enables the device 400 to maintain pressure without the discomfort from a high flow rate of air from the air generator.

In certain aspects, the air flow generator can create a pressure of at least about 5 cmH2O and/or less than or equal to about 15 cmH20. In certain aspects, the air flow generator can create a pressure of less than or equal to about 10 cmH20. In certain aspects, the diameter of the tubing can be less than or equal to about 20 mm, less than or equal to about 15 mm, less than or equal to about 5 mm, or otherwise. In certain aspects, the diameter of the tubing can be at least about 4 mm and/or less than or equal to about 6 mm. In certain aspects, the airflow generator can create a pressure of up to 15 cm H2O at a flow rate of less than 40 L/min delivered through a tube with an internal diameter of less than 4 mm and a length of more than 30 cm.

Ordinarily, the high flow rates of CPAP devices create unintentional leak paths. These unintentional leak paths also stay open because of the high flow rates, which can cause patient discomfort or physiological complications, such as aerophagia or GERD complications. In contrast to traditional CPAP devices, the air flow generator and air supply tubing 494 used with the embodiments described herein do not created unintentional leak paths because of the decreased air flow rate, and non-constant pressure which allows the leak paths to close which can increase patient comfort and compliance. Further, the embodiments described herein can be used to minimize aerophagia or other GERD complications.

In certain aspects, the air flow generator, in combination with the inspiratory 410 and/or expiratory valve 414 can be configured to rapidly re-pressurize the system in less than or equal to about one second. In certain aspects, the air flow generator, in combination with the inspiratory valve, 410 and/or expiratory valve 414, can be configured to rapidly re-pressurize the system up to P critical or the threshold pressure of the expiratory valve 414 to quickly eliminate any apneas. If an apnea occurs, the rescue pressure from the air flow generator can immediately pressurize the system above the P critical pressure such that the pharynx opens.

In certain aspects, the system can re-pressurize the system to a threshold pressure in less than or equal to one second. In certain aspects, the threshold pressure can be at least about 5 cmH20 and/or less than or equal to about 15 cmH20. In certain aspects, the threshold pressure can be about 8 cmH20, about 10 cmH20, about 15 cmH20, or otherwise. In certain aspects, the system can re-pressurize the system at a rate of at least 20 cmH20/second.

In certain variants, the air supply sub-assembly 490 can be configured to maintain a constant pressure even when the air flow supplied from the air flow generator varies or the diameter of the air supply tubing is varied. Although high air flow rates can cause discomfort, the addition of at least some external air flow can create comfort. In certain aspects, the air supply sub-assembly 490 can include one or more valves to allow the user to adjust air flow to their comfort level and still maintain pressure.

In certain aspects, the device 400 and/or air flow generator can include memory to store the user's breathing profile, including, but not limited to, changes in pressure, flow rates, and time elapsed per breathing cycle. In certain aspects, the device 400 and/or air flow generator can include a wireless transmitter to communicate the breathing profile to a health care provider. If valve adjustments are necessary, the health care provider can adjust one or more of the valves or send a new valve to the patient.

In certain aspects, the air flow generator can be sized and shaped to be worn by the user or lay on the bed next to the user. For example, the air flow generator can be worn around the patient's arm, coupled to a belt, or secured to a chest strap. In certain aspects, the air flow generator can be generally rectangular. In certain aspects, the air flow generator can be generally flat.

In certain aspects, the air flow generator can be configured to be positioned in a docking station during use or otherwise. In certain aspects, the docking station can be configured to charge the air flow generator. In certain aspects, the docking station can include a wireless transceiver to communicate breathing profile information to or receive information from the health care provider.

Various embodiments have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

What is claimed is:

1. A system for treating a patient suffering from obstructive sleep apnea or snoring, the system comprising:
    a mask having a contact surface adapted/configured for forming a seal between the mask and the patient's face such that the mask is adapted/configured to surround at least the patient's nostrils;
    a portable air flow generator configured to generate air flow at a relatively low flow rate of less than or equal to about 60 L/min;
    a tube connecting the air flow generator and the mask;
    a one-way, variable resistance expiration valve coupled with the mask or the tube to allow exhaled air to exit the mask during exhalation, wherein the expiration valve provides less total resistance to expired air during a first half of an expiratory phase than during a second half of the expiratory phase while maintaining an elevated pressure above an ambient pressure; and
    an inspiration valve coupled to the mask or the tube to allow ambient air to enter the mask during inhalation;
    wherein the expiration valve closes at the end of exhalation and the inspiration valve opens at the start of inhalation to provide a rapid decrease in minimum pressure to within 2 cm H2O of the ambient pressure, wherein the rapid decrease occurs in less than about 1 second.

2. The system as in claim 1, wherein the expiration valve has an opening pressure of between about 0 cm H2O and about 15 cm H2O.

3. The system as in claim 2, wherein the expiration valve has an opening pressure of between about 2 cm H2O and about 5 cm H2O.

4. The system as in claim 1, wherein the expiration valve opens at an opening pressure between about 0 cm H2O to about 5 cm H2O and closes at a pressure of at least about 5 cm H2O.

5. The system as in claim 1, wherein the expiration valve generates an intra-airway pressure between about 0 cm H2O and about 5 cm H2O during the first half of the expiratory phase and an intra-airway pressure between about 5 cm H2O and about 15 cm H2O during the second half of the expiratory phase.

6. The system as in claim 1, wherein the expiration valve generates greater intra-airway pressure during the second half of the expiratory phase than during the first half.

7. The system as in claim 1, wherein the expiration valve opens to a largest orifice area at an opening pressure and closes continuously during the second half of the expiratory phase.

8. The system as in claim 1, wherein the expiration valve opens to a largest orifice area at an opening pressure and closes incrementally during expiration.

9. The system as in claim 1, wherein the expiration valve creates a larger air passage during the first half of the expiratory phase and a smaller passage during the second half of the expiratory phase.

10. The system as in claim 1, wherein an opening of the expiration valve has a larger diameter during the first half of the expiratory phase and a smaller diameter during the second half of the expiratory phase.

11. The system as in claim 1, wherein the expiration valve opens and closes in response to expiratory pressure generated by exhalation of the patient.

12. The system as in claim 1, wherein the expiration valve opens at an opening pressure and closes completely at an end of expiration.

13. The system as in claim 1, wherein the expiration valve comprises an elastic membrane that expands in response to increasing expiratory pressure, and shrinks in response to decreasing expiratory pressure.

14. The system as in claim 1, wherein the expiration valve comprises an opening that is exposed in response to increasing expiratory pressure and blocked in response to decreasing expiratory pressure.

15. The system as in claim 1, wherein the mask further comprises a port for connecting with the tube.

16. The system as in claim 1, wherein the mask is adapted/configured to form an entrapped volume between the mask and the patient's face of no more than 10 milliliters.

17. The system as in claim 1, wherein the flow rate is between about 1 liter per minute and about 15 liters per minute.

18. The system as in claim 1, wherein the expiration valve is configured to generate substantially constant intra-airway pressure during the first half of the expiratory phase and the second half of the expiratory phase independent of airflow.

19. The system as in claim 1, wherein the expiration valve is configured to open when the intra-airway pressure exceeds an opening pressure and close when the intra-airway pressure falls below the opening pressure.

20. The system as in claim 1, wherein the air flow generator is configured to generate a pressure between about 5 cmH2O and about 20 cmH2O.

21. The system as in claim 1, wherein the air flow generator is configured to re-pressurize the system at a rate of at least 20 cmH2O/second.

22. The system as in claim 1, further comprising a restrictor configured to adjust the air flow without affecting a pressure generated by the air flow generator.

23. The system as in claim 1, wherein the expiration valve is configured to provide variable resistance depending on the patient's airflow.

* * * * *